US009226673B2

(12) United States Patent
Ferguson, Jr. et al.

(10) Patent No.: US 9,226,673 B2
(45) Date of Patent: Jan. 5, 2016

(54) METHODS, SYSTEMS AND COMPUTER PROGRAM PRODUCTS FOR NON-INVASIVE DETERMINATION OF BLOOD FLOW DISTRIBUTION USING SPECKLE IMAGING TECHNIQUES AND HEMODYNAMIC MODELING

(71) Applicant: East Carolina University, Greenville, NC (US)

(72) Inventors: Thomas Bruce Ferguson, Jr., Raleigh, NC (US); Xin-Hua Hu, Greenville, NC (US); Cheng Chen, Greenville, NC (US)

(73) Assignee: East Carolina University, Greenville, NC (US)

( * ) Notice: Subject to any disclaimer, the term of this patent is extended or adjusted under 35 U.S.C. 154(b) by 8 days.

(21) Appl. No.: 13/833,862

(22) Filed: Mar. 15, 2013

(65) Prior Publication Data

US 2013/0245456 A1    Sep. 19, 2013

Related U.S. Application Data

(63) Continuation-in-part of application No. 13/819,817, filed as application No. PCT/US2012/020626 on Jan. 9, 2012.

(60) Provisional application No. 61/476,854, filed on Apr. 19, 2011, provisional application No. 61/431,161, filed on Jan. 10, 2011.

(51) Int. Cl.
*A61B 6/00* (2006.01)
*A61B 5/026* (2006.01)
(Continued)

(52) U.S. Cl.
CPC ............. *A61B 5/0261* (2013.01); *A61B 5/0059* (2013.01); *A61B 5/02007* (2013.01); *G02B 27/48* (2013.01); *G06T 7/0012* (2013.01)

(58) Field of Classification Search
CPC ............... A61B 5/0261; A61B 5/0059; A61B 5/02007; G02B 27/48; G06T 7/0012
USPC .................................................. 600/473–480
See application file for complete search history.

(56) References Cited

U.S. PATENT DOCUMENTS 4,541,433 A    9/1985  Baudino
5,058,596 A    10/1991 Makino et al.
(Continued)

FOREIGN PATENT DOCUMENTS

JP          10-290791        11/1998
WO     WO 2006/021096 A1    3/2006
(Continued)

OTHER PUBLICATIONS

International Preliminary Report on Patentability, PCT/US2012/020626, Jul. 18, 2013.
(Continued)

*Primary Examiner* — Sanjay Cattungal
(74) *Attorney, Agent, or Firm* — Myers Bigel Sibley & Sajovec

(57) ABSTRACT

Non-invasive methods for determining blood flow distribution in a region of interest are provided. The method includes illuminating a region of interest of a subject with a coherent light source; sequentially acquiring at least two speckle images of the region of interest, wherein sequentially acquiring the at least two speckle images comprises acquiring the at least two speckle images in synchronization with motion of the heart of the subject; and electronically processing the at least two acquired speckle images based on the temporal variation of the pixel intensities in the at least two acquired speckle images to generate a laser speckle contrast imaging (LSCI) image, determine distribution of blood flow speed in principal vessels and quantify perfusion distribution in tissue in the region of interest from the LSCI image. The LSCI image enables detection of different blood flow speeds.

28 Claims, 60 Drawing Sheets

(51) Int. Cl.
| | |
|---|---|
| A61B 5/00 | (2006.01) |
| A61B 5/02 | (2006.01) |
| G02B 27/48 | (2006.01) |
| G06T 7/00 | (2006.01) |

(56) References Cited

U.S. PATENT DOCUMENTS

| | | | |
|---|---|---|---|
| 5,074,307 | A | 12/1991 | Aizu et al. |
| 5,129,400 | A | 7/1992 | Makino et al. |
| 5,161,531 | A | 11/1992 | Parsons et al. |
| 5,240,006 | A | 8/1993 | Fujii et al. |
| 5,291,885 | A | 3/1994 | Taniji et al. |
| 5,291,886 | A | 3/1994 | Katayama et al. |
| 5,588,436 | A | 12/1996 | Narayanan et al. |
| 5,692,510 | A | 12/1997 | Gordon et al. |
| 5,860,922 | A | 1/1999 | Gordon et al. |
| 6,045,511 | A | 4/2000 | Ott et al. |
| 6,537,223 | B1 | 3/2003 | Kristiansen |
| 6,631,286 | B2 | 10/2003 | Pfeiffer et al. |
| 6,766,188 | B2 | 7/2004 | Soller |
| 6,915,154 | B1 | 7/2005 | Docherty et al. |
| 6,944,494 | B2 | 9/2005 | Forrester et al. |
| 6,974,416 | B2 | 12/2005 | Booker et al. |
| 7,096,058 | B2 | 8/2006 | Miyahara et al. |
| 7,113,817 | B1 | 9/2006 | Winchester, Jr. et al. |
| 7,200,431 | B2 | 4/2007 | Franco et al. |
| 7,231,243 | B2 | 6/2007 | Tearney et al. |
| 7,270,637 | B2 | 9/2007 | Shin |
| 7,309,313 | B2 | 12/2007 | Nakata et al. |
| 7,404,640 | B2 | 7/2008 | Ferguson et al. |
| 7,468,039 | B2 | 12/2008 | Lui |
| 7,496,395 | B2 | 2/2009 | Serov et al. |
| 7,541,602 | B2 | 6/2009 | Metzger et al. |
| 7,542,790 | B2 | 6/2009 | Jensen et al. |
| 7,809,225 | B2 | 10/2010 | Bouma et al. |
| 7,809,226 | B2 | 10/2010 | Bouma et al. |
| 2003/0225328 | A1 | 12/2003 | DeMeester et al. |
| 2006/0058662 | A1* | 3/2006 | Kobayashi et al. ............ 600/437 |
| 2006/0241460 | A1 | 10/2006 | Kimura et al. |
| 2008/0071176 | A1 | 3/2008 | Docherty et al. |
| 2008/0188726 | A1 | 8/2008 | Presura et al. |
| 2008/0262359 | A1 | 10/2008 | Tearney et al. |
| 2009/0118623 | A1 | 5/2009 | Serov et al. |
| 2009/0177098 | A1 | 7/2009 | Yakubo et al. |
| 2009/0209834 | A1 | 8/2009 | Fine |
| 2010/0056936 | A1 | 3/2010 | Fujii et al. |
| 2010/0067767 | A1 | 3/2010 | Arakita et al. |
| 2011/0013002 | A1 | 1/2011 | Thompson et al. |
| 2011/0071382 | A1 | 3/2011 | Miyazaki et al. |
| 2011/0137169 | A1* | 6/2011 | Akaki et al. .................. 600/443 |
| 2011/0169978 | A1 | 7/2011 | Lasser et al. |
| 2011/0319775 | A1 | 12/2011 | Fujii et al. |
| 2012/0071769 | A1* | 3/2012 | Dunn et al. .................... 600/504 |
| 2012/0095354 | A1* | 4/2012 | Dunn et al. .................... 600/504 |
| 2012/0108956 | A1 | 5/2012 | Warger, II et al. |

FOREIGN PATENT DOCUMENTS

| | | |
|---|---|---|
| WO | WO 2010/131550 A1 | 11/2010 |
| WO | WO 2012/096878 A2 | 7/2012 |

OTHER PUBLICATIONS

Notification of Transmittal of the International Search Report and the Written Opinion of the International Searching Authority, or the Declaration, PCT/US2014/027696, Aug. 26, 2014.

Aizu, Y et al. (1991) "Bio-Speckle Phenomena and Their Application to the Evaluation of Blood Flow" Optics and Laser Technology, vol. 23, No. 4, Aug. 1, 1991.

Brezinski, M. E., G. J. Tearney, et al. (1996). "Imaging of coronary artery microstructure (in vitro) with optical coherence tomography." American Journal of Cardiology 77 (1): 92-93.

Briers et al., (1995) "Quasi real-time digital version of single-exposure speckle photography for full-field monitoring of velocity or flow fields," Optics Communications 116: 36-42.

Briers, J. David, (2001) "Laser Doppler, speckle and related techniques for blood perfusion mapping and imaging," Physiol. Meas. 22: R35-R66.

Chen, Z. P., T. E. Milner, et al. (1997), "Noninvasive imaging of in vivo blood flow velocity using optical Doppler tomography." Optics Letters 22(14): 1119-1121.

Cheng et al., (2004) "Laser speckle imaging of blood flow in microcirculation," Phys. Med. Biol., 49: 1347-1357.

Choi et al., "Linear response range characterization and in vivo application of laser speckle imaging of blood flow dynamics," Journal of Biomedical Optics, Jul./Aug. 2006, 11(4): 041129.

Cioffi, G. A. (2001). "Three common assumptions about ocular blood flow and glaucoma." Survey of Ophthalmology 45: S325-S331.

Draijer, Matthijs J., "High Speed Perfusion Imaging Based on Laser Speckle Fluctuations," Printed by Ridderprint, Ridderker, The Netherlands 2010, 145 pages.

Draijer et al., "Twente Optical Perfusion Camera: system overview and performance for video rate laser Doppler perfusion imaging," Optics Express, Mar. 2, 2009, 17(5): 3211-3225.

Duncan et al., "Can laser speckle flowmetry be made a quantitative tool?," J. Opt. Soc. Am. A, Aug. 2008, 24(8): 2088-2094.

Dunn et al. "Dynamic imaging of cerebral blood flow using laser speckle", J. of Cerebral Blood Flow and Metabolism 21, 195-201 (2001).

Dunn et al., (2011) A Transmissive Laser Speckle Imaging Technique for Measuring Deep Tissue Blood Flow: An Example Application in Finger Joints, Lasers in Surgery and Medicine, 43: 21-28.

Eun, H. C. (1995). "Evaluation of skin blood flow by laser Doppler flowmetry. [Review] [151 refs]." Clinics in Dermatology 13(4): 337-47.

Fercher et al., "Flow Visualization by Means of Single—Exposure Speckle Photography," Optics Communications, Jun. 1, 1981, 37(5): 326-330.

Fujii et al. "Real-time visualization of retinal microcirculation by laser flowgraphy", Opt. Eng. 34, 753-757 (195).

Gandjbakhche, A. H., P. Mills, et al. (1994). "Light-Scattering Technique for the Study of Orientation and Deformation of Red-Blood-Cells in a Concentrated Suspension." Applied Optics 33(6): 1070-1078.

Izatt, J. A., M. D. Kulkarni, et al. (1996). "Optical coherence tomography and microscopy in gastrointestinal tissues." IEEE Journal of Selected Topics in Quantum Electronics 2(4): 1017.

Jang, I. K., G. J. Tearney, et al. (2001). "Visualization of Tissue Prolapse Between Coronary Stem Struts by Optical Coherence Tomography: Comparison With Intravascular Ultrasound." Images in Cardiovascular Medicine, American Heart Association, http://circ.ahajournals.org/content, p. 2754.

Kruijt et al., (2006), "Laser speckle imaging of dynamic changes in flow during photodynamic thearpy," Lasers Med Sci, 21: 208-212

Leitgeb, R. A., L. Schmetterer, et al. (2003). "Real-time assessment of retinal blood flow with ultrafast acquisition by color Doppler Fourier domain optical coherence tomography." Optics Express 11(23): 3116-3121.

Lesnick et al., "New Generation Optical Would Monitoring Device," CW Optics, Inc., Yorktown, Virginia, USA, Admitted Prior Art, 1 page.

Li et al., "Imaging cerebral blood flow through the intact rate skull with temporal laser speckle imaging," Optics Letters, Jun. 15, 2006, 31(12): 1824-1826.

Matsievskii, D.D., (2004) "Blood Flow Measurements in Studies of Macro- and Microcirculation," Bulletin of Experimental Biology and Medicine, 6: 541-544.

Nadkarni, Seemantini K. et al (2005) "Characterization of Atherosclerotic Plaques by Laser Speckle Imaging" Circulation vol. 112 pp. 885-892.

Nelson, J. S., K. M. Kelly, et al. (2001). "Imaging blood flow in human port-wine stain in situ and in real time using optical Doppler tomography." Archives of Dermatology 137(6): 741-744.

Notification of Transmittal of the International Search Report and the Written Opinion of the International Searching Authority, or the Declaration, PCT/US2012/020626, Jul. 20, 2012

(56) References Cited

OTHER PUBLICATIONS

Ohtsubo et al., (1976) "Velocity measurement of a diffuse object by using time-varying speckles," Optical and Quantum Electronics, 8: 523-529.
Oshima, M., R. Torii, et al. (2001). "Finite element simulation of blood flow in the cerebral artery." Computer Methods in Applied Mechanics and Engineering 191 (6-7): 661-671.
Parthasarathy et al., "Laser speckle contrast imaging of cerebral blood flow in humans during neurosurgery: a pilot clinical study," Journal of Biomedical Optics, 15(6) Nov./Dec. 2010, pp. 066030-1 to 066030-8.
Rege et al., "Multiexposure laser speckle contrast imaging of the angiogenic microenvironment," Journal of Biomedical Optics, 16(5), May 2011, pp. 056006-1 to 056006-10.
Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," Optics Letters. vol. 27, No. 19, Oct. 1, 2002, pp. 1702-1704.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Ruth, B. "blood flow determination by the laser speckle method", Int J Microcirc: Clin Exp, 1990, 9:21-45.
Ruth, et al., (1993) "Noncontact Determination of Skin Blood Flow Using the Laser Speckle Method: Application to Patients with Peripheral Arterial Occlusive Disease (PAOD) and to Type-I Diabetes," Lasers in Surgery and Medicine 13: 179-188.
Subhash, Hrebesh M., "Biophotonics Modalities for High-Resolution Imaging of Microcirculatory Tissue Beds Using Endogenous Contrast: A Review of Present Scenario and Prospects," International Journal of Optics, vol. 2011, Article ID 293684, 20 pages.
Teamey et al., "Atherosclerotic plaque characterization by spatial and temporal speckle pattern analysis", CLEO 2001, vol. 56, pp. 307-307.
Wang, X, J., T. E. Milner, et al. (1997). "Measurement of fluid-flow-velocity profile in turbid media by the use of optical Doppler tomography." Applied Optics 36(1): 144-149.
Weber et al., (2004) "Optical imaging of the spatiotemporal dynamics of cerebral blood flow and oxidative metabolism in the rat barrel cortex," European Journal of Neuroscience, 20: 2664-2670.
White, Brian R. et al., "In Vivo Dynamic Human Retinal Blood Flow Imaging Using Ultra-High Speed Spectral Domain Optical Doppler Tomography," Optics Express, Dec. 15, 2002, 11(25): 3490-3497.
Wussling et al., "Laser diffraction and speckling studies in skeletal and heart muscle", Biomed, Biochem, Acta, 1986, 45(1/2):S 23-S 27.
Yazdanfar et al., "In Vivo Imaging in blood flow in human retinal vessels using color Doppler optical coherence tomography", SPIE, 1999 vol. 3598, pp. 177-184.
Yazdanfar, S., A. M. Rollins, et al. (2000). "Imaging and velocimetry of human retinal circulation with color Doppler optical coherence tomography." Optics Letters, vol. 25, No. 19, Oct. 1, 2000, pp. 1448-1450.
Yazdanfar, S., A. M. Rollins, et al. (2003), "In vivo imaging of human retinal flow dynamics by color Doppler optical coherence tomography," Archives of Ophthalmology 121(2): 235-239.
Zakharov et al., Dynamic laser speckle imaging of cerebral blood flow, Optics Express, vol. 17, No, 16, Aug. 3, 2009, pp. 13904-13917.
Zakharov et al., "Quantitative modeling of laser speckle imaging," Optics Letters, Dec. 1, 2006; 31(23): 3465-3467.
Zhao, Y. H., Z. P. Chen, et al. (2000). "Doppler standard deviation imaging for clinical monitoring of in vivo human skin blood flow." Optics Letters 25(18) : 1358-1360.
Wardell et al., "ECG-Triggering of the Laser Doppler Perfusion Imaging Signal," Proceedings of the 20th Annual International Conference of the IEEE Engineering in Medicine and Biology Socieity, vol. 20, No. 4, 1998, pp. 1879-1880.

\* cited by examiner

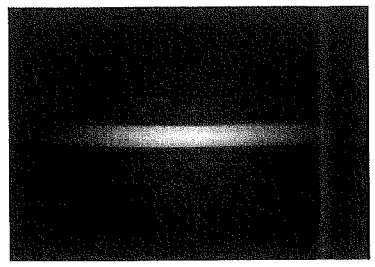

Average of 97 frames
delta: 1 secs; exposure time:
0.003 secs; resolution: 320*240;
Velocity limit: 7.0325 cm/s

A

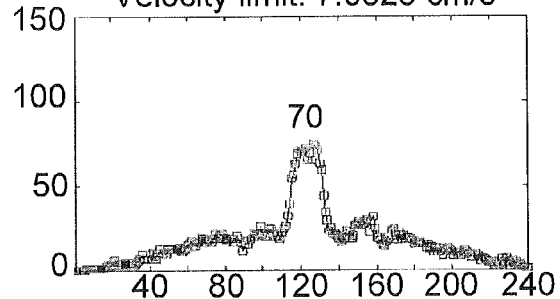

middle vertical line of inverted
speckle contrast delta: 1 secs;
exposure time 0.003 secs;
resolution: 320*240;
Velocity limit: 7.0325 cm/s

B

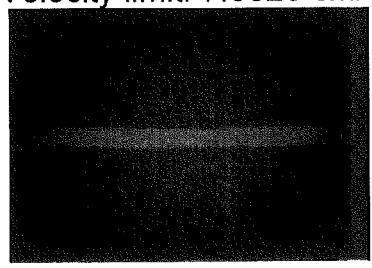

Inverted speckle
contrast gray scale
delta: 1 secs;
exposure time: 0.003 secs;
Resolution: 320*240;
Velocity limit: 7.0325 cm/s

C

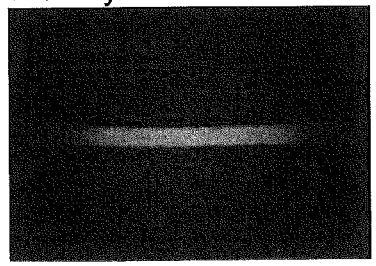

Inverted speckle contrast color
delta: 1 secs;
exposure time: 0.003 secs;
resolution: 320*240;
Velocity limit: 7.0325 cm/s

D

© 2010 ECU

Figure 14

Average of 89 delta: 1 secs;
exposure time: 0.003 secs;
resolution: 320*240;
Velocity limit: 6.4525 cm/s

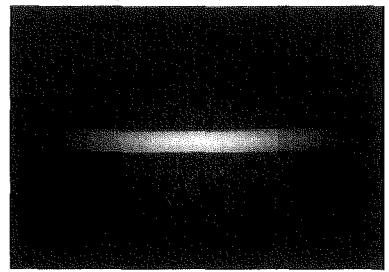

A

Middle vertical line of
inverted speckle contrast
delta: 1 secs;
exposure time: 0.003 secs;
resolution: 320*240;
Velocity limit: 6.4525 cm/s

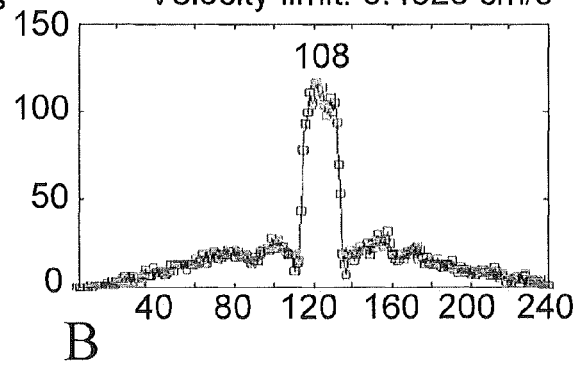

B

Inverted speckle contrast
gray scale
delta: 1 secs;
exposure time: 0.003 secs;
resolution: 320*240;
Velocity limit: 6.4525 cm/s

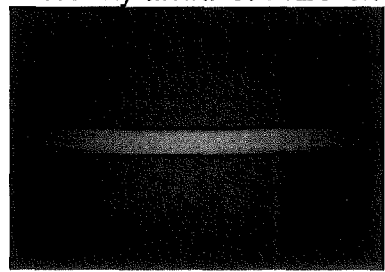

C

Inverted speckle contrast color
delta: 1 secs;
exposure time: 0.003 secs;
resolution: 320*240;
Velocity limit: 6.4525 cm/s

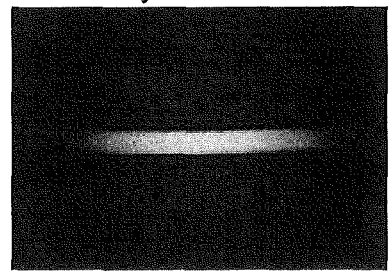

D

© 2010 ECU

Figure 16

Average of 90 frames
delta: 1 secs;
exposure time 0.003 secs;
resolution: 320*240
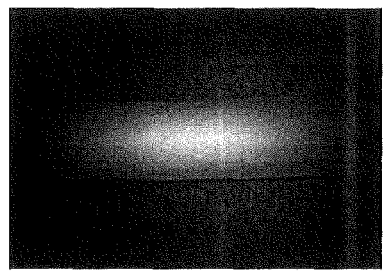
A
middle vertical profile of
inverted speckle contrast
delta: 1 secs; exposure time:
0.003 secs; resolution: 320*240
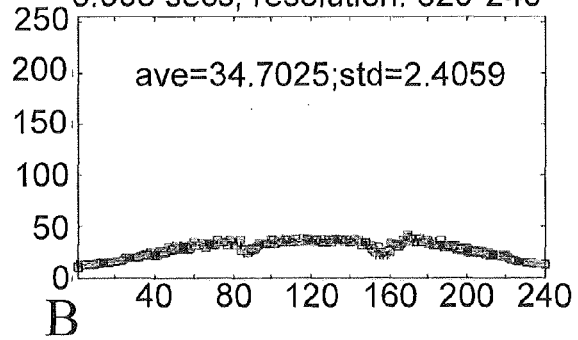
B
inverted speckle
contrast gray scale
delta: 1 secs;
exposure time: 0.003 secs;
resolution: 320*240
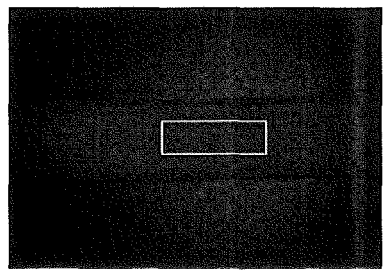
C
inverted speckle
contrast color
delta: 1 secs;
exposure time: 0.003 secs;
resolution: 320*240
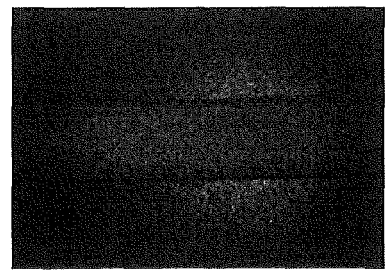
D © 2010 ECU
Figure 34

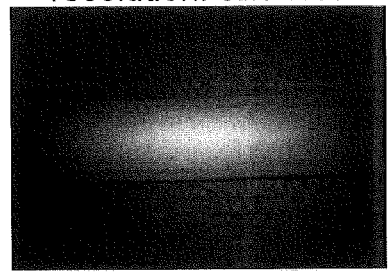
A
flow:500mL;
Average of 97 frames
delta: 1 secs;
exposure time: 0.003 secs;
resolution: 320*240
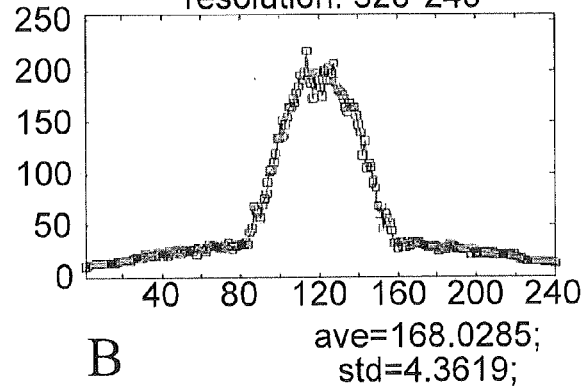
B
middle vertical profile
of inverted
speckle contrast delta: 1 secs;
exposure time: 0.003 secs;
resolution: 320*240
ave=168.0285;
std=4.3619;
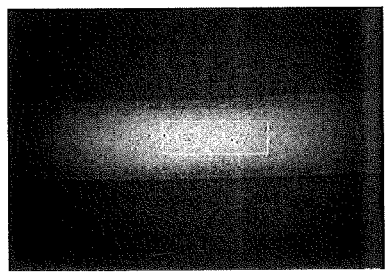
C
inverted speckle
contrast gray scale
delta: 1 secs;
exposure time: 0.003 secs;
resolution: 320*240
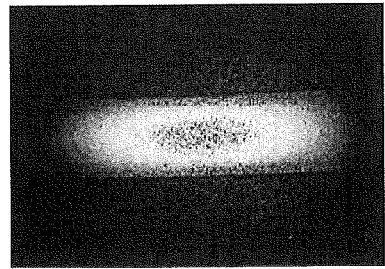
D
inverted speckle
contrast color
delta: 1 secs;
exposure time: 0.003 secs;
resolution: 320*240
© 2010 ECU
Figure 36 flow:1000mL;
Average of 98 frames
delta: 1 secs;
exposure time: 0.003 secs;
resolution: 320*240
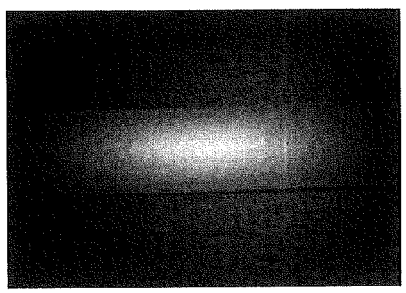
A
middle vertical profile of inverted
speckle contrast delta: 1 secs;
exposure time: 0.003 secs;
resolution: 320*240
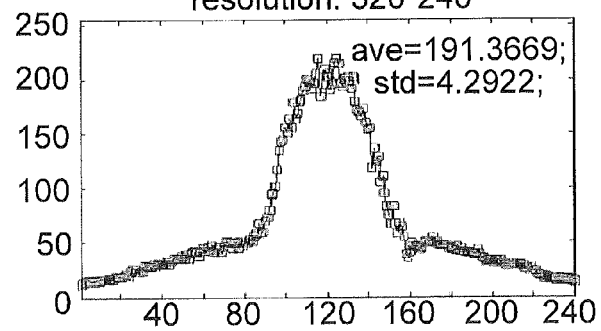
ave=191.3669;
std=4.2922;
B
inverted speckle
contrast gray scale
delta: 1 secs;
exposure time: 0.003 secs;
resolution: 320*240
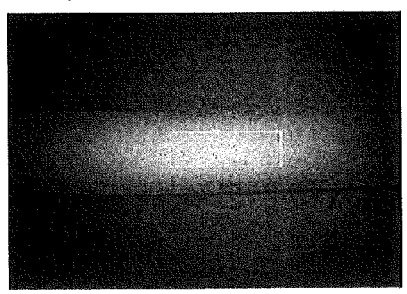
C
inverted speckle
contrast color
delta: 1 secs;
exposure time: 0.003 secs;
resolution: 320*240
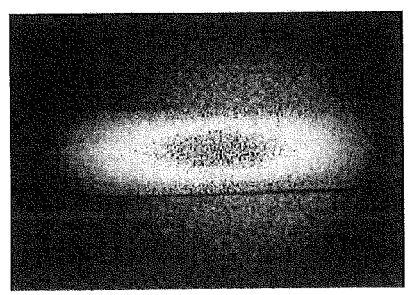
D © 2010 ECU
Figure 37

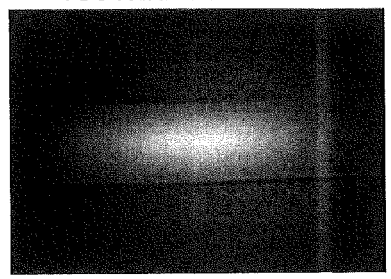
flow:0mL;
Average of 98 frames
delta: 1 secs;
exposure time: 0.003 secs;
resolution: 320*240
A
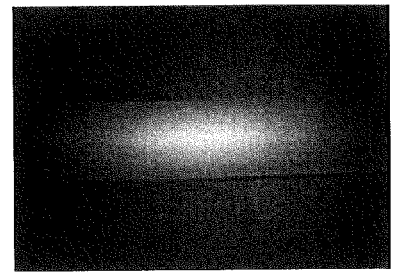
flow:0mL;
Average of 98 frames
delta: 1 secs;
exposure time: 0.003 secs;
resolution: 320*240
B
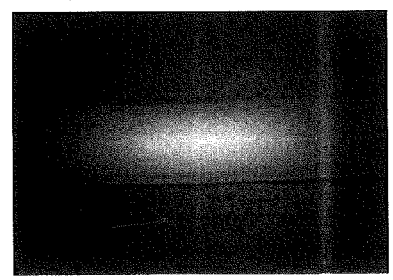
flow:500mL;
Average of 98 frames
delta: 1 secs;
exposure time: 0.003 secs;
resolution: 320*240
C
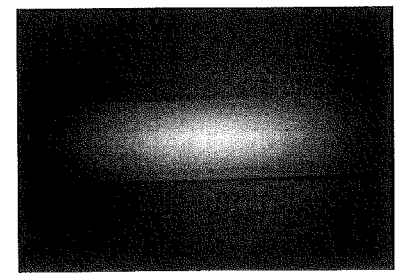
flow:1000mL;
Average of 98 frames
delta: 1 secs;
exposure time: 0.003 secs;
resolution: 320*240
D
© 2010 ECU
Figure 38

© 2010 ECU flow:0mL; Average of 96 frames delta: 1 secs; exposure time: 0.003 secs; resolution: 320*240
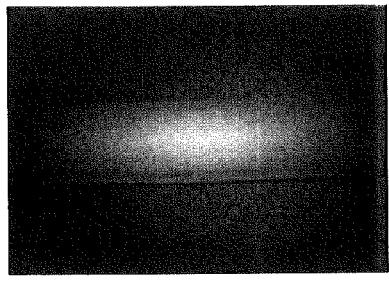
A
middle vertical profile of inverted speckle contrast delta: 1 secs; exposure time: 0.003 secs; resolution: 320*240
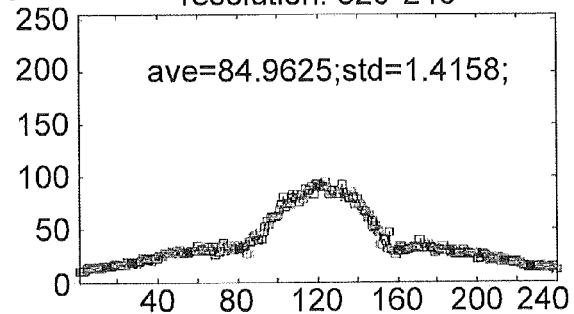
ave=84.9625;std=1.4158;
B
inverted speckle contrast gray scale delta: 1 secs; exposure time: 0.003 secs; resolution: 320*240
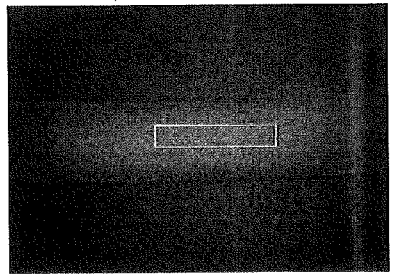
C
inverted speckle contrast color Delta: 1 secs; exposure time: 0.003 secs; resolution: 320*240
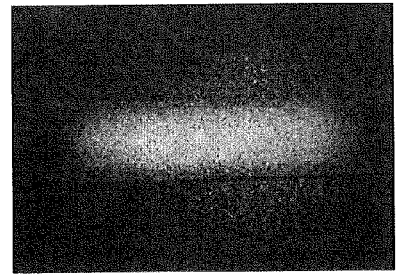
D © 2010 ECU
Figure 43

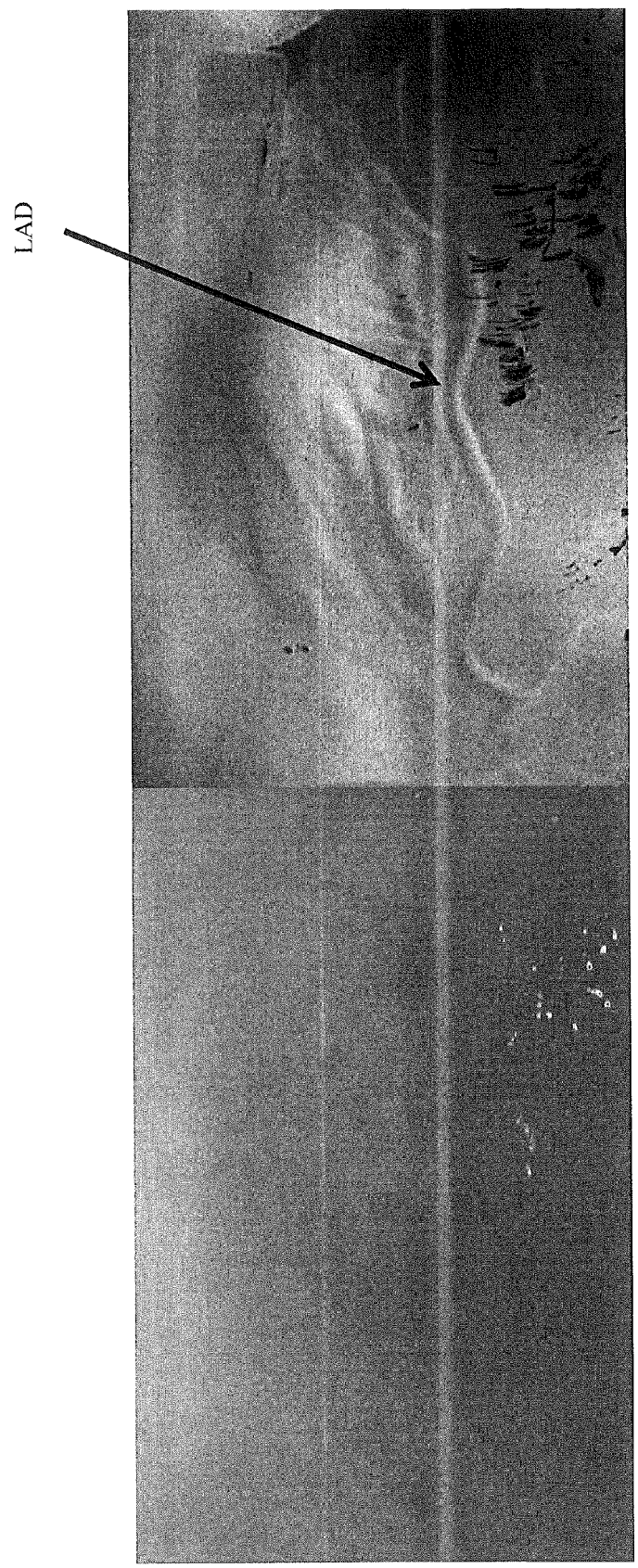

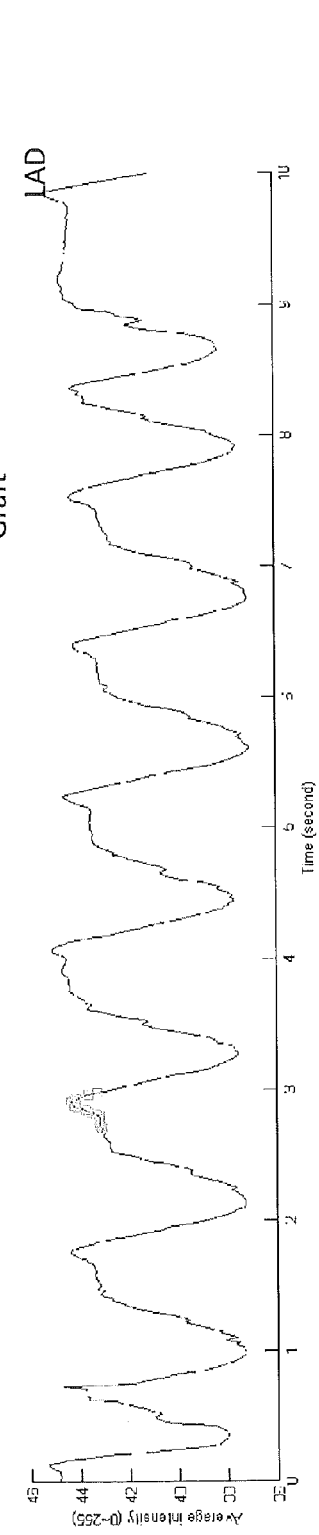
Figure 58A  Figure 58B  Figure 58C
Figure 58D

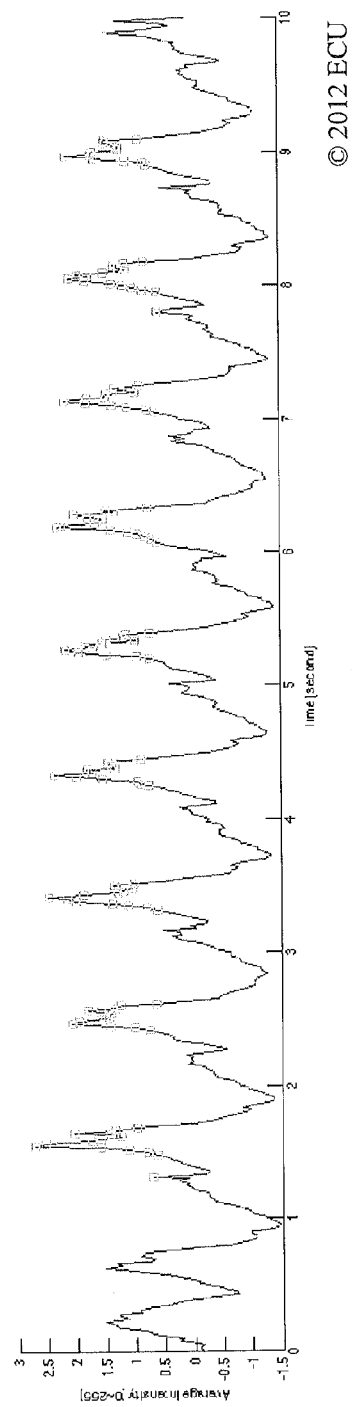
Figure 61A
Figure 61B
Figure 61C
Figure 61D

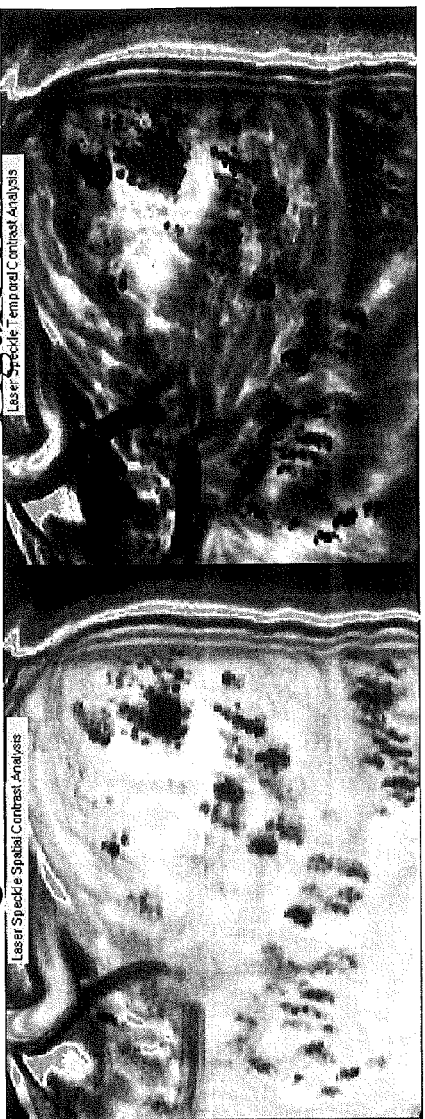
Figure 62A  Figure 62B  Figure 62C
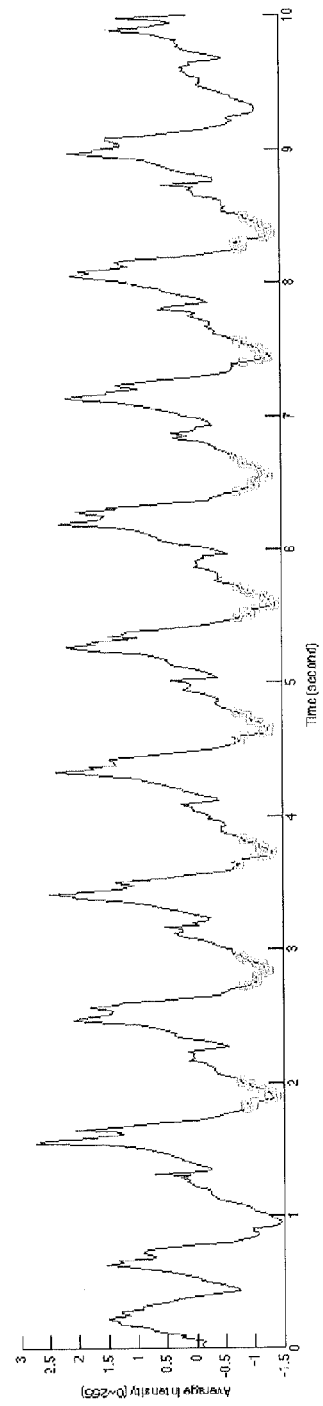
Figure 62D

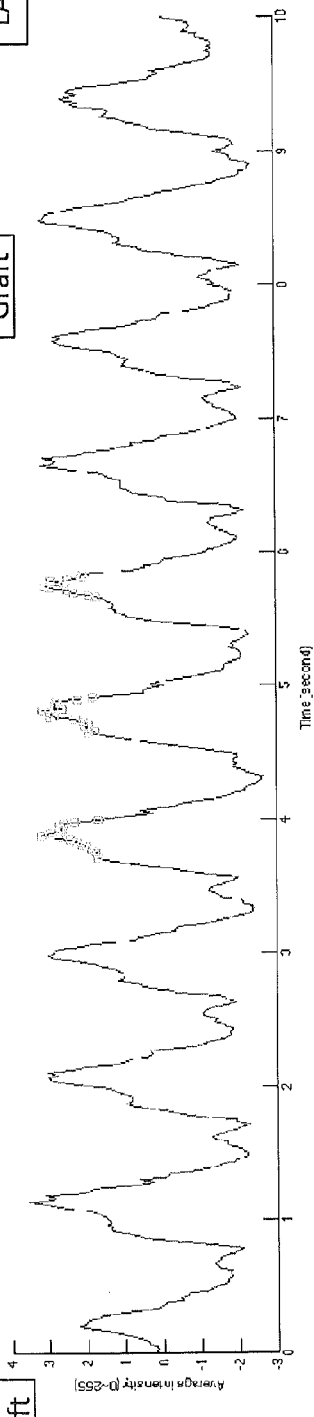
Figure 63A
Figure 63B
Figure 63C
Figure 63D

METHODS, SYSTEMS AND COMPUTER PROGRAM PRODUCTS FOR NON-INVASIVE DETERMINATION OF BLOOD FLOW DISTRIBUTION USING SPECKLE IMAGING TECHNIQUES AND HEMODYNAMIC MODELING

CLAIM OF PRIORITY

The present application claims priority from U.S. application Ser. No. 13/819,817, filed Feb. 28, 2013, which is a U.S. national phase application of PCT/US2012/020626, filed Jan. 9, 2012, which claims priority to U.S. Provisional Application No. 61/431,161, filed Jan. 10, 2011 and U.S. Provisional Application No. 61/476,854, filed Apr. 19, 2011, the disclosures of which are hereby incorporated herein by reference as if set forth in their entirety.

RESERVATION OF COPYRIGHT

A portion of the disclosure of this patent document contains material which is subject to copyright protection. The copyright owner, East Carolina University of Greenville, N.C., has no objection to the reproduction by anyone of the patent document or the patent disclosure, as it appears in the Patent and Trademark Office patent file or records, but otherwise reserves all copyright rights whatsoever.

FIELD

The present inventive concept relates generally to determination of blood flow distribution and, more particularly, to the use of speckle imaging techniques for non-invasive determination of blood flow distribution.

BACKGROUND

Revascularization is an interventional procedure for the provision of a new, additional, or augmented blood supply to a body part or organ. Revascularization typically involves a thorough analysis and/or diagnosis and treatment of the existing diseased vasculature of the affected organ. In some instances, revascularization can be aided by the use of different imaging modalities, such as magnetic resonance imaging (MRI), positron emission tomography (PET) scan, computed tomography (CT) scan, and X ray fluoroscopy.

Revascularization is designed to improve blood flow to tissues perfused by the principal arterial vessel(s) supplying that tissue. Revascularization may be needed, for example, due to an obstruction in the native arterial vessel supplying that tissue. Coronary artery bypass grafting (CABG) is a revascularization procedure that may be used to increase blood flow to ischemic myocardium by bypassing the native coronary obstructions.

There are two measurement components to the revascularization evaluation, blood flow in the principal arterial supply and quantitative perfusion in the tissue. Conventional methods for measurement of blood flow and perfusion are limited, despite the benefit these measurements would bring to the clinical evaluation of the quality of the revascularization procedure.

Some conventional interoperative methods of measuring blood flow are based on ultrasound detection of blood flow in the graft conduits, but not the native principal arterial vessel(s). Some conventional angiographic evaluation methods include conventional coronary angiography performed in a hybrid operating room setting at the time of surgery. Recently, Novadaq Technologies, Inc. of Toronto, Canada has introduced fluorescence imaging that uses both angiographic image evaluation and quantitative perfusion evaluation to CABG.

However, ultrasound detection typically requires physical contact between the graft vessel and a probe. Furthermore, ultrasound detection typically relies on proper placement of the probe around the vessel to obtain accurate measurement of flow speed and can be unreliable, measurement to measurement.

Coronary angiography typically requires radiation and administration of toxic image contrast agent. Furthermore, hybrid operating rooms used for coronary angiography can be relatively expensive, making this method unavailable to many patients undergoing CABG.

Fluorescence imaging typically requires injection of non-toxic dye into the patient. Furthermore, fluorescence imaging typically cannot provide information to directly determine the speed of blood flow in principal vessels. Despite the above, there remains a need for alternative methods of determining blood flow.

SUMMARY

Some embodiments of the present inventive concept provide a non-invasive method for measuring blood flow in principal vessels of a heart of a subject, the method including illuminating a region of interest in the heart with a coherent light source, wherein the coherent light source has a wavelength of from about 600 nm to about 1100 nm; sequentially acquiring at least two speckle images of the region of interest in the heart during a fixed time period, wherein sequentially acquiring the at least two speckle images comprises acquiring the at least two speckle images in synchronization with motion of the heart of the subject; and electronically processing the at least two acquired speckle images based on the temporal variation of the pixel intensities in the at least two acquired speckle images to generate a laser speckle contrast imaging (LSCI) image and determine spatial distribution of blood flow speed in the principal vessels and perfusion distribution in tissue in the region of interest in the heart from the LSCI image.

In further embodiments, sequentially acquiring the at least two speckle images may include electronically monitoring an EKG cardiac cycle of the subject; and electronically synchronizing acquisition of speckle images with the EKG signals.

In still further embodiments, the sequentially acquiring and the electronically evaluating may be performed before a procedure performed on a subject and after the procedure performed on the subject. The method may further include comparing the determined blood flow speed in the principal vessels and perfusion distribution in tissue in the region of interest in the heart before the procedure with the determined blood flow speed in the principal vessels and perfusion distribution in tissue in the region of interest in the heart after the procedure to access success of the procedure.

In some embodiments, the method further includes calculating a velocity field for the region of interest in the heart; calculating blood flow speed in the region of interest in the heart based on the calculated velocity field; and comparing the calculated blood flows speed in the region of interest to the blood flow speed determined using the acquired at least two speckle images of the region of interest in the heart to verify results obtained using the at least two speckle images.

In further embodiments, the velocity field is calculated using equations (9) and (10) set out below.

In still further embodiments, the coherent light source may have a wavelength of from about 600 nm to about 1100 nm and may allow relatively deep penetration of light into tissues to thereby allow an accurate determination of blood flow speed in the principal vessels and the perfusion distribution.

In some embodiments, the coherent light source may include a laser configured to illuminate the region of interest with a substantially constant intensity. The laser may have a fixed or variable wavelength of from about 600 nm to about 1100 nm. The laser may generate a laser beam having a substantially constant intensity within a field-of-view (FOV) of an imaging unit. The laser may be a low power and continuous-wave laser such that the subject does not require any protective apparatus to shield the subject from effects of the laser.

In further embodiments, data acquisition may include sequentially acquiring from about 50 to about 1000 speckle images using the camera during the fixed time period of from about 1 ms to about 200 ms.

In still further embodiments, sequentially acquiring may include acquiring from about 200 to about 500 speckle images during the fixed time period.

In some embodiments, the fixed time period may be selected based on in situ acquisition of blood flow speed of the subject in the region of interest.

Further embodiments of the present inventive concept provide a non-invasive method for measuring blood flow in principal vessels of a subject, the method including illuminating a region of interest with a coherent light source, wherein the coherent light source has a wavelength of from about 600 nm to about 1100 nm; sequentially acquiring at least two speckle images of the region of interest during a fixed time period; electronically processing the at least two acquired speckle images based on the temporal variation of the pixel intensities in the at least two acquired speckle images to generate a laser speckle contrast imaging (LSCI) image, and determine spatial distribution of blood flow speed in the principal vessels and quantify perfusion distribution in tissue in the region of interest from the LSCI image; calculating a velocity field for the region of interest; calculating blood flow rate in the region of interest based on the calculated velocity field; and comparing the calculated blood flow speed in the region of interest to the blood flow speed determined using the acquired at least two speckle images of the region of interest to verify results obtained using the at least two speckle images.

Still further embodiments of the present inventive concept provide a non-invasive system for measuring blood flow in principal vessels in a heart of a subject, the system including a coherent light source configured to illuminate a region of interest in the heart of the subject, the coherent light source having a wavelength of from about 600 nm to about 1100 nm. A camera in communication with the coherent light source is provided that is configured to sequentially acquire at least two speckle images of the region of interest in the heart during a fixed time period, wherein acquisition of the at least two speckle images is synchronized with motion of the heart of the subject. A data processing circuit is also provided that is configured to evaluate the temporal variation of the pixel intensities in the at least two acquired speckle images to generate an LSCI image and determine spatial distribution of blood flow speed in the principal vessels and quantify perfusion distribution in tissue in the region of interest in the heart from the LSCI image.

Some embodiments of the present inventive concept provide a computer program product for measuring blood flow in principal vessels in a heart of a subject, the computer program product comprising a non-transitory computer-readable storage medium having computer-readable program code embodied in the medium. The computer-readable program code includes computer readable program code configured to electronically evaluate temporal variation of the pixel intensities in the at least two acquired speckle images to generate an LSCI image and determine spatial distribution of blood flow speed in the principal vessels and quantify perfusion distribution in tissue in the region of interest in the heart from the LSCI image, wherein the at least two speckle images are sequentially acquired using a camera during a fixed time period when the region of interest of the subject is illuminated by a coherent light source having a wavelength of from about 600 nm to about 1100 nm; and computer readable program code configured to sequentially acquire the at least two speckle images in synchronization with motion of the heart of the subject.

Further embodiments of the present inventive concept provide a non-invasive method for determining blood flow distribution in a region of interest. The method includes illuminating a region of interest of a subject with a coherent light source; sequentially acquiring at least two speckle images of the region of interest, wherein sequentially acquiring the at least two speckle images comprises acquiring the at least two speckle images in synchronization with motion of the heart of the subject; and electronically processing the at least two acquired speckle images based on the temporal variation of the pixel intensities in the at least two acquired speckle images to generate a laser speckle contrast imaging (LSCI) image, determine distribution of blood flow speed in principal vessels and quantify perfusion distribution in tissue in the region of interest from the LSCI image. The LSCI image enables detection of different blood flow speeds.

In still further embodiments, acquiring the at least two speckle images in synchronization with motion of the heart of the subject may further include electronically monitoring an EKG cardiac cycle of the subject; and electronically synchronizing acquisition of speckle images with the EKG signals.

In some embodiments, the region of interest may be a beating heart and the method may further include generating instantaneous flow and/or perfusion maps for the region of interest at any time during a cardiac cycle using the EKG signals to synchronize data acquisition. The instantaneous flow and/or perfusion maps generated at first and second times may be compared to determine efficacy of a treatment. In certain embodiments, the first time may be a time before a treatment is administered and the second time may be a time after the treatment is administered.

In further embodiments, the region of interest may be a beating heart and the method may further include generating average flow and/or perfusion maps for the region of interest over two or more cardiac cycles using EKG signals to synchronize data acquisition. Average flow and/or perfusion maps generated at first and second times may be compared to determine efficacy of a treatment. In certain embodiments, the first time may be a time before a treatment is administered and the second time may be a time after the treatment is administered.

In still further embodiments, the region of interest may be a non-cardiac region of the subject and the method may further include generating instantaneous flow and/or perfusion maps at any time during data acquisition using the EKG signals to synchronize data acquisition. Instantaneous flow and/or perfusion maps generated at first and second times may be compared to determine efficacy of a treatment. The first time may be a time before a treatment is administered and the second time may be a time after the treatment is administered.

In some embodiments, the region of interest may be a non-cardiac region of the subject and the method may further include generating average flow and/or perfusion maps over two or more periods of data acquisition using EKG signals to synchronize data acquisition. Average flow and/or perfusion maps generated at first and second times may be compared to determine efficacy of a treatment. The first time may be a time before a treatment is administered and the second time may be a time after the treatment is administered.

In further embodiments, the coherent light source may have a wavelength of from about 600 nm to about 1100 nm.

Still further embodiments of the present inventive concept provide non-invasive methods for determining blood flow distribution in a region of interest. The method includes illuminating a region of interest of a subject with a coherent light source; sequentially acquiring at least two speckle images of the region of interest, wherein sequentially acquiring the at least two speckle images comprises acquiring the at least two speckle images in synchronization with motion of the heart of the subject; electronically processing the at least two acquired speckle images based on the temporal variation of the pixel intensities in the at least two acquired speckle images to generate a laser speckle contrast imaging (LSCI) image, determine distribution of blood flow speed in principal vessels and quantify perfusion distribution in tissue in the region of interest from the LSCI image; generating one of instantaneous flow and/or perfusion maps for the region of interest at any time during data acquisition using EKG signals to synchronize data acquisition and average flow and/or perfusion maps over two or more periods of data acquisition using the EKG signals to synchronize data acquisition; and comparing one of the instantaneous flow and/or perfusion maps and the average flow and/or perfusion maps generated at first and second times to determine efficacy of a treatment.

Some embodiments of the present inventive concept provide non-invasive methods for determining blood flow distribution in a region of interest. The method may include illuminating a region of interest of a subject with a coherent light source; sequentially acquiring at least two speckle images of the region of interest, wherein sequentially acquiring the at least two speckle images comprises acquiring the at least two speckle images in synchronization in synchronization with an electrocardiogram (EKG); selecting at least two speckle images using EKG-based timing; processing the selected images to determine an instantaneous/average flow speed (centimeter/second) in the region of interest using at least one of a temporal contrast algorithm and a spatial contrast algorithm, wherein the EKG is used at any time during data acquisition and analysis to select frames to be processed, to locate the instantaneous flow speed in one or more EKG cycles, and/or to target the beginning and ending time of average flow speed analyses; inputting the instantaneous/average flow speed image into the analysis model to generate a flow rate (cubic centimeter/second) map in the principal vessels and a perfusion map in the microvascular structure; and generating a direction of flow and pressure.

Related systems and computer program products may also be provided.

It is noted that aspects of the inventive concept described with respect to some embodiments, may be incorporated in different embodiments although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present inventive concept are explained in detail in the specification set forth below. Further features, advantages and details of the present inventive concept will be appreciated by those of ordinary skill in the art from a reading of the figures and the detailed description of the embodiments that follow, such description being merely illustrative of the present inventive concept.

BRIEF DESCRIPTION OF THE FIGURES

FIGS. 14A through 14D are images illustrating a "flow 1" case in accordance with some embodiments of the present inventive concept(s).

FIGS. 16A through 16D are images illustrating a "flow 3" case in accordance with some embodiments of the present inventive concept(s).

FIGS. 34A through 34D are digital images illustrating a "tube clamped" situation in accordance with some embodiments of the present inventive concept(s).

FIGS. 36A through 36D are images illustrating a "pump reading 500 mL" situation in accordance with some embodiments of the present inventive concept(s).

FIGS. 37A through 37D are images illustrating a "pump reading 1000 mL" situation in accordance with some embodiments of the present inventive concept(s).

FIGS. 38A through 38D are averaged speckle images (averaged over a number of frames) for each of the four flow cases illustrated in FIGS. 33 through 37 in accordance with some embodiments of the present inventive concept(s).

FIGS. 43A through 43D are images illustrating a "pump reading 0 mL" situation in accordance with some embodiments of the present inventive concept(s).

FIGS. 50A and 50B are images illustrating a single laser speckle imaging (LSI) image and a inverse laser speckle temporal contrast imaging (LSCTI) image, respectively, in accordance with some embodiments of the present inventive concept.

FIGS. 58A through 58C are images illustrating a single LSI image, an LSSCI image and an LSCTI image, respectively, of a beating human heart at end diastole in accordance with some embodiments of the present inventive concept.

FIG. 58D is a graph of average intensity vs. time illustrating an instantaneous flow measurement of the beating heart in FIGS. 58A through 58C in accordance with some embodiments of the present inventive concept.

FIGS. 61A through 61C are images illustrating a single. LSI image, an LSSCI image and an LSCTI image, respectively, of a beating human heart at diastole in accordance with some embodiments of the present inventive concept.

FIG. 61D is a graph of average intensity vs. time illustrating an average flow measurement of the beating heart in FIGS. 61A through 61C in accordance with some embodiments of the present inventive concept.

FIGS. 62A through 62C are images illustrating a single LSI image, an LSSCI image and an LSCTI image, respectively, of a beating human heart at systole in accordance with some embodiments of the present inventive concept.

FIG. 62D is a graph of average intensity vs. time illustrating an average flow measurement of the beating heart in FIGS. 62A through 62C in accordance with some embodiments of the present inventive concept.

FIGS. 63A through 63C are images illustrating a single LSI image, an LSSCI image and an LSCTI image, respectively, of a beating human heart including a bypass graft that has been clamped in accordance with some embodiments of the present inventive concept.

FIG. 63D is a graph of average intensity vs. time of the beating heart in FIGS. 63A through 63C in accordance with some embodiments of the present inventive concept.

DETAILED DESCRIPTION OF EMBODIMENTS

Figure 1:
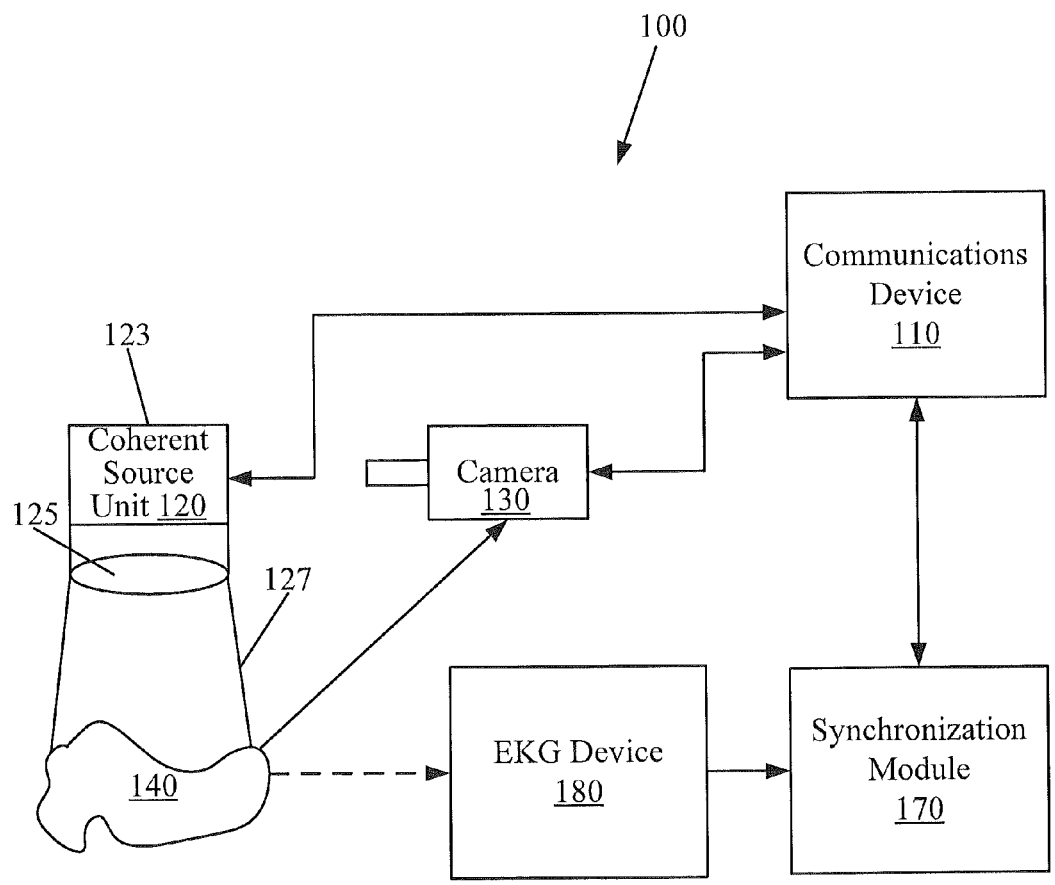
FIG. 1 is a block diagram of a non-invasive system for measuring blood flow in principal vessels of a subject in accordance with some embodiments of the present inventive concept(s).

Embodiments of the present inventive concept will now be described more fully hereinafter with reference to the accompanying figures, in which preferred embodiments of the inventive concept are shown. This inventive concept may, however, be embodied in many different forms and should not be construed as limited to the embodiments set forth herein. Like numbers refer to like elements throughout. In the figures, layers, regions, elements or components may be exaggerated for clarity. Broken lines illustrate optional features or operations unless specified otherwise.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the inventive concept. The sequence of operations (or steps) is not limited to the order presented in the claims or figures unless specifically indicated otherwise.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

As will be appreciated by one of skill in the art, embodiments of the present inventive concept may be embodied as a method, system, data processing system, or computer program product. Accordingly, the present inventive concept may take the form of an embodiment combining software and hardware aspects, all generally referred to herein as a "circuit" or "module." Furthermore, the present inventive concept may take the form of a computer program product on a non-transitory computer usable storage medium having computer-usable program code embodied in the medium. Any suitable computer readable medium may be utilized including hard disks, CD-ROMs, optical storage devices, or other electronic storage devices.

Computer program code for carrying out operations of the present inventive concept may be written in an object oriented programming language such as Matlab, Mathematica, Java, Smalltalk, C or C++. However, the computer program code for carrying out operations of the present inventive concept may also be written in conventional procedural programming languages, such as the "C" programming language or in a visually oriented programming environment, such as Visual Basic.

Certain of the program code may execute entirely on one or more of a user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The inventive concept is described in part below with reference to flowchart illustrations and/or block diagrams of methods, devices, systems, computer program products and data and/or system architecture structures according to embodiments of the inventive concept. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

As discussed above, there is a need for effective non-invasive methods for determining blood flow distribution. It is believed that none of the existing methods offer a fully non-invasive cost effective solution to the problem of flow speed determination. Accordingly, some embodiments of the inventive concept provide methods, systems and computer program products for determining speed distribution of blood flow without requiring the use of dye injection, contrast agent or a contact probe. Some embodiments of the inventive concept use speckle imaging techniques to determine blood flow distribution. As used herein, a "speckle" image acquisition refers to the recording of elastically scattered light, i.e. the scattered light has a wavelength that is the same as the incident light, from an object illuminated by a coherent light such as the output from a coherent light source. In particular, the "speckle" is actually a diffraction pattern, which is highly correlated to the morphology of the object being imaged. If certain parts of the object are in translational motion, i.e. blood stream flowing in a coronary artery, the corresponding part or pixels of the speckle image will vary with time in fashions different from those parts not undergoing such translational motion. This difference in the temporal variation of pixel intensity in the speckle image provides a mechanism to non-invasively measure flow speed (m/s or cm/min) in principal vessels. With knowledge of the diameters of the principal vessels that can be determined from the same set of acquired speckle images, the blood flow rate (ml/min) within FOV may be determined. The combined information of blood flow rates and their distribution in different vessels provide critical data for evaluating the effectiveness of Coronary artery bypass grafting (CABG) and other surgical procedures in improving patients' revascularization status and clinical prognosis. Speckle image acquisition is generally discussed, for example, in *Velocity measurement of a diffuse object by using a time-varying speckle* by Ohtsubo et al.

Thus, some embodiments of the present inventive concept provide a non-invasive technique for measuring blood flow that provides the ability to quantitatively measure blood flow in principal vessels and perfusion distribution in areas perfused by one or more of those principal vessels as will be discussed further below with respect to FIGS. 1 through 44.

Furthermore, the data acquired from the obtained set of speckle images can be verified using flow hemodynamic modeling in accordance with some embodiments of the present inventive concept. In particular, using the Navier-Stokes equation, which provides the governing equation for fluid dynamics, a velocity field associated with the FOV (in the principal vessels) can be obtains. As used herein, "velocity field" refers to a distribution of fluid velocity in space and time. This velocity field may then be used to calculate flow rate as well as other quantities of interest, such as pressure. These quantities of interest, for example, flow rates, can then be compared with the experimental data calculated using the obtained set of speckle images. Thus, the hemodynamic modeling may be used to validate the experimental data as well as the success of the procedure as will be discuss further below with respect to FIGS. 45 through 48.

Referring first to FIG. 1, a non-invasive system for measuring blood flow in principal vessels of a subject in accordance with some embodiments of the present inventive concept will be discussed. As discussed above, "non-invasive" refers to a system or method that does not require the subject to be injected with a dye, penetrated with an object or touched with an intrabody probe or probes. Thus, as used herein, the term non-invasive refers to a system or method that makes minimal contact with the subject. As used herein, "subject" refers to the person or thing being imaged. It will be understood that although embodiments of the present inventive concept are discussed herein with respect to measuring blood flow in principal vessels of the subject, embodiments of the present inventive concept are not limited to this configuration. The subject can be any subject, including a veterinary, cadaver study or human subject. As used herein, "perfusion" refers to blood flow at the tissue perfusion distribution level detected with speckle imaging.

As illustrated in FIG. 1, the system 100 includes a communications device 110, a coherent light source unit 120, a camera 130, a synchronization module 170 and an EKG device 180. Although the system of FIG. 1 is depicted as only including these elements, it will be understood that other elements may also be present in the system without departing from the scope of the present inventive concept. For example, the systems illustrated in the photographs of FIGS. 5 and 21 include additional elements not present in the system illustrated in FIG. 1.

Referring again to FIG. 1, in some embodiments, the coherent light source unit 120 may be a laser unit, which may include a laser 123 and a beam shaping lens 125. The laser unit 120 may provide a coherent light source that illuminates a region of interest 140. The coherent light source provided by the laser unit 120 may have a wavelength of from about 600 nm to about 1100 nm. As used herein, the "region of interest" refers to the region of the subject that is being imaged, for example, the principal vessels and tissue, organs, etc. to determine blood flow therein. Although embodiments of the present inventive concept are discussed primarily herein with respect to blood flow distribution in the principal vessels, embodiments of the present inventive concept are not limited to this configuration. For example, blood flow in organs may be determined without departing from the scope of the present inventive concept.

The laser unit 120 may have light output at a fixed or variable wavelength of from about 600 nm to about 1100 nm without departing from the scope of the present inventive concept. The laser 120 can be configured to illuminate the region of interest 140 with a laser beam 127 having substantially constant intensity within FOV of an imaging unit. In some embodiments, the constant or near constant intensity of the laser beam can facilitate acquiring speckle images with a high signal-to-noise (SNR) ratio. The laser 120 can be a low power continuous-wave laser. Thus, the subject does not need to wear any protective apparatus, for example, clothing or goggles, to shield the subject from potential adverse effects of the laser. In some embodiments, for example, the laser 120 may be of 633 nm in wavelength and 1 mW in power.

Use of a laser or other coherent light source having a wavelength of from about 600 nm to about 1100 nm allows relatively deep penetration of light into tissue and can provide an accurate determination of blood flow speed in the principal vessels and the perfusion distribution as will be discussed further below.

In some embodiments, the laser unit 120 may be used to illuminate the coronary artery and be triggered by the electrocardiogram (EKG) provided by EKG device 180 through the synchronization module 170 and measurements can be taken from the same point outside the heart and the same point on the heart itself. In other words, the FOV is fixed by two parameters, the point on the heart and the distance from the camera outside the heart. The FOV is kept the same so that the synchronization can be performed.

Referring again to FIG. 1, the camera 130 communicates with the laser unit 120 and the communications device 110.

The camera 130 is configured to sequentially acquire at least two speckle images of the region of interest during a fixed time period. The faster the camera 130, the shorter the fixed time period has to be for acquiring the same number of speckle images. In some embodiments, the camera 130 may be a CCD camera, for example, a Lumenera Lm075 or similar devices.

As used herein, the fixed time period is typically short enough to reduce or possibly minimize motion effects, but long enough to obtain sufficient light signals. Several examples of this fixed time period are discussed throughout the specification, for example, the fixed time period may be from about 1.0 to about 200 ms, or within a single EKG cardiac cycle. However, it will be understood that the fixed time period is not limited to the specific time periods discussed herein. For example, the fixed time period may be greater than a single EKG cardiac cycle without departing from embodiments discussed herein.

The camera 130 may be configured to acquire from about 50 to about 1000 speckle images during the fixed time period. In some embodiments, the camera may only need to acquire from about 50 to about 500 speckle images to provide a meaningful result. The fixed time period may be selected based on data associated with in situ determined blood flow speed. In some embodiments, the fixed time period is relatively short, typically less than 1 second, or from about 1.0 ms to about 200 ms.

The acquisition of the speckle images can be synchronized with the motion of the heart of the subject. For example, in some embodiments, acquisition of the speckle images may be synchronized with the EKG of the subject such that the motion of the heart will have minimal effect on determination of blood flow speed. Thus, the fixed time period would be located within a single EKG cardiac cycle.

Referring again to FIG. 1, the communications device 110 is configured to process the at least two acquired speckle images based on temporal variation of pixel intensities among the acquired speckle images to determine spatial distribution of blood flow speed in the principal vessels and perfusion distribution in tissue in the region of interest. The at least two acquired speckle images can be electronically evaluated and/or processed using an image processing algorithm that combines temporal and spatial calculations of the at least two acquired speckle images. The at least two acquired speckle images have a direct relationship to the blood flow speed in the principal vessels and the perfusion distribution.

In particular, some embodiments of the present inventive concept use speckle imaging techniques to yield blood flow speed in the principal vessels and perfusion distribution over the FOV. As used herein, FOV refers to the area of the imaged object that can be viewed by the imaging sensor. Due to the coherence among the scattered light from different parts of the illuminated region of the imaged object, the intensity of the scattered light arriving at a detecting element of an imaging sensor depends on the relative spatial relation among the different parts. The dependency leads to a "speckle" appearance of the acquired image since intensity of scattered light having an optical wavelength of from about 200 nm to about 2000 nm can vary quickly over a small spatial domain with a size of about 10 cm. These concepts will be discussed further below.

Figure 2A:
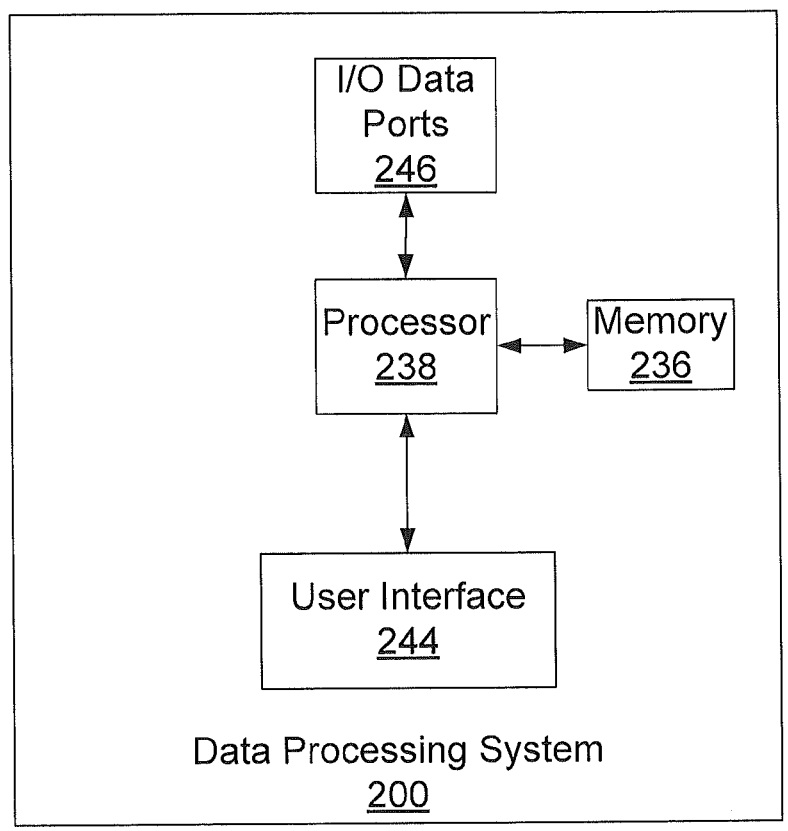
FIG. 2A is a block diagram of a data processing system according to embodiments of the present inventive concept(s).
Figure 2B:
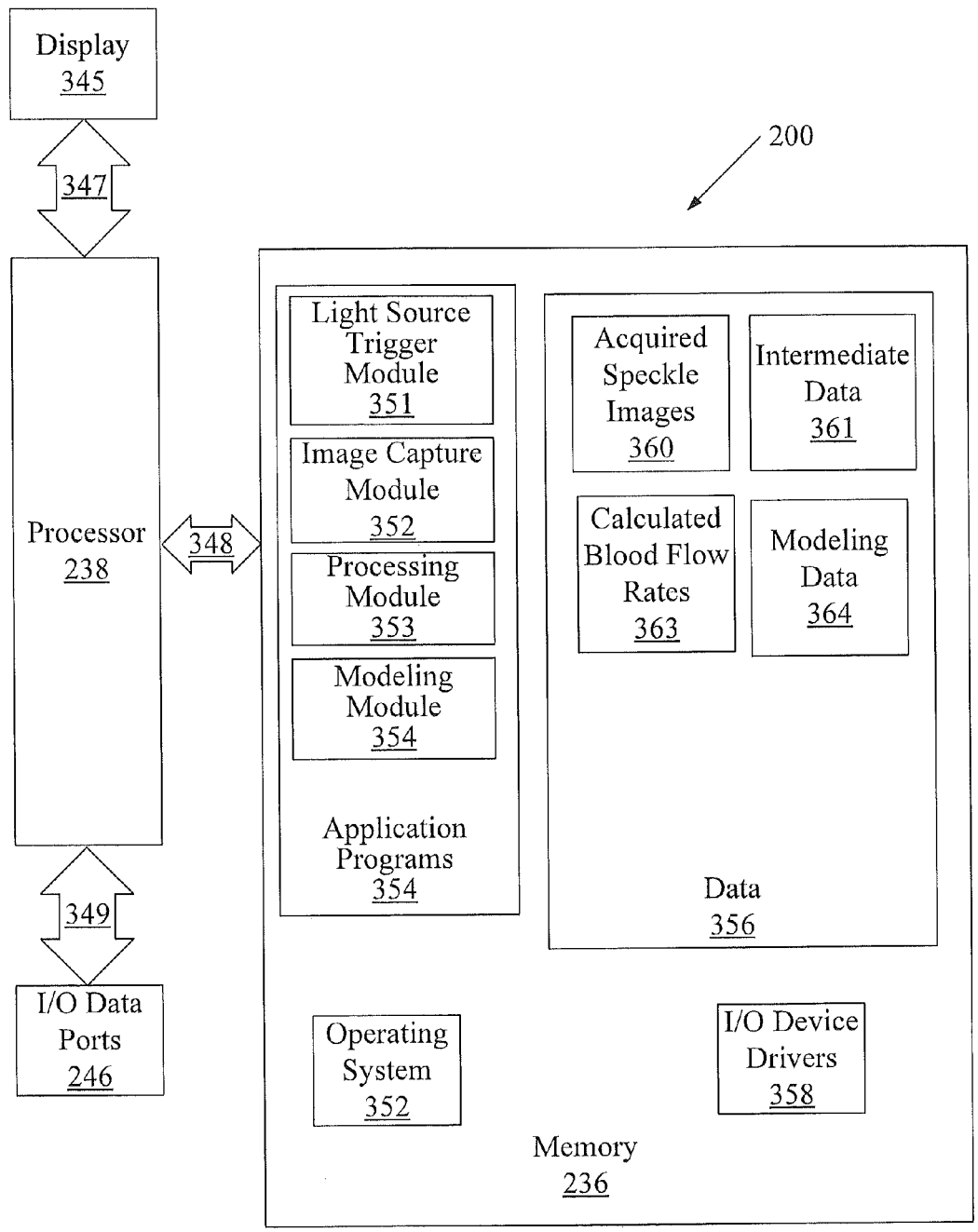
FIG. 2B is a more detailed block diagram of the data processing system illustrated in FIG. 2 in accordance with some embodiments of the present inventive concept(s).

Referring now to FIGS. 2A and 2B, a data processing system 200 that may be used in the system 100 illustrated in FIG. 1 in accordance with some embodiments of the inventive concept will be discussed. The data processing system 200 may be included in the communications device 110, the camera 130 or split between various elements of the system 100 without departing from the scope of the present inventive concept. As illustrated in FIG. 2, an exemplary embodiment of a data processing system 200 suitable for use in the system 100 of FIG. 1 includes a user interface 244 such as a keyboard, keypad, touchpad or the like, I/O data ports 246 and a memory 236 that communicates with a processor 238. The I/O data ports 246 can be used to transfer information between the data processing system 200 and another computer system or a network. These components may be conventional components, such as those used in many conventional data processing systems, which may be configured to operate as described herein.

Referring now to FIG. 2B, a more detailed block diagram of the data processing system 200 in accordance with some embodiments of the present inventive concept will be discussed. The processor 238 communicates with a display 345 via and address/data bus 347, the memory 236 via an address/data bus 348 and the I/O data ports 246 via an address/date bus 349. The processor 238 can be any commercially available or custom microprocessor or ASICs. The memory 236 is representative of the overall hierarchy of memory devices containing the software and data used to implement the functionality of the data processing system 200. The memory 236 can include, but is not limited to, the following types of devices: cache, ROM, PROM, EPROM, EEPROM, flash memory, SRAM, and DRAM.

As shown in FIG. 2B, the memory 236 may include several categories of software and data used in the data processing system 200: an operating system 352; application programs 354; input/output (I/O) device drivers 358; and data 356. As will be appreciated by those of skill in the art, the operating system 352 may be any operating system suitable for use with a data processing system, such as OS/2, AIX or zOS from International Business Machines Corporation, Armonk, N.Y., Windows95, Windows98, Windows2000, WindowsXP, or Vista from Microsoft Corporation, Redmond, Wash., Unix, Linux, LabView, or a real-time operating system such as QNX or VxWorks, or the like. The I/O device drivers 358 typically include software routines accessed through the operating system 352 by the application programs 354 to communicate with devices such as the I/O data port(s) 246 and certain memory 236 components. The application programs 354 are illustrative of the programs that implement the various features of the data processing system 200 included a system in accordance with some embodiments of the present inventive concept and preferably include at least one application that supports operations according to some embodiments of the present inventive concept. Finally, the data 356 represents the static and dynamic data used by the application programs 354, the operating system 352, the I/O device drivers 358, and other software programs that may reside in the memory 236.

As illustrated in FIG. 2B, the data 356 according to some embodiments of the present inventive concept may include acquired speckle images 360, intermediate data 361, calculated blood flow rates 363 and modeling data 364. Although the data 356 illustrated in FIG. 2B includes three different files 360, 361, 363 and 364, embodiments of the present inventive concept are not limited to this configuration. Two or more files may be combined to make a single file; a single file may be split into two or more files and the like without departing from the scope of the present inventive concept.

As further illustrated in FIG. 2B, the application programs 354 may include a light source trigger module 351, an image capture module 352, a processing module 353 and a modeling module 354 in accordance with some embodiments of the inventive concept. While the present inventive concept is illustrated, for example, with reference to the light source trigger module 351, the image capture module 352, the processing module 353 and the modeling module 354 being application programs in FIG. 2B, as will be appreciated by those of skill in the art, other configurations may also be utilized while still benefiting from the teachings of the present inventive concept. For example, the light source trigger module 351, the image capture module 352 the processing module 353 and the modeling module 354 may also be incorporated into the operating system 352 or other such logical division of the data processing system 300. Thus, the present inventive concept should not be construed as limited to the configuration of FIG. 2B, but is intended to encompass any configuration capable of carrying out the operations described herein.

Furthermore, while the light source trigger module 351, the image capture module 352 the processing module 353 and the modeling module 354 are illustrated in a single data processing system, as will be appreciated by those of skill in the art, such functionality may be distributed across one or more data processing systems. Thus, the present inventive concept should not be construed as limited to the configuration illustrated in FIGS. 2A and 2B, but may be provided by other arrangements and/or divisions of function between data processing systems.

In particular, the light source trigger module 351 may be configured to illuminate a region of interest with a coherent light source. The coherent light source may have a wavelength of from about 600 nm to about 1100 nm as discussed above. The image capture module 352 may be configured to sequentially acquire at least two speckle images of the region of interest during a fixed time period. The processing module 353 may be configured to process the at least two acquired speckle images based on a diffraction pattern of each the at least two speckle images to determine spatial distribution of blood flow speed in the principal vessels and perfusion distribution in tissue in the region of interest.

The modeling module 354 may be configured to calculate a velocity field for the region of interest; calculate blood flow speed in the region of interest based on the calculated velocity field; and compare the calculated blood flow in the region of interest to the blood flow speed determined using the acquired at least two speckle images of the region of interest to verify results obtained using the at least two speckle images. In some embodiments, the modeling module 354 is configured to calculate the velocity field using Equations 9 and 10 set out below.

Thus, blood flow speed as well as other quantities may be calculated using both the speckle method and the velocity field method before a procedure is performed on a subject and after a procedure is performed on the subject to verify that the procedure was successful. By comparing the measurements/quantities before and after the procedure, the success of the procedure may be determined, which will be discussed further below.

Figure 3:
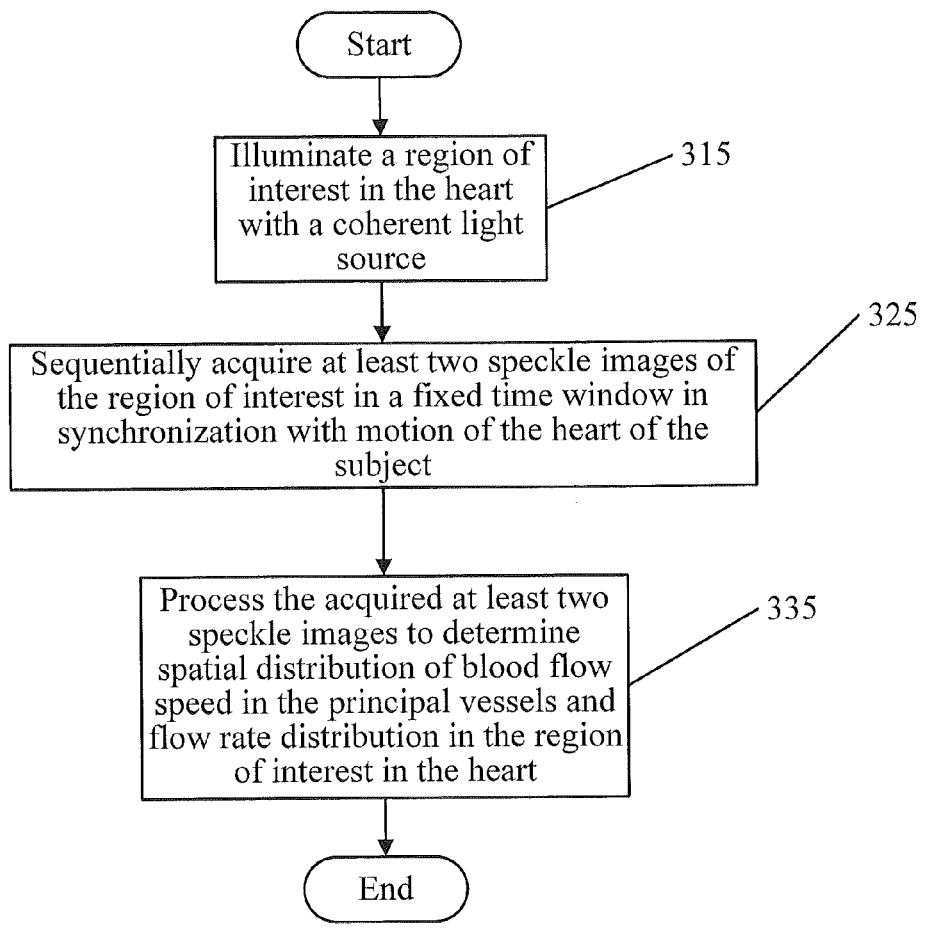
FIGS. 3 and 4 are flowcharts illustrating operations for measuring blood flow in principal vessels in accordance with various embodiments of the present inventive concept(s).

Referring now to the flowcharts of FIGS. 3 and 4, operations of a non-invasive method for measuring blood flow in principal vessels of a subject will be discussed. As illustrated in FIG. 3, operations begin at block 315 by illuminating a region of interest in the heart with a coherent light source. The coherent light source may have a wavelength of from about 600 nm to about 1100 nm. Providing a coherent light source with a wavelength of from about 600 nm to about 1100 nm may allow for non-invasive, deep penetration of light into tissues and provides an accurate determination of blood flow speed in the principal vessels and the perfusion distribution within the layer of light penetration.

In some embodiments, the coherent light source may be provided by a laser configured to illuminate the region of interest. The laser may have a fixed or variable wavelength. The laser may produce a beam having substantially constant intensity within a FOV of an imaging unit. The laser may be a low energy and continuous-wave laser such that the subject does not require any protective apparatus to shield the subject from effects of the laser.

Referring again to FIG. 3, operations continue at block 325 by sequentially acquiring at least two speckle images of the region of interest during a fixed time period. The fixed time period may be selected based on data associated with in situ determined blood flow speed. In some embodiments, the at least two speckle images may be acquired in synchronization with motion of a heart of the subject such that the motion of the heart will have minimal effect on determination of blood flow speed using the acquired at least two speckle images. For example, the fixed time period can correspond to a single EKG cardiac cycle or defined portion thereof cycle.

The camera may be configured to acquire the at least two speckle images during the fixed time period. In some embodiments, from about 50 to about 1000 speckle images may be acquired using the camera during the fixed time period of from about 1 ms to about 200 ms. In some embodiments, about 200 to about 500 speckle images may be acquired. Higher numbers of speckle images typically allow better signal-to-noise ratios in the calculated LSCI image but take longer time to acquire.

Referring again to FIG. 3, operations continue at block 335 by electronically processing the acquired speckle images based on the temporal variation of the pixel intensities in the acquired speckle images to generate a laser speckle contrast imaging (LSCI) image and determine spatial distribution of blood flow speed in the principal vessels and perfusion distribution in tissue in the region of interest from the LSCI image.

In some embodiments, electronically evaluating speckle image data may include electronically evaluating the acquired speckle images using an image processing algorithm that combines temporal and spatial calculations of the acquired speckle images to generate a LSCI image and determine spatial distribution of blood flow speed. The at least two speckle images may have a direct relationship to the blood flow speed in the principal vessels and the perfusion distribution which are utilized in generating an LSCI image for determination of the spatial distribution of blood flow speed. For example, following equations can be used to obtain the intensity at each pixel of the LSCI image K (i, j) from the acquired speckle image set $\{I_n\}$ with n=1, 2, . . . , N, i.e., $$K(i, j) = \frac{\sigma(i, j)}{\mu(i, j)}, \quad \text{Equation (1)}$$

where $$\mu(i, j) = \frac{1}{N}\sum_{n=1}^{N} I_n(i, j), \quad \text{Equation (2)}$$

$$\sigma(i, j) = \sqrt{\frac{1}{N}\sum_{n=1}^{N} (I_n(i, j) - \mu(i, j))^2}. \quad \text{Equation (3)}$$

In the above calculations, $I_n(i, j)$ refers to the pixel at (i, j) location in a speckle image acquired at nth time point and N (>1) is the total number of acquired speckle images.

It will be understood that the operations of blocks 315, 325 and 335 may be performed before and after a procedure performed on the subject. The results before and after the procedure may be compared to verify the success of the procedure in the subject.

Figure 4:
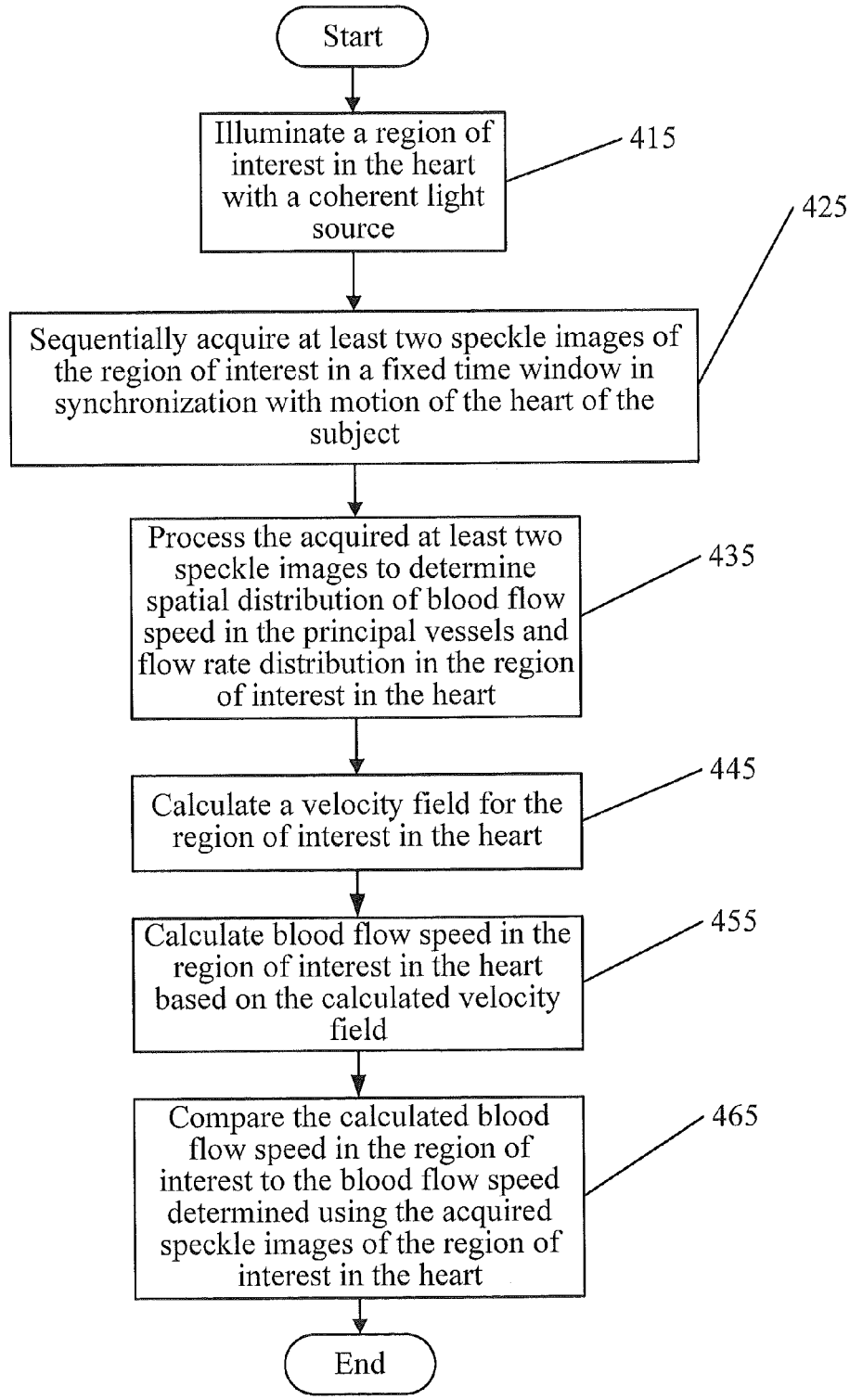

Referring now to FIG. 4, operations for a non-invasive method for measuring blood flow in principal vessels of a subject in accordance with some embodiments will be discussed. Operations begin at block 415 by illuminating a region of interest in the heart with a coherent light source, wherein the coherent light source has a wavelength of from about 600 nm to about 1100 nm. At least two speckle images of the region of interest are sequentially acquired during a fixed time period (block 425) in synchronization with the motion of the heart. Temporal and spatial variation of pixel intensities of the at least two acquired speckle images are electrically evaluated to determine spatial distribution of blood flow speed in the principal vessels and perfusion distribution in tissue in the region of interest of the heart (block 435).

A velocity field for the region of interest in the heart is calculated (block 445). In some embodiments, the velocity field is calculated using equations (9) and (10) set out below. Blood flow speed in the region of interest of the heart based on the calculated velocity field is calculated (block 455). The calculated blood flow speed in the region of interest in the heart is compared to the blood flow speed determined using the acquired at least two speckle images of the region of interest to verify results obtained using the at least two speckle images (block 465). Thus, embodiments of the present inventive concept may be used to verify experimental results as will be discussed further below.

It will be understood that the operations of blocks 415, 425, 435, 445, 455 and 465 may be performed before and after a procedure performed on the subject. The results before and after the procedure may be compared to verify the success of the procedure in the subject.

The following non-limiting examples are provided by way of example.

EXAMPLES

Figure 5:
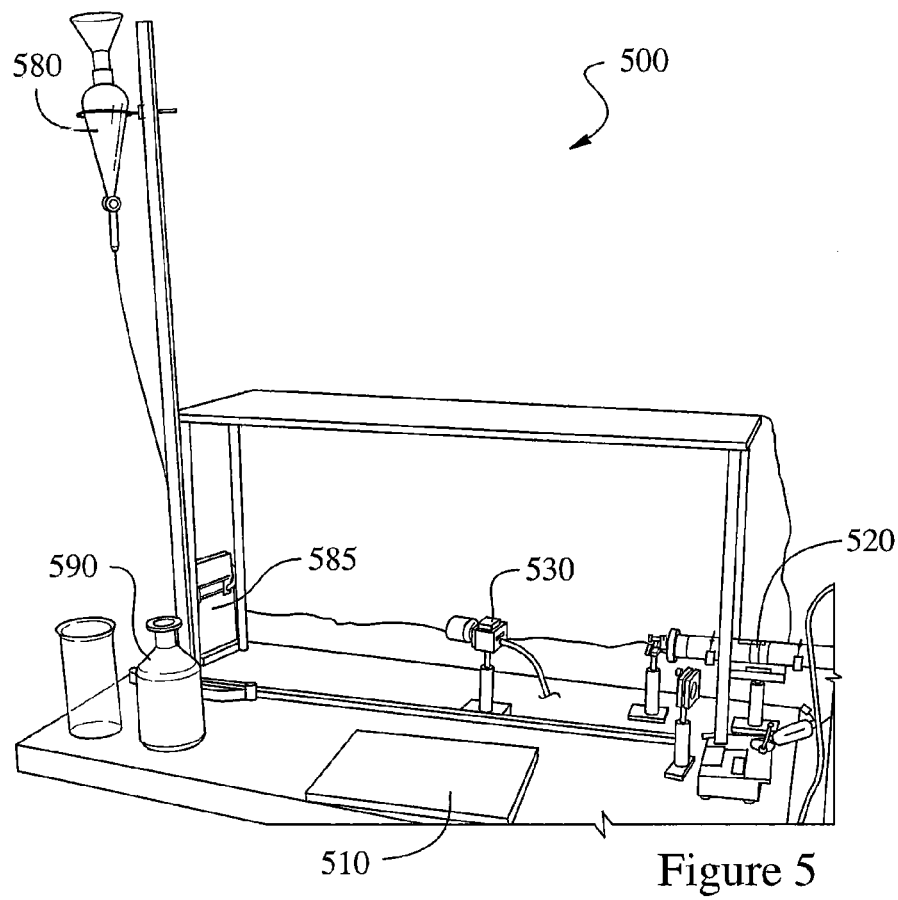
FIG. 5 is a digital photograph of a system for measuring flow of blood phantom used in an experiment performed in accordance with some embodiments of the present inventive concept(s).

Referring to FIG. 5, a digital photograph of a prototype system 500 to detect flow speed using laser speckle contrast imaging (LSCI) technology in accordance with some embodiments of the present inventive concept will be discussed. As illustrated in FIG. 5, the system includes a communication device 510, such as a laptop computer, a laser unit 520 including a laser generator and a focusing lens, a camera 530, a flow generator 580, flow liquid 590 and a flow target 585. Table 1 set out below summarizes the actual equipment/devices used in this experiment.

TABLE 1

| Devices used in Experiment 1 | Notes |
|---|---|
| CCD camera (530) | Lumenera Lm075 |
| Laser (520) | 633 nm in wavelength, 1 mW in power |
| Liquid used in flow (590) | 20% Intralipid 1 to 4 ratio mixed with water plus fruit color |
| Computer/Communications Device (510) | Laptop PC |

As discussed above, the faster the camera 530, the smaller the fixed time period has to be to obtain an adequate number of speckle images to provide a meaningful result. Thus, the limitation of the frame rate of the camera 530 in the prototype system may have impacted the final result of this experiment. The laser 520 is a low power continuous-wave laser providing a single-wavelength coherent light source. Thus, the subject of the imaging does not typically require any protection from such a laser, such as protective clothing or eyewear. The laser 520 produces a beam having a wavelength of from about 600 nm to about 1100 nm in some embodiments. During the experiment, the laser beam produced by the laser 520 is used to illuminate the region of interest with substantially constant intensity with the FOV of the imaging unit. This is an important aspect of the experiment because it allows the resulting images to have a high SNR.

Colored intralipid was used as the flow liquid 590 during the experiment due to the fact that a light scattering characteristics of the colored intralipid is similar to those of mammalian blood. Thus, the colored intralipid mimics the blood flowing in the human body. The communications device 510 used was a laptop computer, although embodiments of the present inventive concept are not limited to the use of a laptop computer. The acquired speckle images are provided to the communications device 510 and are used to calculate blood flow in according with some embodiments of the present inventive concept. As discussed above, the data is calculated using an image processing algorithm that combines temporal and spatial calculations of the acquired speckle images. Thus, spatial distribution of blood flow speed in principal vessels and perfusion distribution can be determined.

Figure 6:
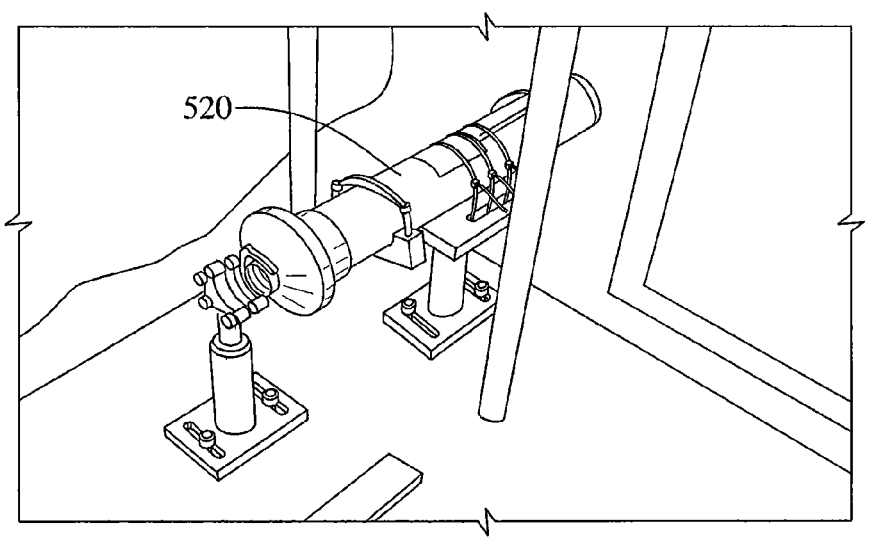
FIGS. 6 through 9 are close up digital photographs of certain elements in the system illustrated in FIG. 5 in accordance with some embodiments of the present inventive concept(s).
Figure 7:
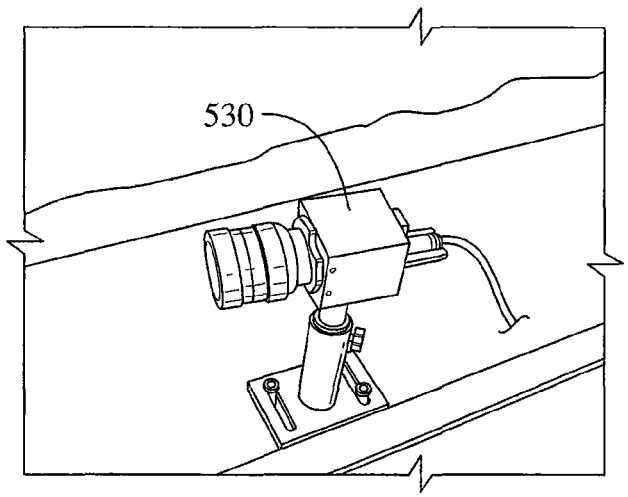
Figure 8:
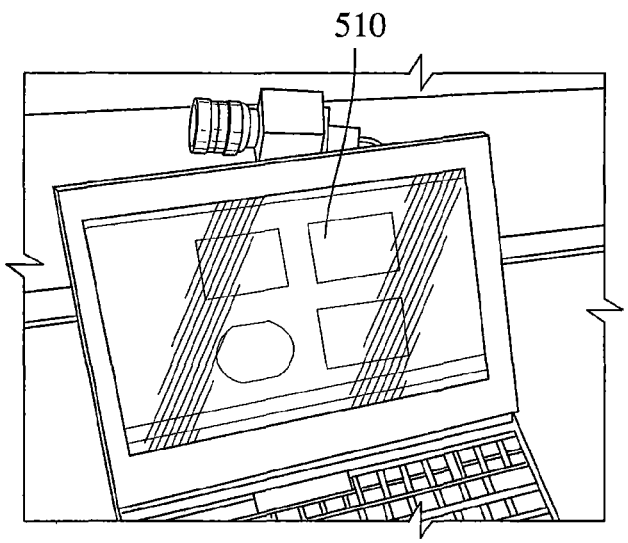
Figure 9:
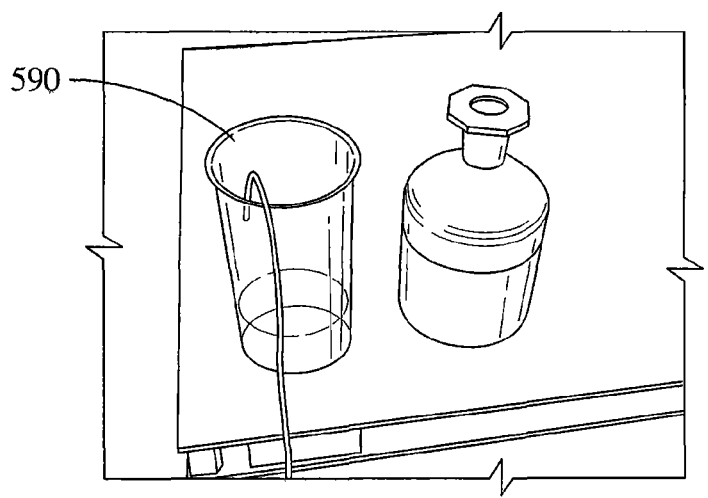

Referring now to FIGS. 6 through 9, close up photographs of the devices illustrated in FIG. 5 used during the first experiment are provided. In particular, FIG. 6 is a close up photograph of the laser unit 520; FIG. 7 is a close up photograph of the camera 530; FIG. 8 is a close up photograph of the communications device 510; and FIG. 9 is a close of the flow liquid 590.

Table 2 set out below summarizes parameters for the camera 530 used during the first experiment. The parameters are for the camera 530 while the image sequence is acquired.

TABLE 2

| Length of image sequence | ~1 second |
| --- | --- |
| Frame rate | ~95 frames/second |
| Image resolution | 320 * 240 pixels |
| Exposure time per frame | 3 ms |
| Gain | 1 |

The upper limit ($V_{limit}$) of flow that can be detected based on the setup of the first experiment can be summarized by the following equation:

$$V_{limit} = \frac{\Delta L}{10\tau} \qquad \text{Equation (4)}$$

In Equation 1, $\Delta L$ is the diameter of the tube, which was 0.26 cm in the first experiment;

$$\tau = 0.4T = \frac{0.4}{f}$$

is the estimated exposure time, 3.0 ms in the first experiment; and f is the frame rate. Thus, in the first experiment $V_{limit}$ can be roughly estimated at about 9.0 cm/second.

Figure 10:
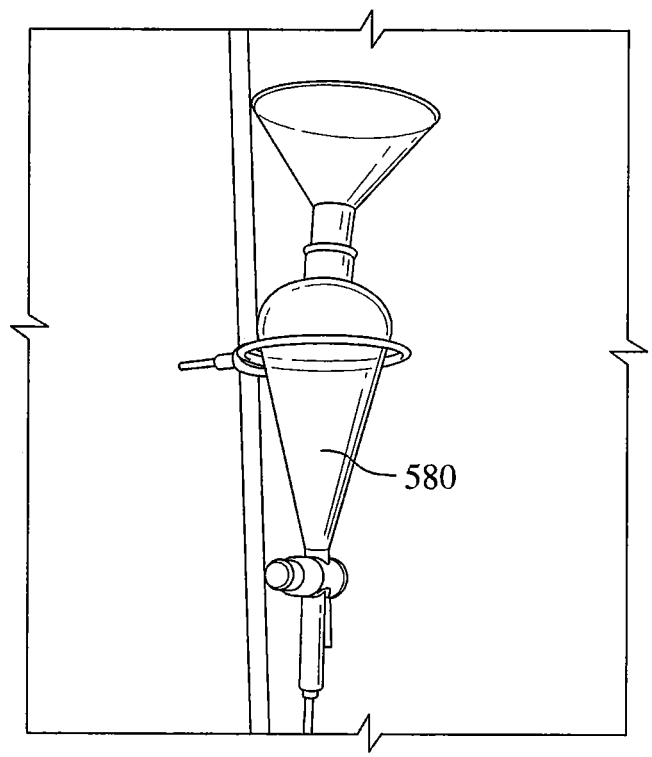
FIGS. 10 and 11 are digital photographs of an exemplary flow generation system used in some embodiments of the present inventive concept(s).
Figure 11:
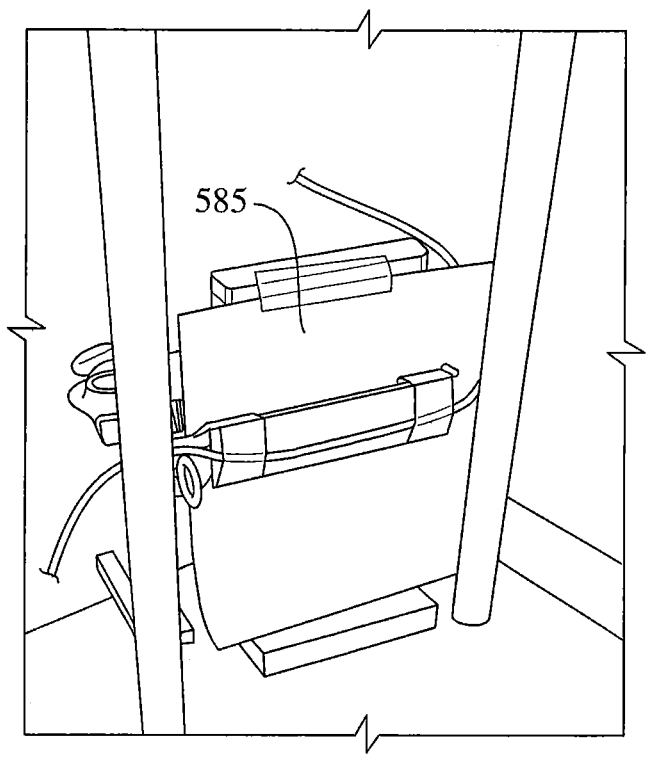

Referring now to FIGS. 10 and 11, photographs of the flow generation system used in the first experiment will be discussed. FIG. 10 illustrates the flow generation system 580. The higher the bottle in the flow generation system 580, the faster the flow of the flow liquid 590. FIG. 11 is a close up photograph of the tube target 585 used as the flow target for the first experiment. Table 3 below summarizes the relationship between the change in height of the bottle and the flow of liquid in the flow generation system in accordance with the first experiment. The change in height is measured from the height of the bottle to the end of the tube.

TABLE 3

| Time (secs) | Volume (cm³) | delta height (cm) | flow rate (cm³/sec) | flow rate (ml/min) | predicted flow rate (ml/min) |
| --- | --- | --- | --- | --- | --- |
| 68 | 100 | 108 | 1.5 | 88.2 | 90.6 |
| 73 | 100 | 98 | 1.4 | 82.2 | 83.0 |
| 80 | 100 | 88 | 1.3 | 75.0 | 75.4 |
| 90 | 100 | 78 | 1.1 | 66.7 | 67.6 |
| 103 | 100 | 68 | 1.0 | 58.3 | 59.8 |
| 120 | 100 | 58 | 0.8 | 50.0 | 51.8 |
| 136 | 100 | 48 | 0.7 | 44.1 | 43.7 |
| 173 | 100 | 38 | 0.6 | 34.7 | 35.4 |

Thus, as illustrated by the delta height (cm) and flow columns of Table 3, the higher the bottle, the faster the flow rate of the colored intralipid liquid.

Figure 12:
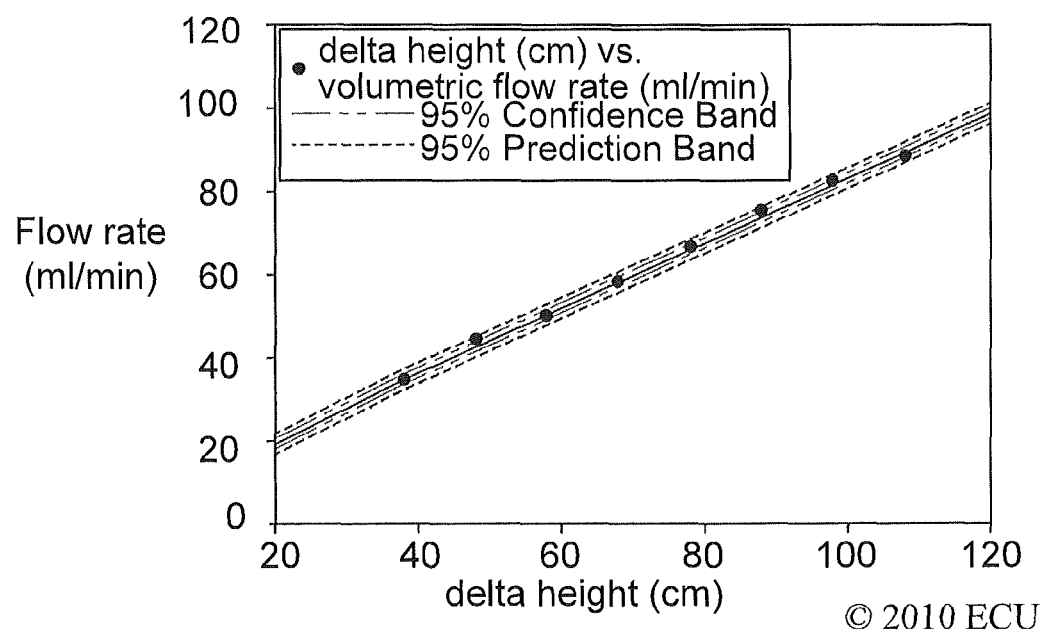
FIG. 12 is a graph illustrating the change in height (cm) vs. flow rate (ml/min) in the flow generation system in accordance with some embodiments of the present inventive concept(s).
Figure 13:
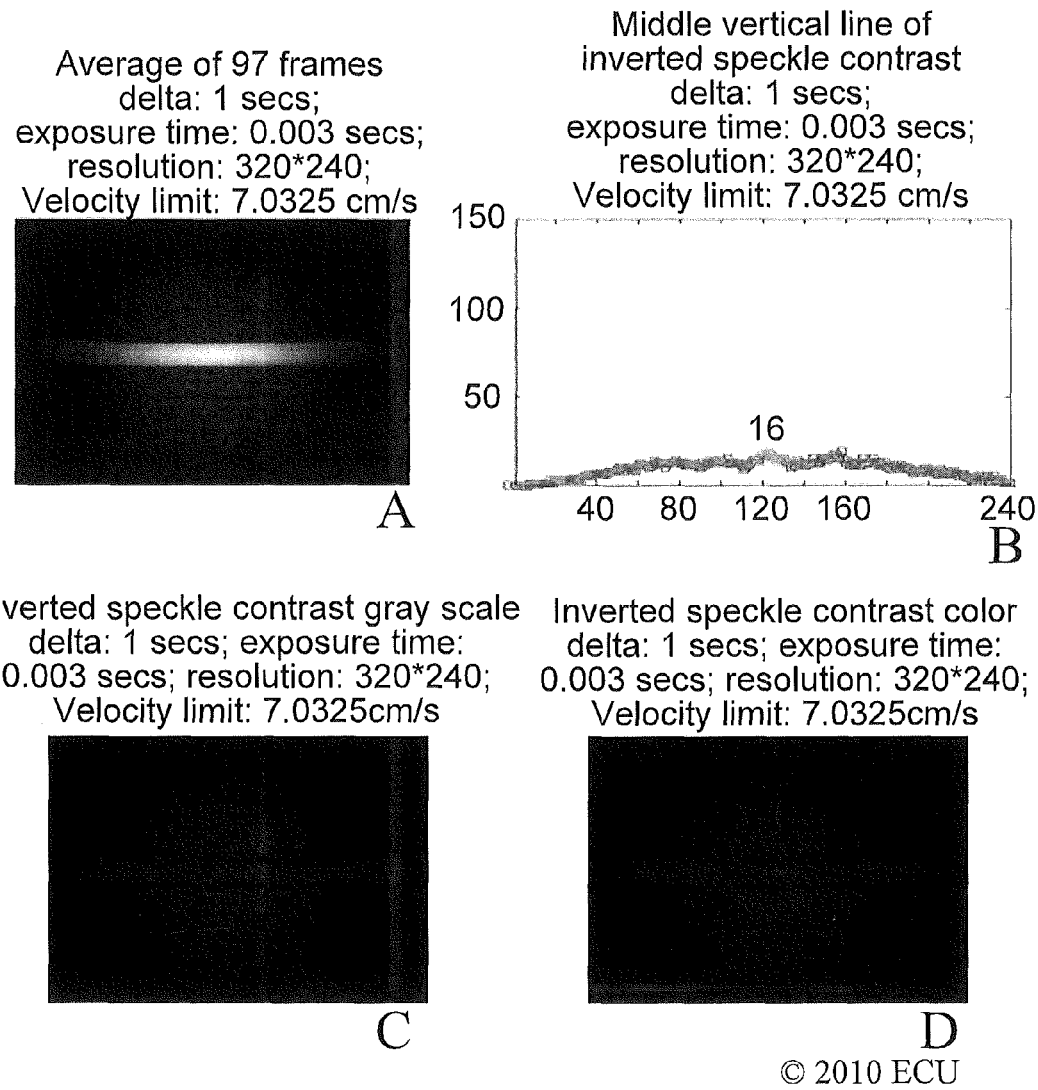
FIGS. 13A through 13D are digital images illustrating a "no flow" case in accordance with some embodiments of the present inventive concept(s).
Figure 15:
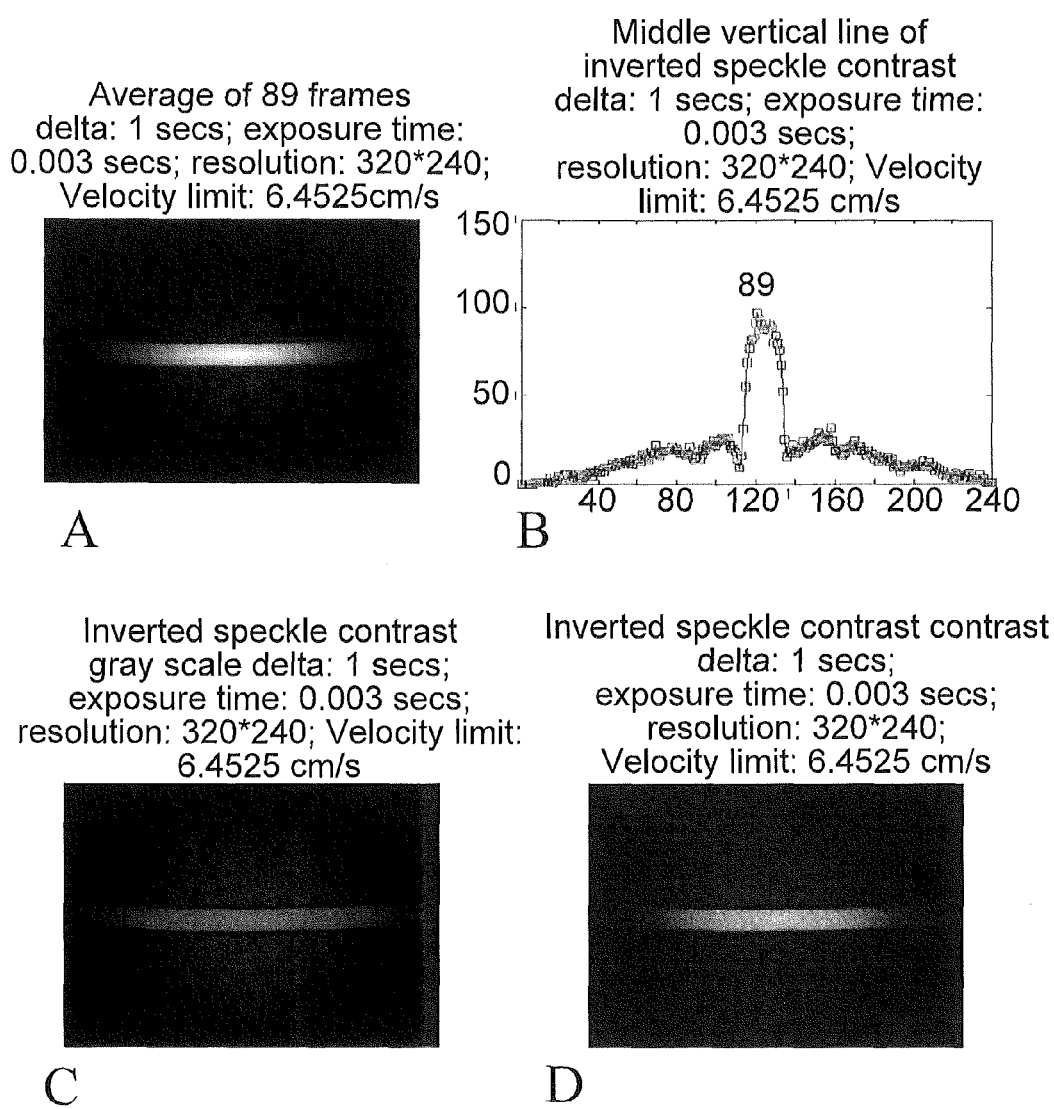
FIGS. 15A through 15D are images illustrating a "flow 2" case in accordance with some embodiments of the present inventive concept(s).
Figure 17:
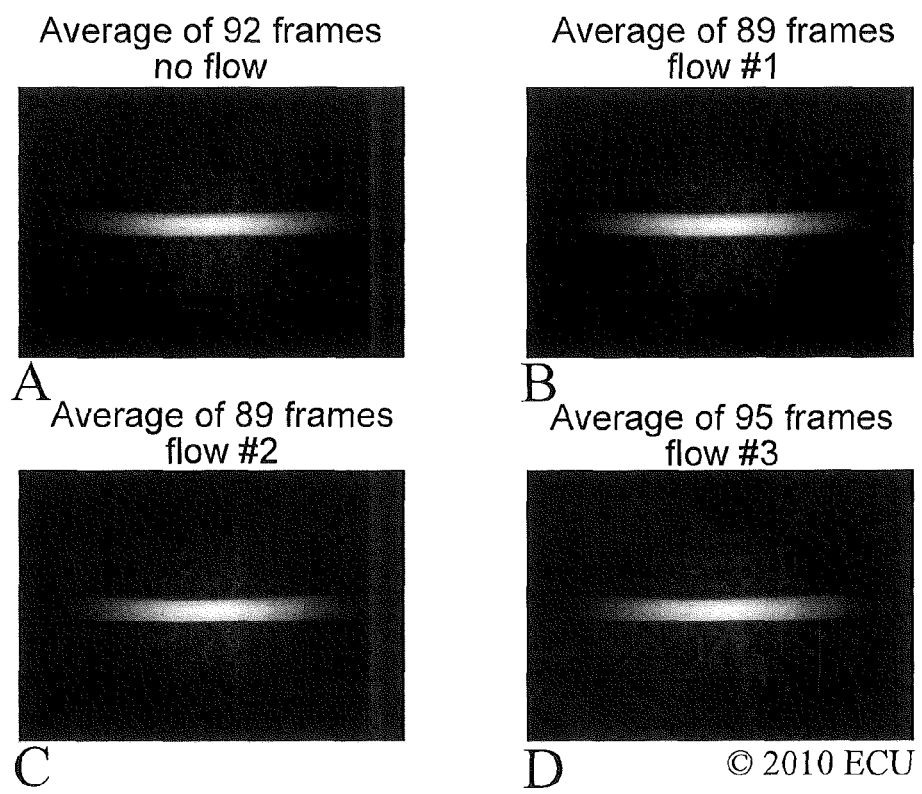
FIGS. 17A through 17D are images (averaged over a number of frames) illustrating a speckle image for each of four flow cases illustrated in FIGS. 13 through 16 in accordance with some embodiments of the present inventive concept(s).
Figure 18:
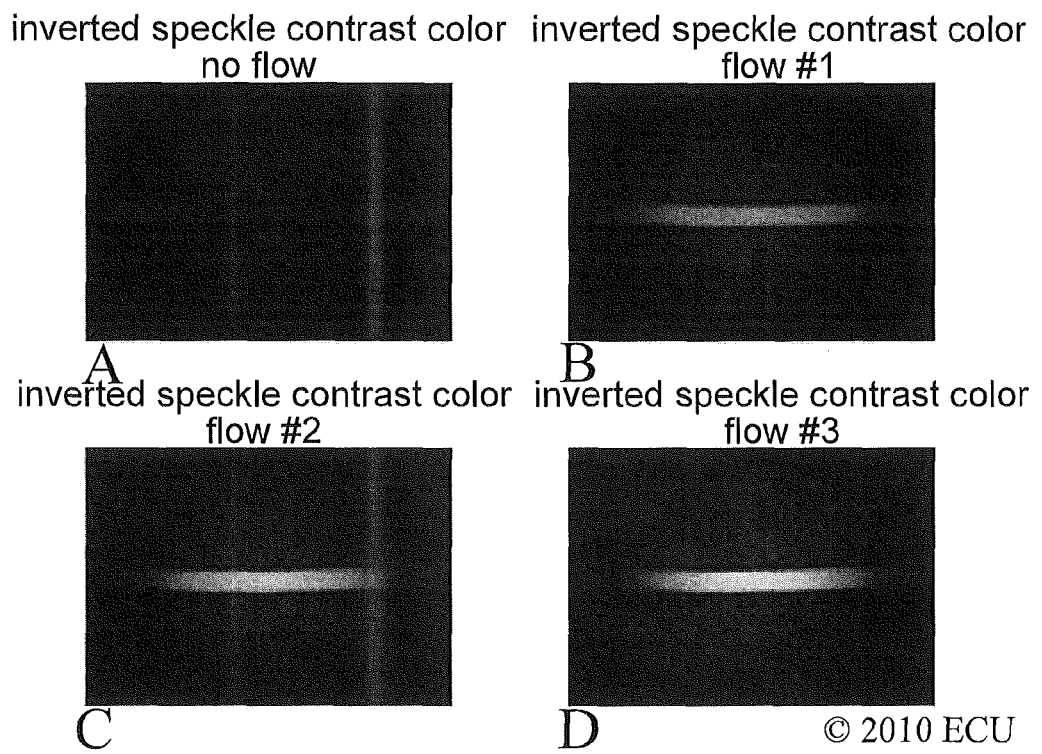
FIGS. 18A through 18D are inverted speckle contrast images illustrating each of the four flow cases illustrated in FIGS. 13 through 16 in accordance with some embodiments of the present inventive concept(s).
Figure 19:
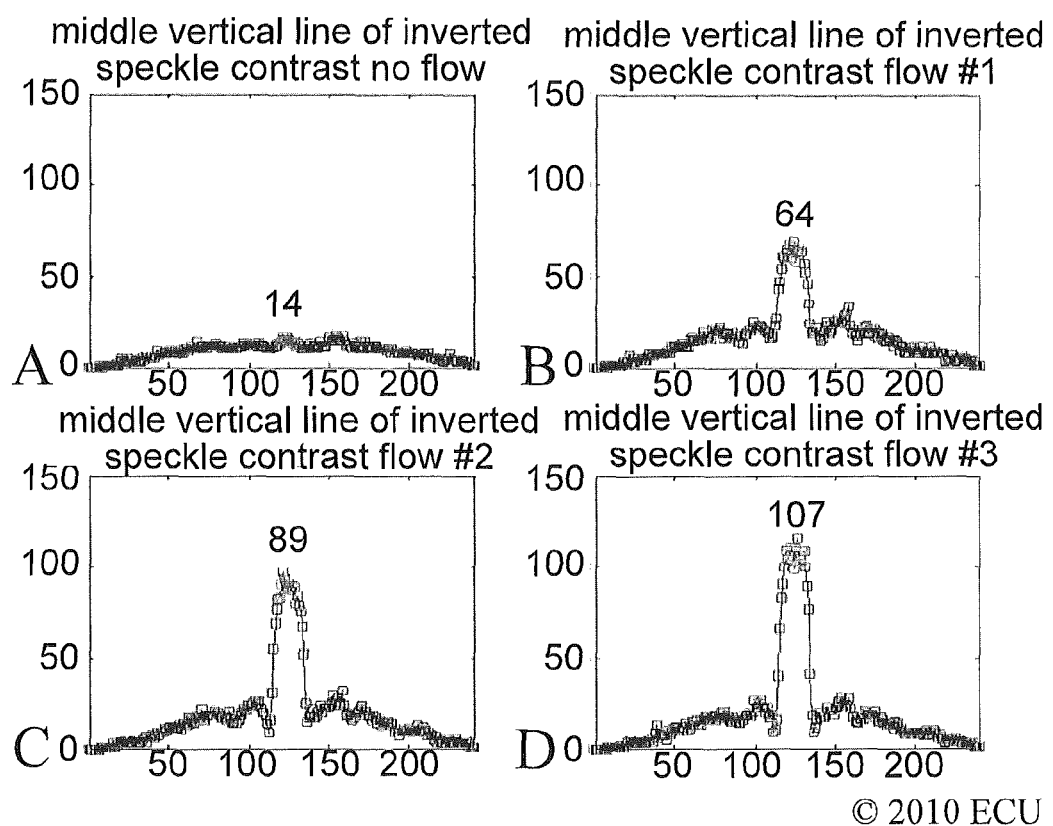
FIGS. 19A through 19D are graphs illustrating a vertical profile of inverted speckle contrast images for each of the four flow cases in FIGS. 13 through 16 in accordance with some embodiments of the present inventive concept(s).

The estimated relationship between delta height (cm) and flow rate (ml/min) is represented by Equation (2) set out below:

$$\text{flow rate} = 1.34 \times \sqrt[0.9]{\Delta h}; \qquad \text{Equation (5)}$$

Where $\Delta h$ is the change in height of the bottle relative to the vertical position of the tube end. FIG. 12 summarizes the data in Table 3 and is a graph illustrating delta height (cm) vs. flow rate (ml/min).

Four cases of flow rate were measured by the LSCI method in the first experiment setup, no flow, flow 1, flow 2 and flow 3. The details of each of the flow rates are summarized in Table 4 set out below. The first experiment was repeated three times for each case to ensure accuracy and repeatability. FIGS. 13A through 13D illustrate resultant images obtained for the "no flow" state. FIG. 13A is an averaged image obtained by averaging in a pixel-to-pixel fashion 97 frames for the "no flow" case; FIG. 13B is a vertical line profile image in the middle of inverted speckle contrast image for the "no flow" case; FIG. 13C is an inverted speckle contrast image for the "no flow" case; and FIG. 13D is a colorized inverted speckle contrast image for the "no flow" case.

FIGS. 14A through 14D illustrate resultant images obtained for the "flow 1" case. FIG. 14A is an averaged image obtained by averaging in a pixel-to-pixel fashion 97 frames for the "flow 1" case; FIG. 14B is a vertical line profile image in the middle of the inverted speckle contrast image for the "flow 1" case; FIG. 14C is an inverted speckle contrast image for the "flow 1" case; and FIG. 14D is a colorized inverted speckle contrast image for the "flow 1" case.

FIGS. 15A through 15D illustrate resultant images obtained for the "flow 2" case. FIG. 15A is an averaged image obtained by averaging in a pixel-to-pixel fashion 89 frames for the "flow 2" case; FIG. 15B is a vertical line profile image in the middle of an inverted speckle contrast image for the "flow 2" case; FIG. 15C is an inverted speckle contrast image for the "flow 2" case; and FIG. 15D is a colorized inverted speckle contrast image for the "flow 2" case.

FIGS. 16A through 16D illustrate resultant images obtained for the "flow 3" case. FIG. 16A is an averaged image obtained by averaging in a pixel-to-pixel fashion 89 frames for the "flow 3" case; FIG. 16B is a vertical line profile image in the middle of an inverted speckle contrast image for the "flow 3" case; FIG. 16C is an inverted speckle contrast image for the "flow 3" case; and FIG. 16D is a colorized inverted speckle contrast image for the "flow 3" case.

FIGS. 17A through 17D are the averaged images for each of the cases, "no flow", "flow 1", "flow 2", and "flow 3," respectively. FIGS. 18A through 18D are colorized inverted speckle contrast images for each of the cases, "no flow", "flow 1", "flow 2", and "flow 3," respectively. FIGS. 19A through 19D are vertical line profile images for each of the cases, "no flow", "flow 1", "flow 2", and "flow 3," respectively.

Figure 20:
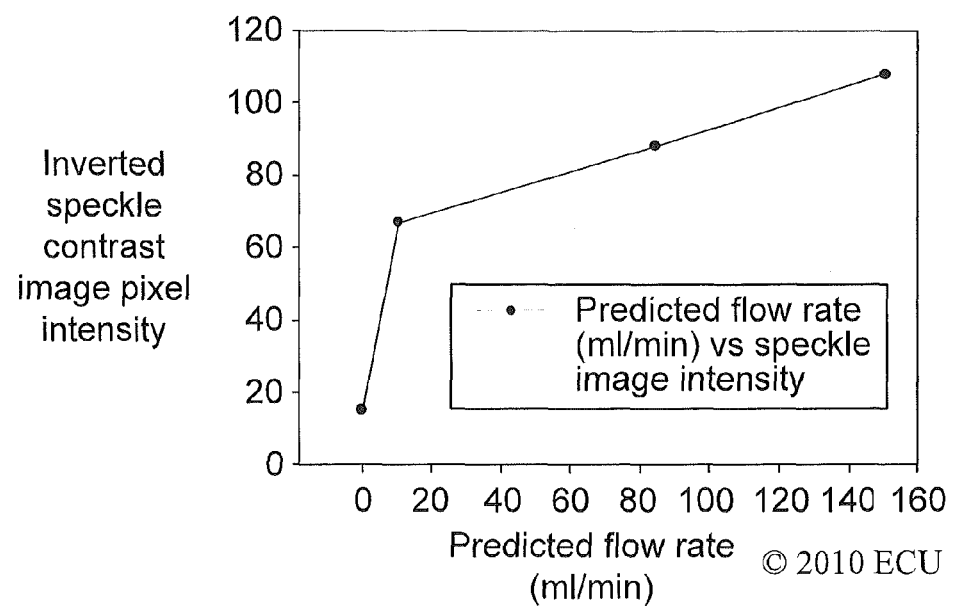
FIG. 20 is a graph illustrating predicted flow rate (ml/min) vs. inverted speckle image pixel intensity in accordance with some embodiments of the present inventive concept(s).

Table 4 set out below, summarizes the data for all four flow cases. In particular, the relationship between delta height and predicted flow is readily apparent. FIG. 20 is a graph illustrating predicted flow rate (ml/min) vs. inverted speckle contrast image pixel intensity as set out in Table 4.

TABLE 4

| Status | delta height (cm) | predicted flow rate (ml/min) | inverted speckle contrast image pixel intensity |
|---|---|---|---|
| No flow | 0 | 0 | 15 |
| Flow 1 | 10 | 10.6 | 67 |
| Flow 2 | 100 | 84.5 | 88 |
| Flow 3 | 193 | 150.7 | 108 |

To summarize the first experiment, the laser speckle contrast imaging setup is clearly able to differentiate between a no flow state and the three flow speed cases. However, the sensitivity and precision were not ideal and the point of "no flow" was not consistent with the other three flow points as illustrated in FIG. 20. Some of the imprecision may be due to using a bottle for the flow speed generation method. This may have caused variation and lack of constant flow. Furthermore, frame rate of the camera may have limited to number of speckle images that could be obtained. The laser beam intensity used during the experiment was uneven in the FOV, i.e. there are dark spots in the FOV.

However, even given this imprecision, the results shown that the higher the frame rate the better the LSCI image quality and it was discovered that the exposure time should be as long as it can in the condition that the same frame rate can be achieved.

Figure 21:
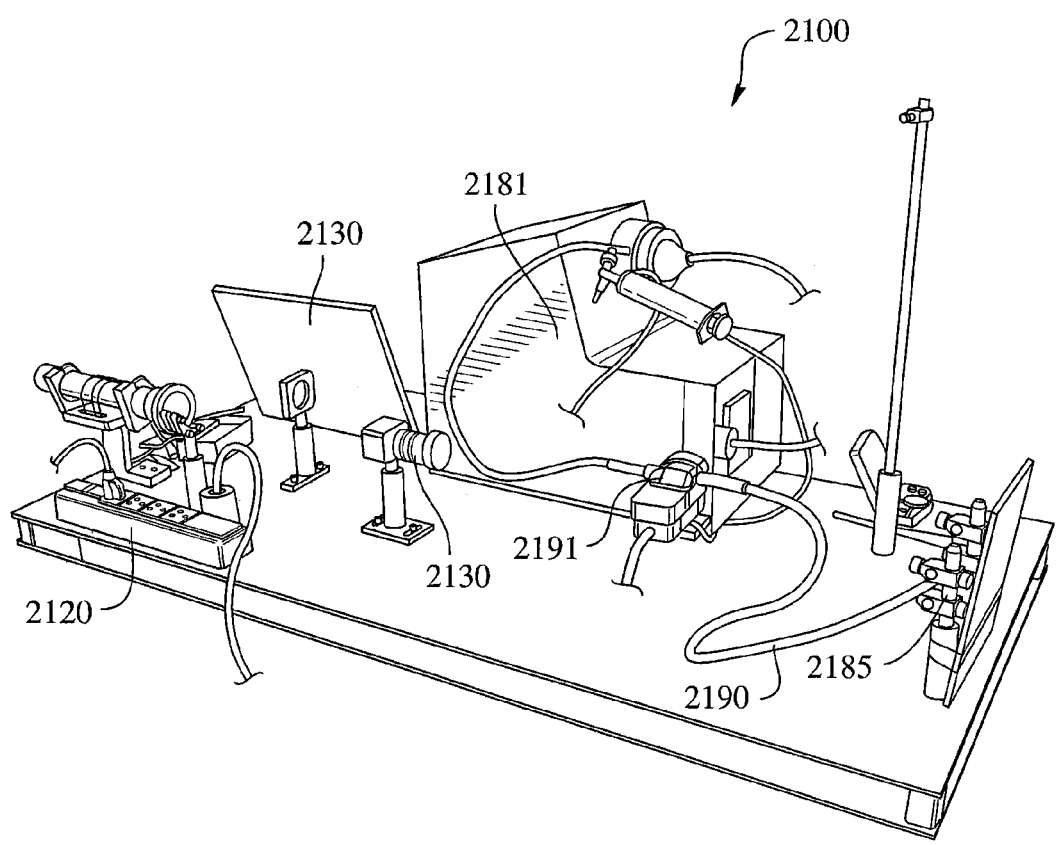
FIG. 21 is a digital photograph of an exemplary system for measuring flow of blood phantom in accordance with some embodiments of the present inventive concept(s).

Referring first to FIG. 21, a photograph of the system 2100 for a second experiment to detect flow speed using the LSCI technology in accordance with some embodiments of the present inventive concept will be discussed. As illustrated in FIG. 21, the system includes a communications device 2110, such as a laptop computer, a laser unit 2120 including a laser generator and a beam shaping lens, a camera 2130, a flow generator 2181 provided by a biomedical pump, flow liquid 2190, a flow target 2185 and an electromagnetic flow detector 2191. Table 5 set out below summarizes the actual equipment/devices used in this experiment.

TABLE 5

| Devices used in Experiment 2 | Notes |
|---|---|
| CCD camera (2130) | Lumenera Lm075 |
| Laser (2120) | 633 nm in wavelength, 1 mW in power |
| Liquid used in flow (2190) | 20% Intralipid |
| Saline water | 0.9% |
| Biomedical pump (2181) | With electromagnetic flow detector (2191) |
| Communications Device/Computer(2110) | Laptop PC |

As discussed above, the faster the camera 2130, the smaller the fixed time period has to be to obtain an adequate number of speckle images to provide a meaningful result. Thus, the limitation of the frame rate on the camera 2130 may have impacted the final result of this experiment. The laser 2120 is a low power laser providing a single coherent light source. Thus, the subject of the imaging does not typically require any protection from the laser, such as protective clothing or eyewear. The laser 2120 produces a beam having a wavelength of from about 600 nm to about 1100 nm in some embodiments. During the experiment, the laser beam produced by the laser 2120 is used to illuminate the region of interest with substantially constant intensity with the FOV of the imaging unit. This may allow the speckle contrast images to have a high signal-to-noise ratio.

Colored intralipid was used as the flow liquid 2190 during the experiment due to the fact that light scattering characteristics of intralipid are similar to those of mammalian blood. Thus, the colored intralipid will mimic the blood flowing in the human body. The communications device 2110 used was a laptop computer, although embodiments of the present inventive concept are not limited to the use of a laptop computer. The acquired speckle images are provided to the communications device 2110 and are used to calculate blood flow in according with some embodiments of the present inventive concept. As discussed above, the data are calculated using an image processing algorithm that combines temporal and spatial calculations of the acquired speckle images. Thus, spatial distribution of blood flow speed in principal vessels and perfusion distribution can be determined.

Figure 22:
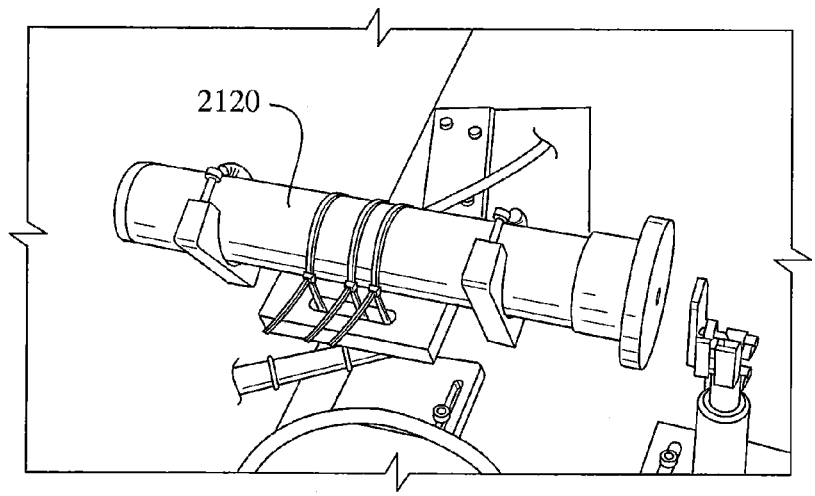
FIGS. 22 through 27 are close up photographs of the elements in the system illustrated in FIG. 21 in accordance with some embodiments of the present inventive concept(s).
Figure 23:
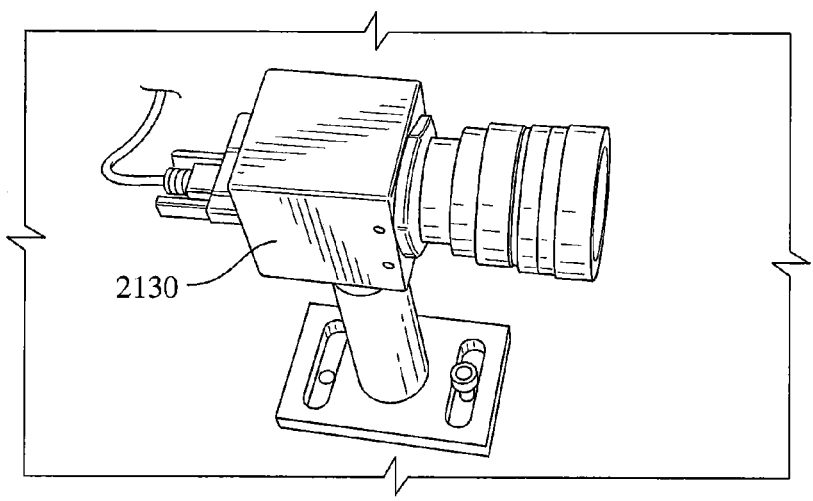
Figure 24:
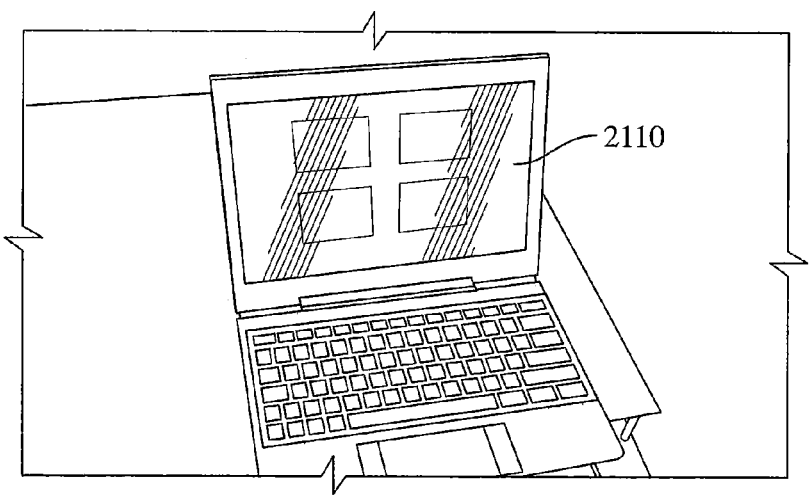
Figure 25:
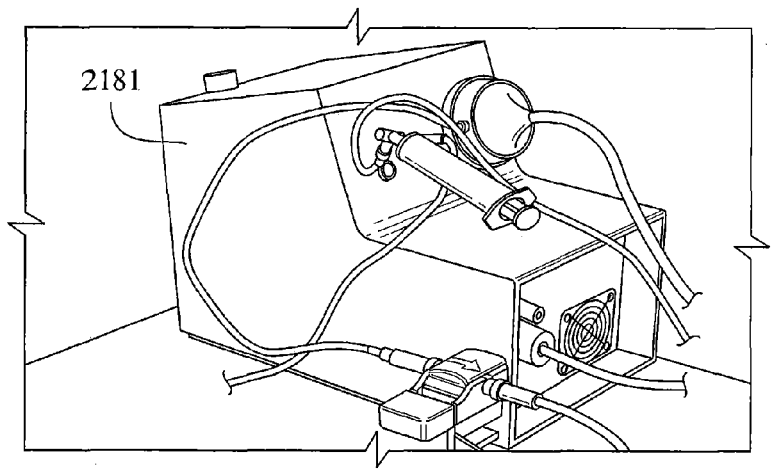
Figure 26:
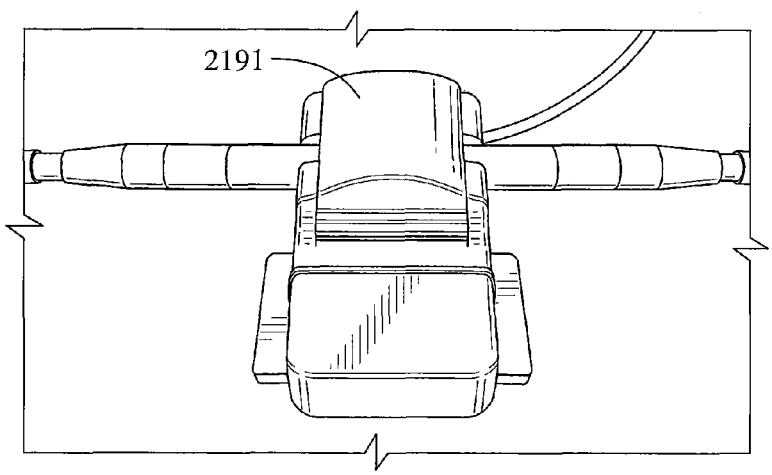
Figure 27:
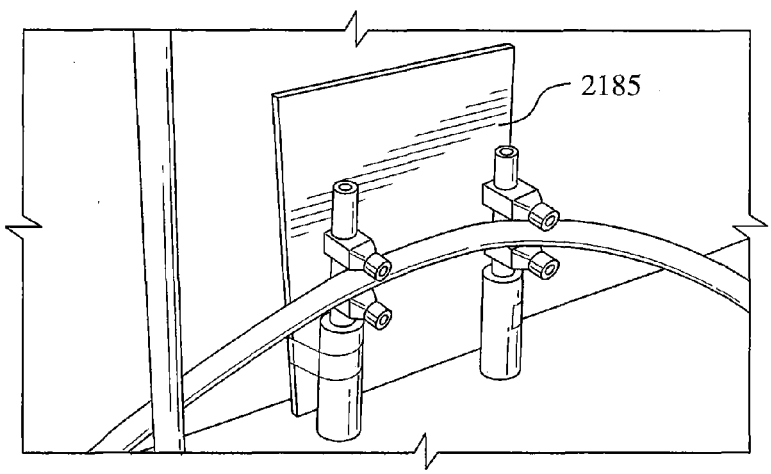

Referring now to FIGS. 22 through 27, close up photographs of the devices illustrated in FIG. 21 used during the second experiment are provided. In particular, FIG. 22 is a close up photograph of the laser unit 2120; FIG. 23 is a close up photograph of the camera 2130; FIG. 24 is a close up photograph of the communications device 2110; FIG. 25 is a close up photograph of the biomedical pump 2181; FIG. 26 is a close up photograph of the electromagnetic flow detector 2191; and FIG. 27 is a close up photograph of the flow target 2185.

Table 6 set out below summarizes parameters for the camera 530 used during the second experiment. The parameters are for the camera 2130 while the image sequence is acquired.

TABLE 6

| | |
|---|---|
| Length of image sequence | ~1 second |
| Frame rate | ~95 frames/second |
| Image resolution | 320 * 240 |
| Exposure time per frame | 3 ms (split into 3 part to calculate std and average every 3 continuous frames) |
| Gain | 1 |
| Working distance | ~1.5 m |
| Aperture | 2~4 |
| Length of the video loop | 3 * 1 second |

Estimation of the blood flow rate and speed in accordance with the second experiment will be discussed. Since the LSCI technology measures the flow speed (cm/min) rather than flow rate (ml/min), the range of the flow speed of blood in the main branches of coronary artery can be established. The second experiment focused on this range. It is contemplated that the flow rate can be calculated using the flow speed and a cross sectional area of the vessel at the same location. Table 7 set out below illustrates the estimated blood flow rate and speed range in LAD.

TABLE 7

| Average diameter of LAD (cm) | flow rate range (ml/min, cm$^3$/min) | flow speed range (cm/min) |
|---|---|---|
| 0.4 | 0~100 | 0~796 |

Procedures used for in accordance with the second experiment will now be discussed. The biomedical pump was calibrated by comparing measured liquid volume during a certain time with the reading from the electromagnetic flow detector 2591 as illustrated in Table 8 set out below. In particular, pump calibration using 20% Intralipid solution mixed by saline water with 1:4 ratio (volume was measured from 100 mL to 300 mL and reading from the detector was recorded when liquid reaches 200 mL).

TABLE 8

| Time (s) | Time (min) | Volume (mL) | flow rate reading from pump (L/min) | flow rate reading from pump (mL/min) | Calculated flow rate (ml/min) | Percentage Error | flow speed (cm/min) |
|---|---|---|---|---|---|---|---|
| 15 | 0.25 | 200 | 0.78 | 780 | 800 | 3% | 1095 |
| 18 | 0.30 | 200 | 0.65 | 650 | 667 | 3% | 913 |
| 22 | 0.37 | 200 | 0.55 | 550 | 545 | 1% | 772 |
| 26 | 0.43 | 200 | 0.45 | 450 | 462 | 3% | 632 |
| 30 | 0.50 | 200 | 0.39 | 390 | 400 | 3% | 548 |
| 49 | 0.82 | 200 | 0.24 | 240 | 245 | 2% | 337 |
| 62 | 1.03 | 200 | 0.18 | 180 | 194 | 7% | 253 |
| 111 | 1.85 | 200 | 0.11 | 110 | 108 | 2% | 154 |

Three Intralipid solutions with different concentrations were measured to simulate light scattering characteristics of blood as will be discussed below and to examine the stability of the LSCI technology. The three intralipid concentrations are summarized below in Table 9. Table 10 summarizes the volume and linear flow rate range measured during the second experiment.

TABLE 9

| Ratio of 20% Intralipid to saline water | Intralipid concentration | repeat | Note |
|---|---|---|---|
| 1:39 | 0.5% | 3 | Tube surface is processed by sand paper and collimated reflectance lights were greatly reduced. Aperture of the camera was large. ~2.5 |
| 1:19 | 1% | 3 | Tube surface is processed by sand paper and collimated reflectance lights were greatly reduced. Aperture of the camera was medium. ~3 |
| 1:9 | 2% | 3 | Same as above |

TABLE 10

| flow rate reading in 3/8 inch diameter tube | Calculated flow speed | Corresponding flow rate in 4 mm diameter LAD | Estimated maximum flow rate in coronary artery |
|---|---|---|---|
| 0~1000 mL/min | 0~1404 cm/min | 0~176 mL/min | 100 mL/min |

Results of the second experiment will now be discussed. Table 11 set out below summarizes the results for (1): 0.5% Intralipid solution (1:39); (2): 1% Intralipid solution (1:19); (3) 2% Intralipid solution (1:9) in accordance with the second experiment.

TABLE 11

(Std is standard deviation, L is the inversed speckle contrast see Equation 6 for details)

| flow rate reading from pump (mL/min) | flow speed (cm/min) | Corresponding LAD flow rate (mL/min) | L (1) | Std of L (1) | L (2) | Std of L (2) | L (3) | Std of L (3) |
|---|---|---|---|---|---|---|---|---|
| 0 | 0 | 0 | 56 | 0.6 | 51 | 0.5 | 44 | 0.1 |
| 100 | 140 | 18 | 88 | 4.7 | 88 | 1.0 | 75 | 2.0 |
| 200 | 281 | 35 | 97 | 4.6 | 94 | 2.0 | 92 | 1.0 |
| 300 | 421 | 53 | 105 | 4.3 | 110 | 2.1 | 104 | 1.1 |
| 400 | 562 | 71 | 111 | 5.5 | 112 | 0.9 | 109 | 0.3 |
| 500 | 702 | 88 | 113 | 2.9 | 117 | 2.8 | 117 | 1.4 |
| 600 | 842 | 106 | 121 | 4.0 | 118 | 2.2 | 121 | 2.8 |
| 700 | 983 | 123 | 120 | 1.0 | 113 | 3.4 | 127 | 0.3 |
| 800 | 1123 | 141 | 115 | 5.6 | 109 | 3.1 | 128 | 0.7 |
| 900 | 1264 | 159 | 113 | 3.8 | 113 | 2.1 | 123 | 5.7 |
| 1000 | 1404 | 176 | 112 | 3.8 | 106 | 6.2 | 124 | 3.8 |

Figure 28:
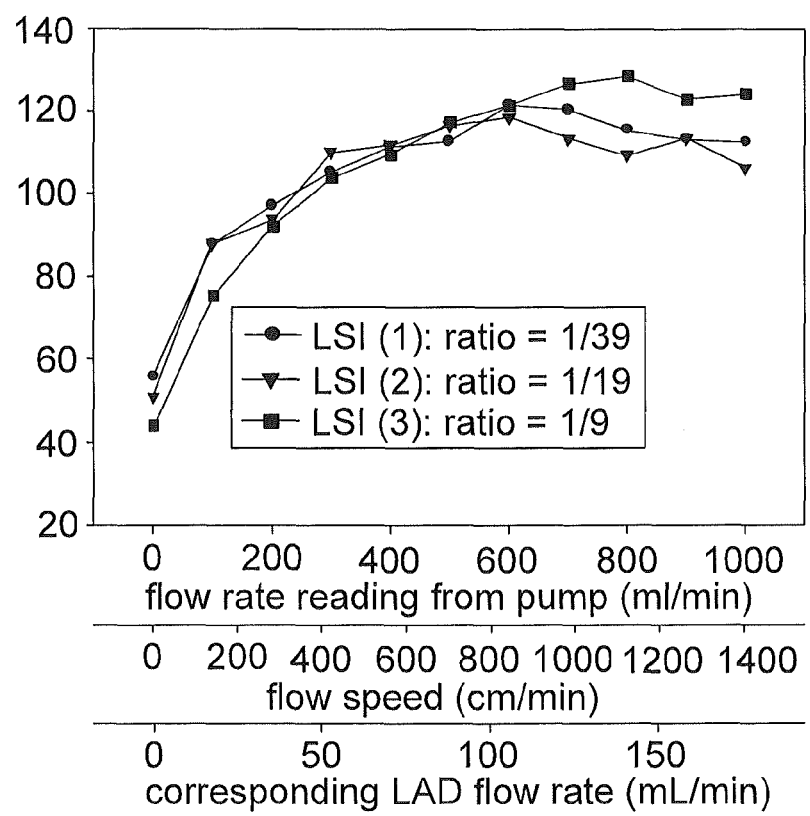
FIG. 28 is a graph illustrating flow rate (ml/min), flow speed (cm/min) and corresponding LAD flow rate vs. inverted speckle contrast image pixel intensity in accordance with some embodiments of the present inventive concept(s).

Referring now to FIG. 28, flow speed and corresponding LAD flow rate vs. the inverted speckle contrast image pixel intensity 1/K; Results obtained with ratio of 20% Intralipid to saline water of (1) 1:39; (2) 1:19; (3) 1:9 will be discussed. As illustrated in FIG. 28, the more diluted Intralipid solution has a larger background noise while flow reading is zero; after the flow speed exceeds 800 cm/min, the 1/K begins to saturate and has become less sensitive to the flow speed change; and compared to the huge concentration rage of the Intralipid solution, there is only very small change in the curves.

The quantitative relation between laser speckle contrast image pixel intensity and the flow speed will now be discussed. To make a positive correlation between the flow speed and the calculated image pixel intensity, the following equation is used to construct the inverted speckle contrast image L:

$$L(i, j) = \frac{1}{K(i, j)} = \frac{\mu(i, j)}{\sigma(i, j)} \quad \text{Equation (6)}$$

The quantitative relationship between laser speckle contrast image pixel K(i,j) and the flow speed have been derived as the following $$K(i,j) \propto \sqrt{\tau_c(i,j)/T} \quad \text{Equation (7)}$$

where T is the camera integration time, $\tau_c$ is a correlation time of scattering particles undergoing motion of speed v and given by $$\tau_c = \frac{\lambda}{2\pi v},$$

λ is laser light wavelength. Based on the above relation, the inverted speckle image pixel intensity can be written as $$L(i,j) = L_0 + a\sqrt{v(i,j)} \quad \text{Equation (8)}$$

where $L_0$ is an added term to account for background noise and should be zero after the baseline has been removed; a is a constant related to the imaging parameters, laser parameters, time/spatial smoothing parameters for obtaining K and the components of the liquid. Thus, after removing the baseline from the data of "zero flow" case from each single measurements in case (1)~(3), the Equation (8) can be used to fit the measured data.

Figure 29:
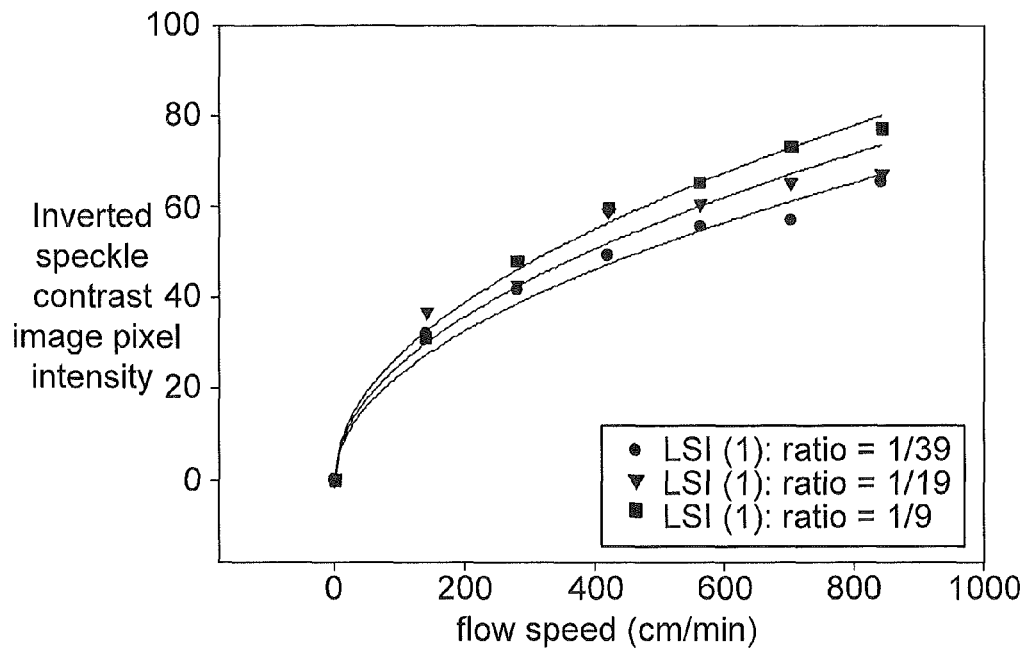
FIG. 29 is a graph illustrating flow speed vs. inverted speckle contrast image pixel intensity in accordance with some embodiments of the present inventive concept(s).

FIG. 29 is a graph illustrating flow speed vs. the L with curve fitting based on Equation (8). Table 12 summarizes the results of curve fitting, with R as the value of confidence of fitting (R=1 means perfect fitting).

TABLE 12

|  | Case (1) | case (2) | case (3) |
|---|---|---|---|
| $L_0$ | 0 | 0 | 0 |
| a | 2.3149 | 2.5413 | 2.7606 |
| R | 0.9906 | 0.9797 | 0.9974 |

Figure 30:
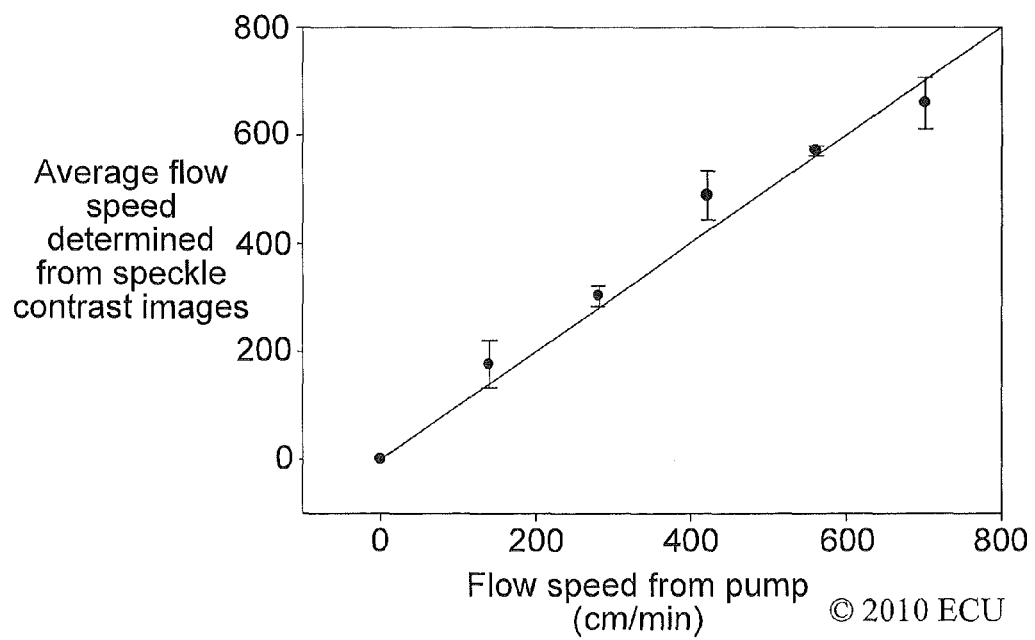
FIG. 30 is a graph illustrating average flow speed determined from speckle contrast images vs. flow speed determined from the pump flow rate in accordance with some embodiments of the present inventive concept(s).
Figure 31:
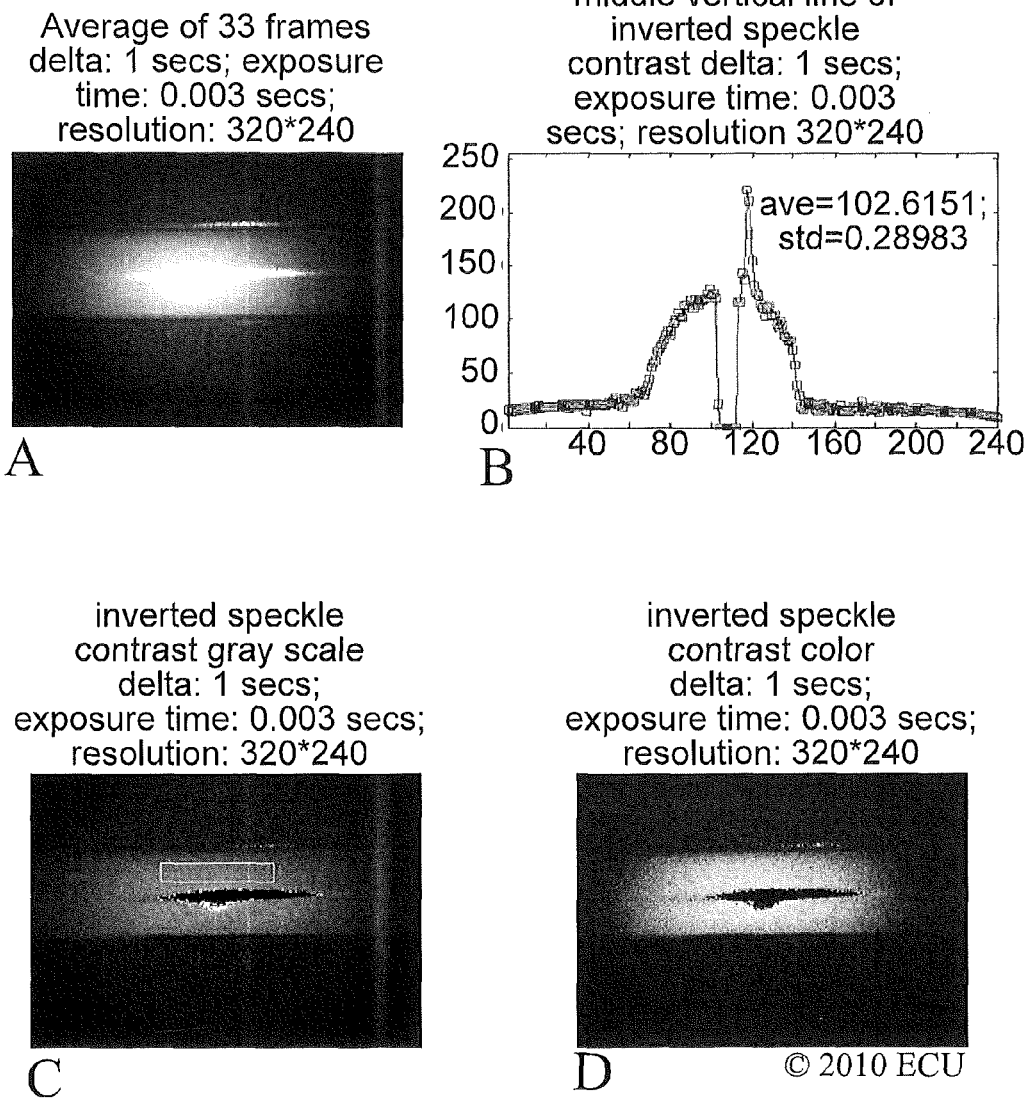
FIGS. 31A, 31C and 31D are images illustrating effect of specular reflectance on acquired speckle image data in accordance with some embodiments of the present inventive concept(s).
FIG. 31B is a graph illustrating effect of specular reflectance on acquired speckle image data in accordance with some embodiments of the present inventive concept(s).
Figure 32:
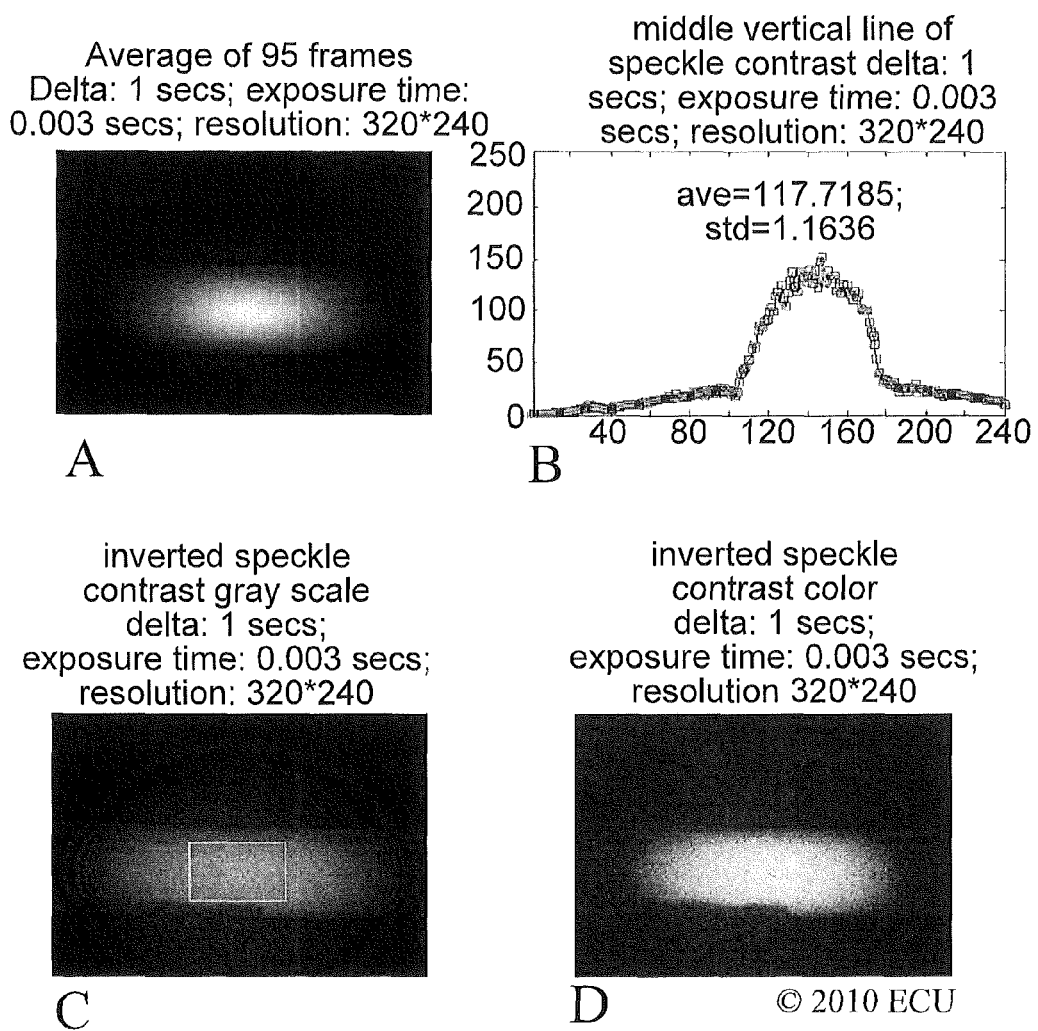
FIGS. 32A, 32C and 32D are images illustrating removal of specular reflectance of FIGS. 31A, 31C and 31D in accordance with some embodiments of the present inventive concept(s).
FIG. 32B is a graph illustrating removal of specular reflectance of FIGS. 31A, 31B and 31D in accordance with some embodiments of the present inventive concept(s).

Based on the prediction model (curve fitting), flow speed in measurements (1)~(3) were obtained to compare with the flow speed calculated from the pump readings. The results are depicted in FIG. 30, a graph illustrating the average of calculated flow speed (cm/min) from L in case (1)~(3) vs. the flow speed determined from the pump readings.

To summarize the second experiment, the experiment showed that the inverted speckle image pixel intensity L acquired with the current imaging system can correlate to the speed of the flow within certain range, (flow speed <800 cm/min or LAD flow rate<100 mL/min), which corresponds to the maximum blood flow rate in average main branch of coronary artery. Compared to the huge concentration range of the Intralipid solution, there is only very small change in the curves. The light scattering parameters of blood might fall in between case (1) and (3) as illustrated in Table 13 set out below, where $\mu_a$ is absorption coefficient, $\mu_s$ is scattering coefficient, g is anisotropy factor and $\mu_s' = (1-g)\mu_s$ is the reduced scattering coefficient.

TABLE 13

| λ = 633 nm | oxygenated blood | 10% Intralipid |
|---|---|---|
| $u_a$ (1/mm) | 0.2 | 0.0003 |
| $u_s$ (1/mm) | 31 | 34.75 |
| g | 0.99 | 0.83 |
| $u_s'$ (1/mm) | 0.31 | 5.98 |

When bubbles are trapped in the biomedical pump, they may affect the accuracy of the flow reading from electromagnetic flow meter and might affect results of measurement. Specular reflectance from the smooth surface of the tube will cause saturation of the camera and overwhelm the speckle information as shown in FIGS. 31A through 31D. In the second experiment, sand paper was used to create rough surface on the tube to eliminate this influence, the results of which are illustrated in FIGS. 32A through 32D, i.e. specular reflectance is removed by roughening the surface of the tube.

The speed detection limit of L depends on the frame rate and the number of frames used to generate the speckle contrast image somehow is related to the signal-to-noise ratio of L. Smoothing of the original images with a moving window of 3 to 5 frames helps increase the signal-to-noise ratio.

Figure 33:
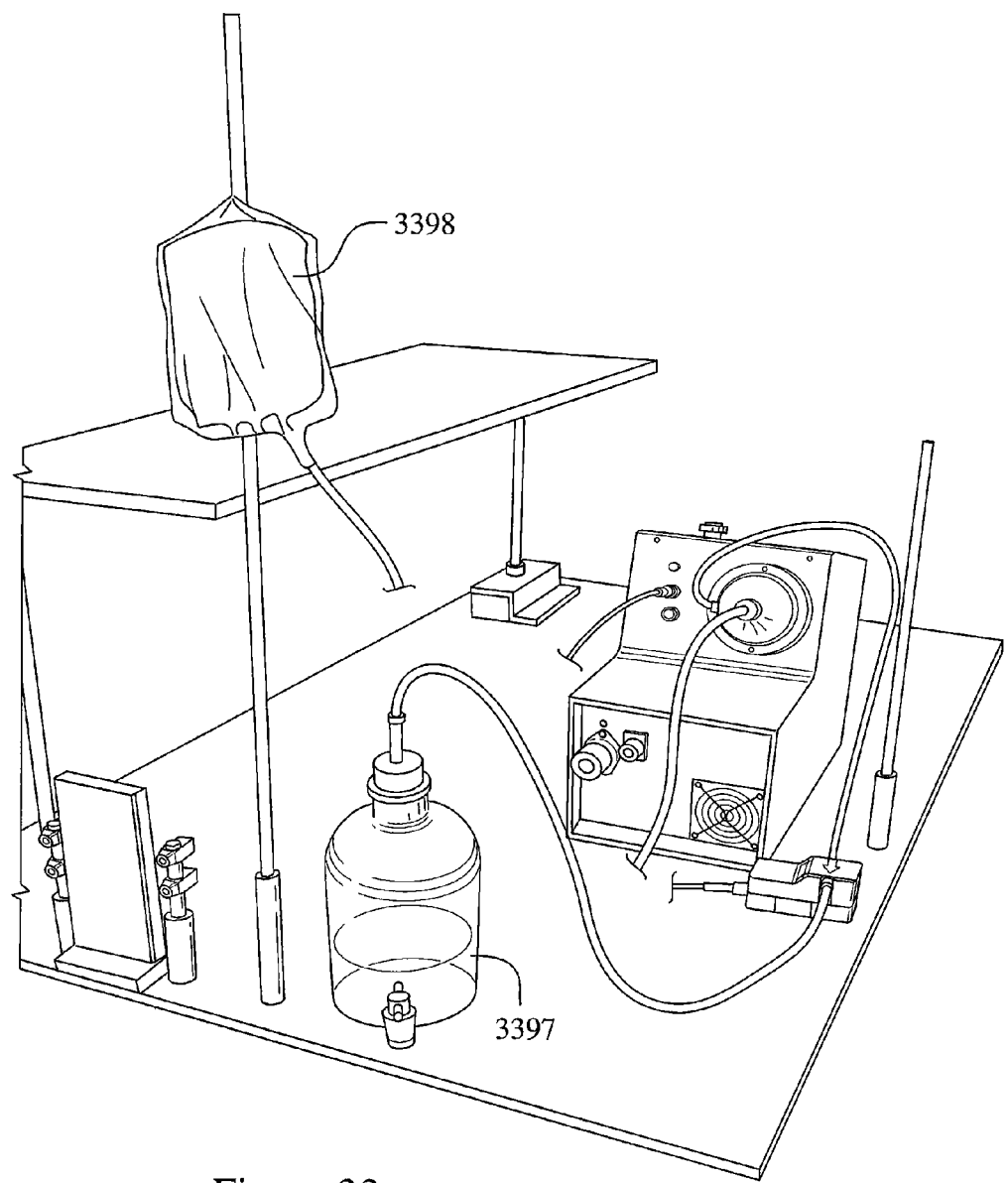
FIG. 33 is a digital photograph of an exemplary system for measuring blood flow including a reservoir used in an experiment performed in accordance with some embodiments of the present inventive concept(s).
Figure 35:
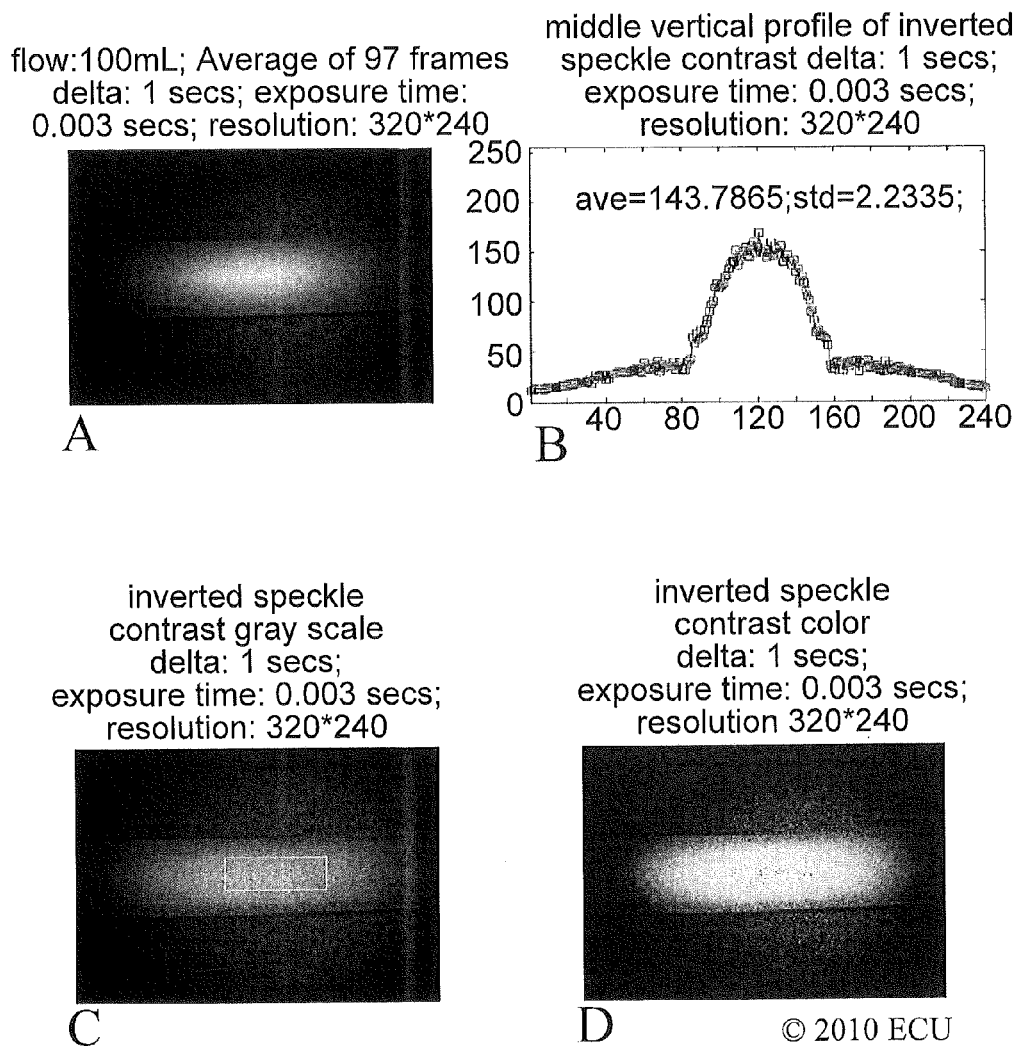
FIGS. 35A through 35D are images illustrating a "pump reading 100 mL" situation in accordance with some embodiments of the present inventive concept(s).
Figure 39:
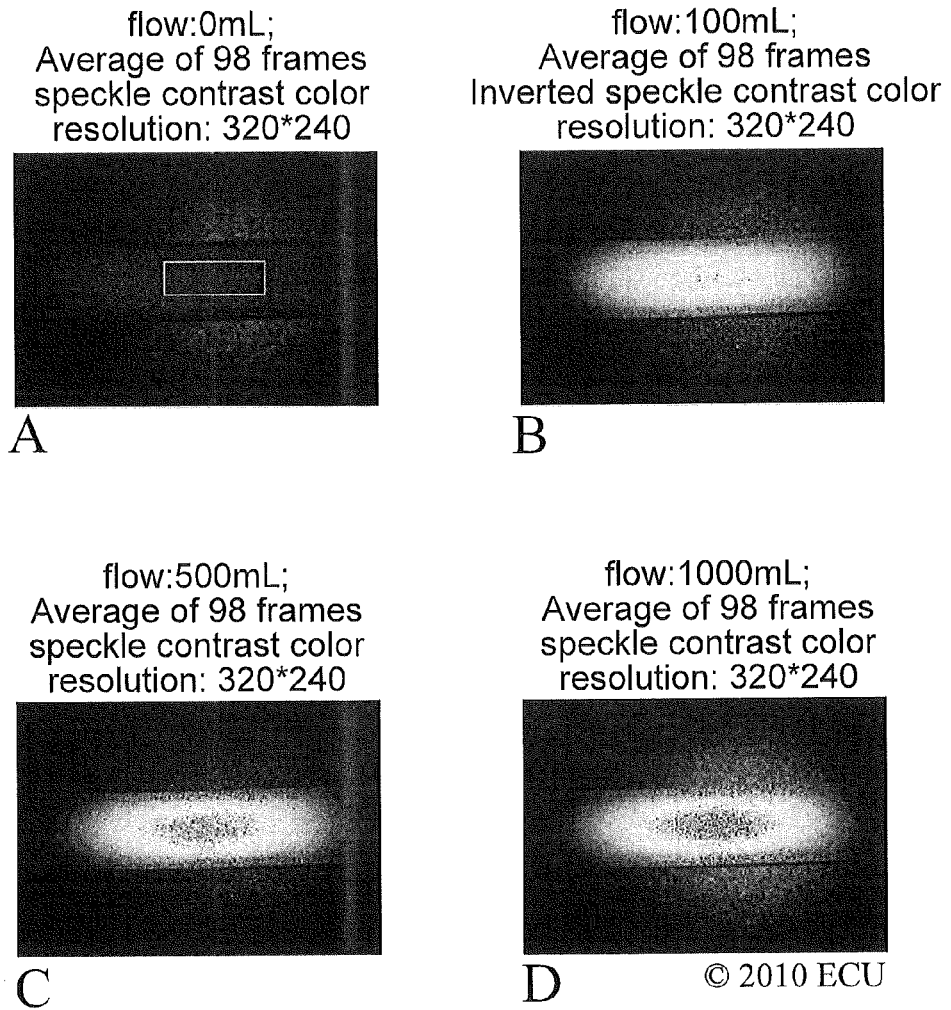
FIGS. 39A through 39D are colorized inverted speckle contrast images illustrating each of the four flow case illustrated in FIGS. 33 through 37 in accordance with some embodiments of the present inventive concept(s).
Figure 40A:
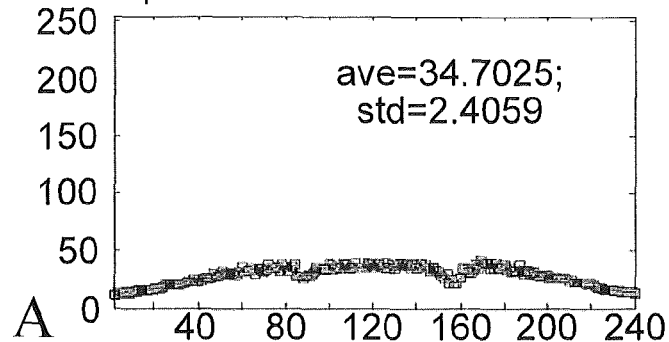
FIGS. 40A through 40D are graphs illustrating a vertical line profile of the inverted speckle contrast images for each of the four flow cases in FIGS. 33 through 37 in accordance with some embodiments of the present inventive concept(s).
Figure 40B:
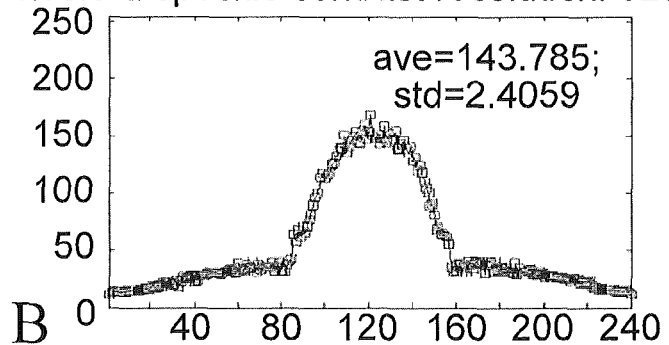
Figure 40C:
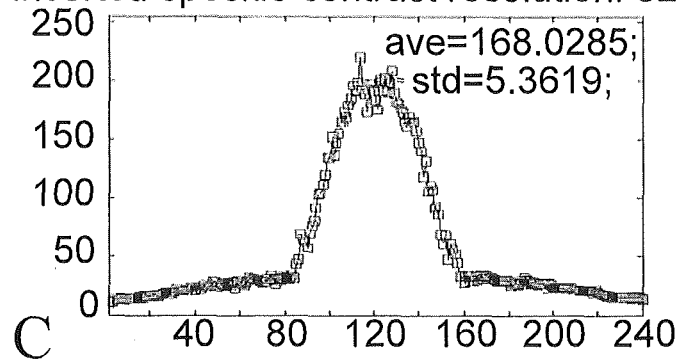
Figure 40D:
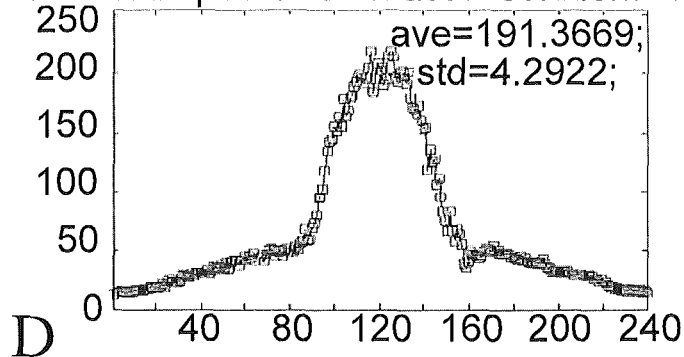

Further experiments performed in accordance with some embodiments of the present inventive concept will now be discussed with respect to FIGS. 33 through 43. FIG. 33 is a digital photograph of a prototype system setup used to detect blood flow speed using the LSCI technology in accordance with some embodiments of the present inventive concept. The experiment discussed with respect to FIGS. 33 through 43 is similar to the experiment discussed above with respect to FIGS. 21 through 32, but an extra reservoir 3397 is present to add red blood cells into the circulation from a blood bag 3398 (expired and for research use only), which is acquired from the Red Cross. Thus, many of the details of the experiment will not be repeated herein.

Table 14 set out below summarizes the actual equipment/devices used in this experiment.

TABLE 14

| Device | Parameters |
|---|---|
| CCD camera | Lumenera Lm075 |
| Laser | 633 nmin wavelength, 1 mW in power |
| Liquid used in flow | Blood (1 unit of red blood cells with hematocrit 70% + 1000 mL saline water) |
| Saline water | 0.9% |
| Biomedical pump | With electromagnetic flow rate detector |
| Computer | Laptop PC |

Table 15 set out below summarizes parameters for the camera used during the second experiment. The parameters are for the camera while the image sequence is acquired.

TABLE 15

| | |
|---|---|
| Length of image sequence | 1 second |
| Frame rate | ~95 frames/second |
| Image resolution | 320 * 240 |
| Exposure time per frame | 3 ms |
| Gain | 1 |
| working distance | 1.5~4 m |
| Aperture | 2 |
| Length of the video loop | 3 * 1 second (split into 3 part to calculate std and average every 3 continuous frames) |

Four flow cases were measured by LSCI using the setup in FIG. 33 and each situation was performed three times to test the repeatability. The flow cases tested are "tube is clamped", "pump is reading 100 mL", "pump is reading 500 mL" and "pump is reading 1000 mL" Table 16 set out below summarized the blood flows measured and the results for each situation.

TABLE 16

| flow rate reading from pump (mL/min) | flow speed (cm/min) | Corresponding LAD flow rate (mL/min) | L (blood) | std of L (blood) |
|---|---|---|---|---|
| Tube clamped | | | 35 | 2 |
| 0 | 0 | 0 | 84 | 1 |
| 100 | 140 | 18 | 144 | 2 |
| 200 | 281 | 35 | 153 | 4 |
| 300 | 421 | 53 | 156 | 6 |
| 400 | 562 | 71 | 164 | 6 |
| 500 | 702 | 88 | 168 | 4 |
| 600 | 842 | 106 | 174 | 3 |
| 700 | 983 | 123 | 179 | 3 |

TABLE 16-continued

| flow rate reading from pump (mL/min) | flow speed (cm/min) | Corresponding LAD flow rate (mL/min) | L (blood) | std of L (blood) |
|---|---|---|---|---|
| 800 | 1123 | 141 | 180 | 10 |
| 900 | 1264 | 159 | 188 | 1 |
| 1000 | 1404 | 176 | 191 | 4 |

(Std is standard deviation, L is the inversed speckle contrast see Equation 6 for details)

FIGS. 34A through 34D illustrate resultant images obtained for the "tube is clamped" case. FIG. 34A is an averaged image of 90 frames for the "tube is clamped" case; FIG. 34B is a vertical line profile image in the middle of inverted speckle contrast image for the "tube is clamped" case; FIG. 34C is an inverted speckle contrast image for the "tube is clamped" case; and FIG. 34D is a false-color inverted speckle contrast image for the "tube is clamped" case.

FIGS. 35A through 35D illustrate resultant images obtained for the "pump reads 100 mL" case. FIG. 35A is an averaged image of 97 frames for the "100 mL" case; FIG. 35B is a vertical line profile in the middle of an inverted speckle contrast image for the "100 mL" case; FIG. 35C is an inverted speckle contrast image for the "100 mL" case; and FIG. 35D is a false-color inverted speckle contrast image for the "100 mL" case.

FIGS. 36A through 36D illustrate resultant images obtained for the "pump reads 500 mL" case. FIG. 36A is an averaged image of 97 frames for the "500 mL" case; FIG. 36B is a vertical line profile image in the middle of an inverted speckle contrast image for the "500 mL" case; FIG. 36C is a n inverted speckle contrast image for the "500 mL" case; and FIG. 36D is a false-color speckle contrast image for the "500 mL" case.

FIGS. 37A through 37D illustrate resultant images obtained for the "pump reads 1000 mL" case. FIG. 37A is an averaged image of 98 frames for the "1000 mL" case; FIG. 37B is a vertical line profile image in middle of an inverted speckle contrast image for the "1000 mL" case; FIG. 37C is an inverted speckle contrast image for the "1000 mL" case; and FIG. 37D is a false-color inverted speckle contrast image for the "1000 mL" case.

FIGS. 38A through 38D are averaged images for each of the cases, "pump clamped", "100 mL", "500 mL", and "1000 mL," respectively. FIGS. 39A through 39D are colorized inverted speckle contrast images for each of the cases, "pump clamped", "100 mL", "500 mL", and "1000 mL," respectively. FIGS. 40A through 40D are vertical line profile images for each of the cases, "pump clamped", "100 mL", "500 mL", and "1000 mL," respectively.

Figure 41:
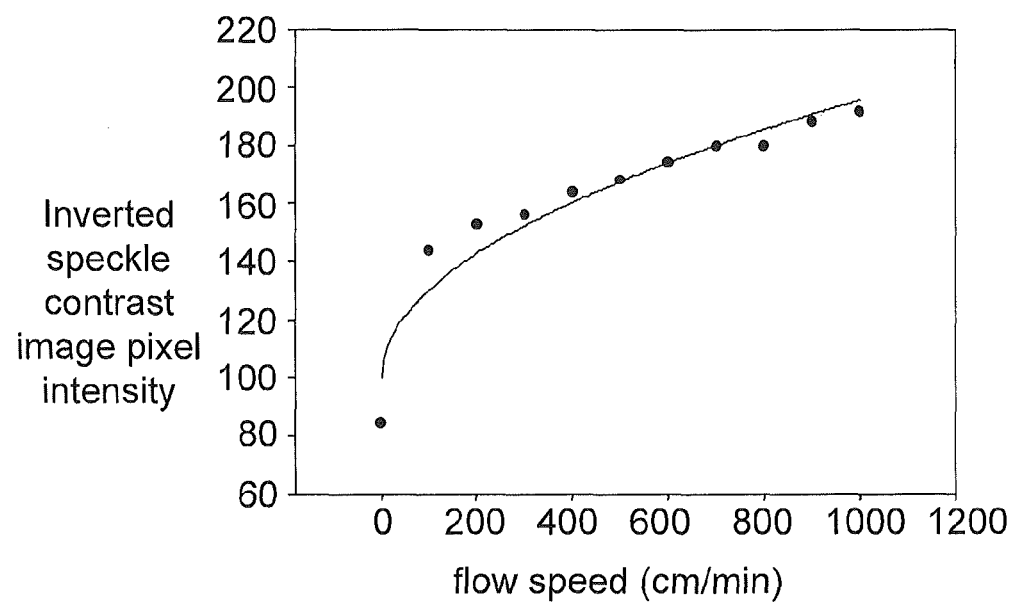
FIG. 41 is a graph illustrating flow speed (cm/min) vs. inverted speckle contrast image pixel intensity in accordance with some embodiments of the present inventive concept(s).

FIG. 41 of a graph of flow speed vs. L with to the line fitting the data based on Equation (8). Table 17 set out below summarized the curve fitting parameters using Equation (8).

TABLE 17

| | L (1) |
|---|---|
| $L_0$ | 100 |
| a | 3.0 |
| R | 0.96 |

Figure 42:
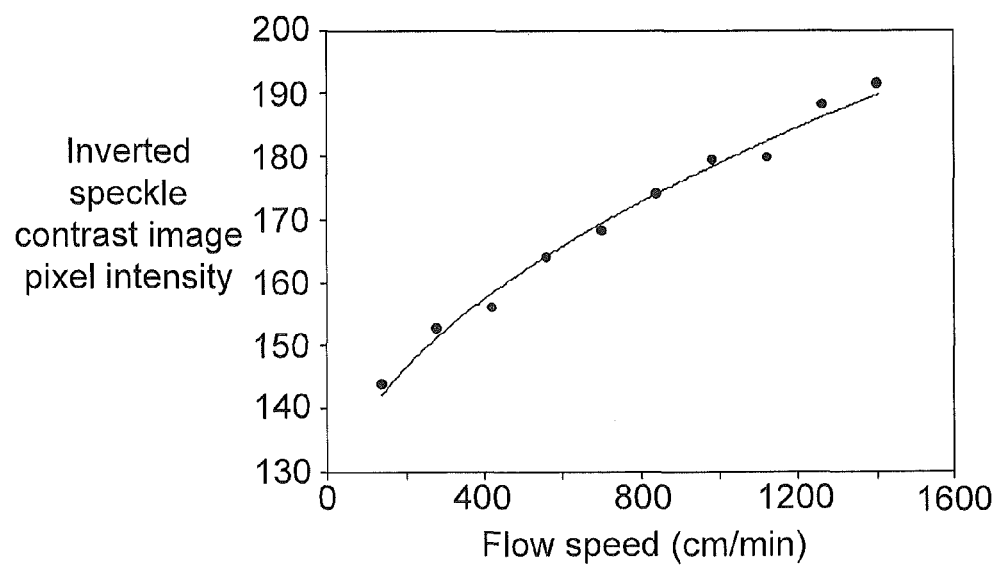
FIG. 42 is a graph illustrating flow speed (cm/min) vs. inverted speckle contrast image pixel intensity in accordance with some embodiments of the present inventive concept.
Figure 44:
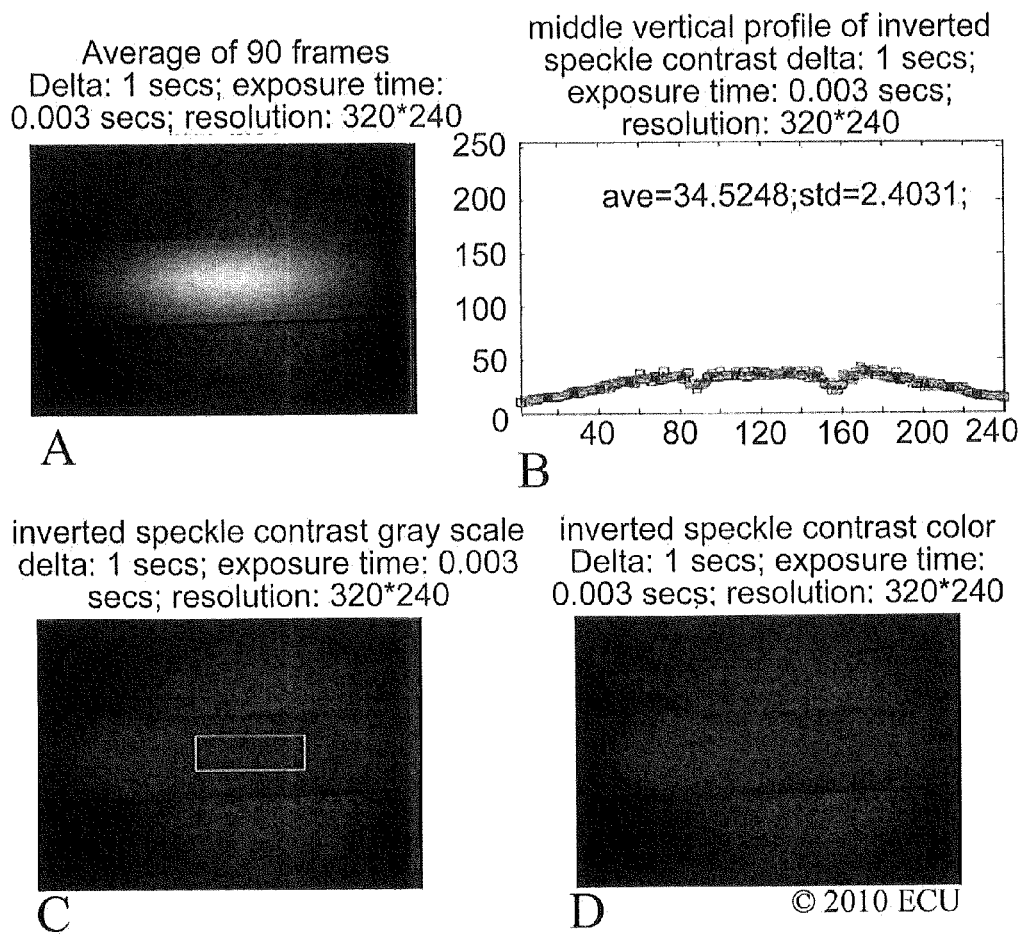
FIGS. 44A through 44D are images illustrating a "clamped pump" situation in accordance with some embodiments of the present inventive concept(s).

The laser speckle imaging setup illustrated in FIG. 33 is clearly able to differentiate different flow speeds of human blood. In particular, when the reading from the pump is zero, the LSCI image still has contrast related to flow speed as illustrated in FIGS. 43A through 43D. Until the tube is clamped, the contrast disappears as shown in FIGS. 44A through 44D. Thus, when the flow speed is very low, is the pump reading still accurate? The power of the speed term v in Equation (8) after curve fitting was found not equal to 0.5, which is different from the Intralipid solution as discussed above with respect to FIGS. 21-32. If the data related to "no flow" case is discarded, one can see that the rest of data fit the Equation (8) well, the result is summarized in the graph of FIG. 42 illustrating flow speed vs. L with Equation (8) after the baseline removed. Thus, the Equation (6) with the power factor of 0.5 will fit the data well. Table 18 set out below summarizes the curve fitting parameters.

TABLE 18

| | L (1) |
|---|---|
| $L_0$ | 120 |
| a | 1.86 |
| R | 0.994 |

Figure 45:
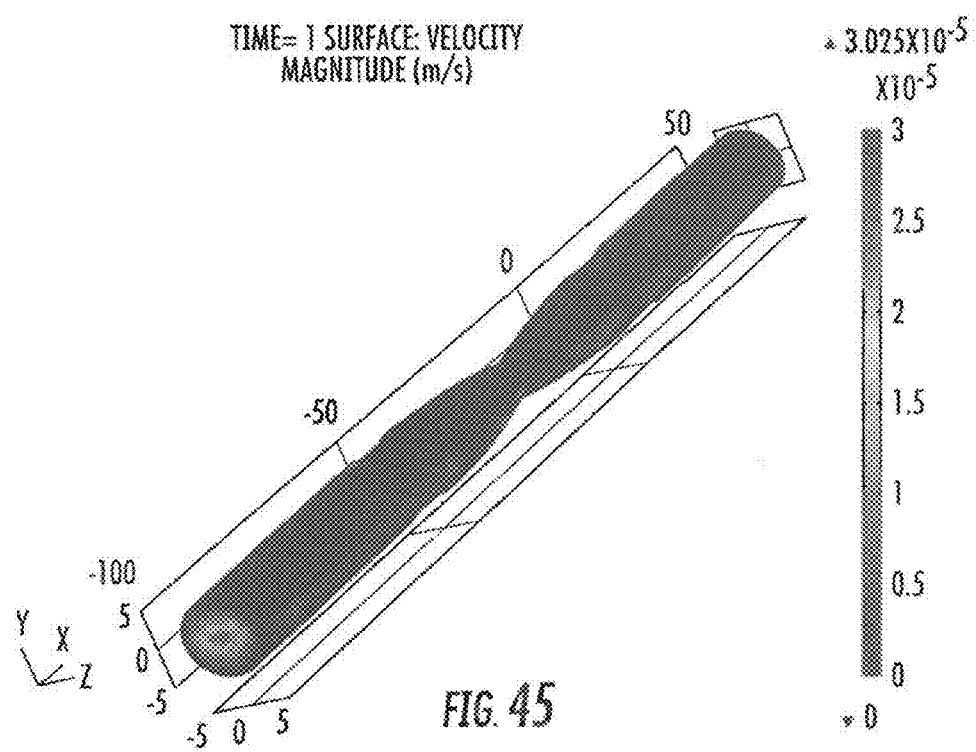
FIG. 45 is a diagram of a blood vessel having a narrowing in the middle thereof that can be accessed using methods and systems in accordance with some embodiments of the present inventive concept.
Figure 46:
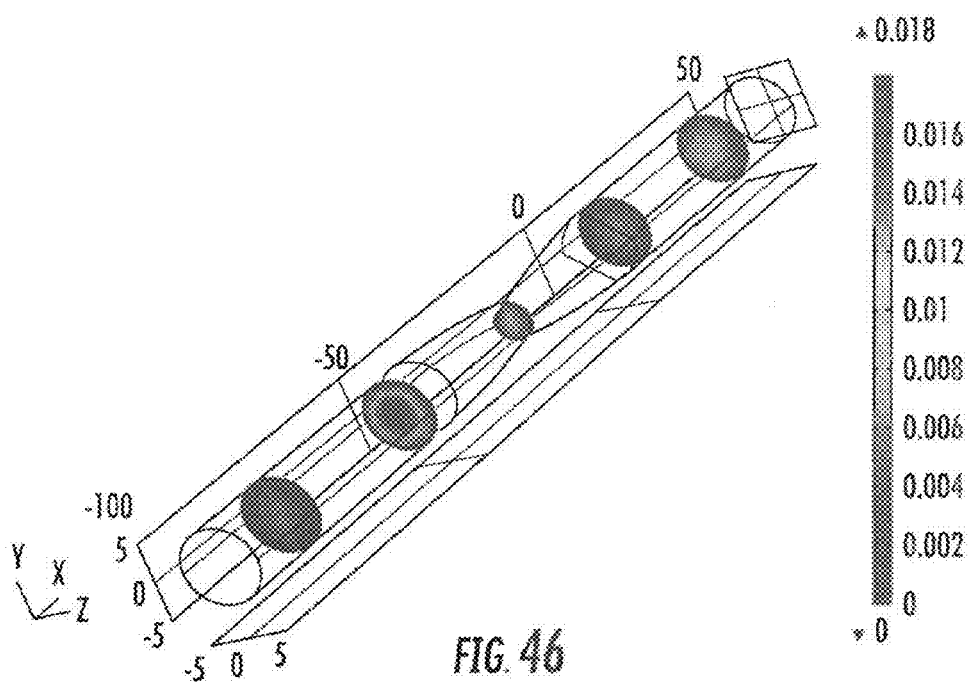
FIG. 46 is a diagram illustrating velocity profiles of various locations in the blood vessel illustrated in FIG. 45 obtained using flow hemodynamic modeling in accordance with some embodiments of the present inventive concept.
Figure 47:
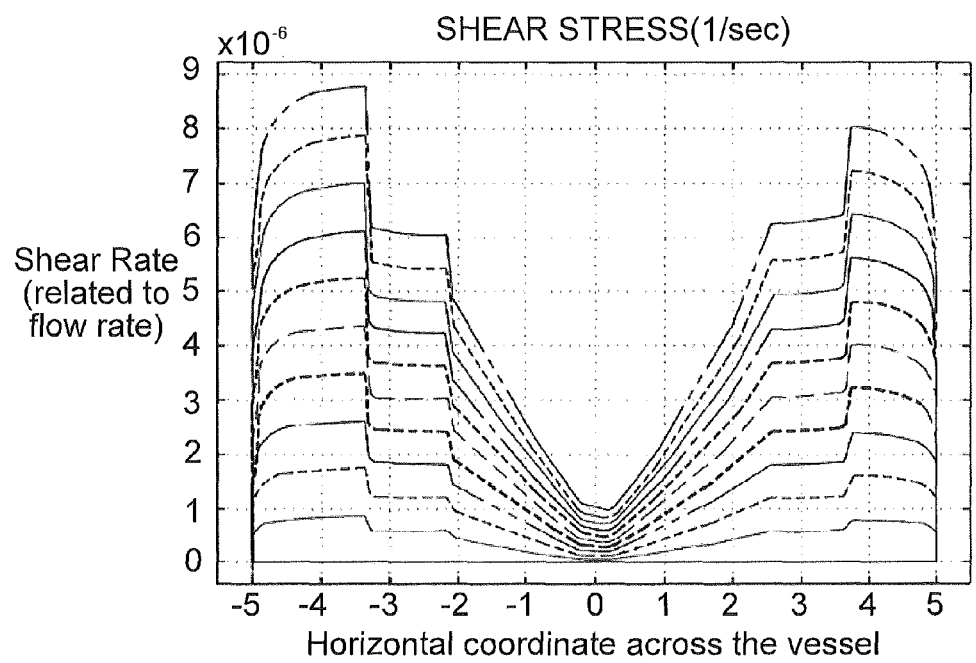
FIG. 47 is a graph illustrating shear rate (which is related to flow rate) and horizontal coordinate (diameter) across the blood vessel illustrated in FIGS. 45 and 46 when the shear stress is about 1.0 second in accordance with some embodiments of the present inventive concept.

As discussed above, the data obtained using the speckle images discussed above can be verified using hemodynamic modeling as will be discussed with respect to FIGS. 45 through 47. The Navier-Stokes equation provides the governing equation for fluid dynamics.

The Navier-Stokes equation is set out below in Equations (9) and (10):

$$\rho \cdot \left( \frac{\partial u}{\partial t} + u\nabla \cdot u \right) = -\nabla p + \mu \cdot \nabla^2 u + F \quad \text{Equation (9)}$$

$$\frac{\partial \rho}{\partial t} + \nabla \cdot (\rho u) = 0 \quad \text{Equation (10)}$$

where $\rho$ is the density (kg/m$^3$), u is the velocity vector (m/s), p is the pressure (m/s), F is the volume force vector (N/m$^3$) and m is the viscosity.

Solving the Navier-Stokes equations produces a velocity field, i.e. a distribution of fluid velocity in space and time. Once this velocity field is obtained, other quantities of interest, such as flow rate and drag force, can be calculated. These calculated quantities can then be compared to the experimental data obtained using the speckle images discussed above to validate the data.

Furthermore, these quantities may be calculated before a procedure is performed on a subject and after a procedure is performed on the subject to verify that the procedure was successful. For example, measurements, images and calculations discussed above may be performed before a subject undergoes a carotid endarterectomy (CEA), which is a surgical procedure used to reduce the likelihood, or possibly prevent stroke, by correcting stenosis (narrowing) in the common carotid artery. Endarterectomy is the removal of material on the inside (end-) of an artery. A blood vessel 4501 including a narrowing 4597 is illustrated, for example, in FIG. 45. A velocity field/profile may be calculated at various point in the blood vessel as illustrated in FIG. 46 before and after the carotid endarterectomy to correct the narrowing 4597. Thus, by comparing the measurements/quantities before and after the procedure, the success of the procedure may be determined. FIG. 47 is a graph illustrating fluid rate estimate along the diameter of the blood vessel 4501 illustrated in FIGS. 45 and 46.

Although uses of the methods and systems discussed herein are discussed specifically with respect to carotid endarterectomies, it will be understood that embodiments of the present inventive concept are not limited to this configuration.

For example, embodiments of the present inventive concept may be used for the brain, colon, or any other applicable part of the subject that may benefit from the techniques discussed herein.

Figure 48:
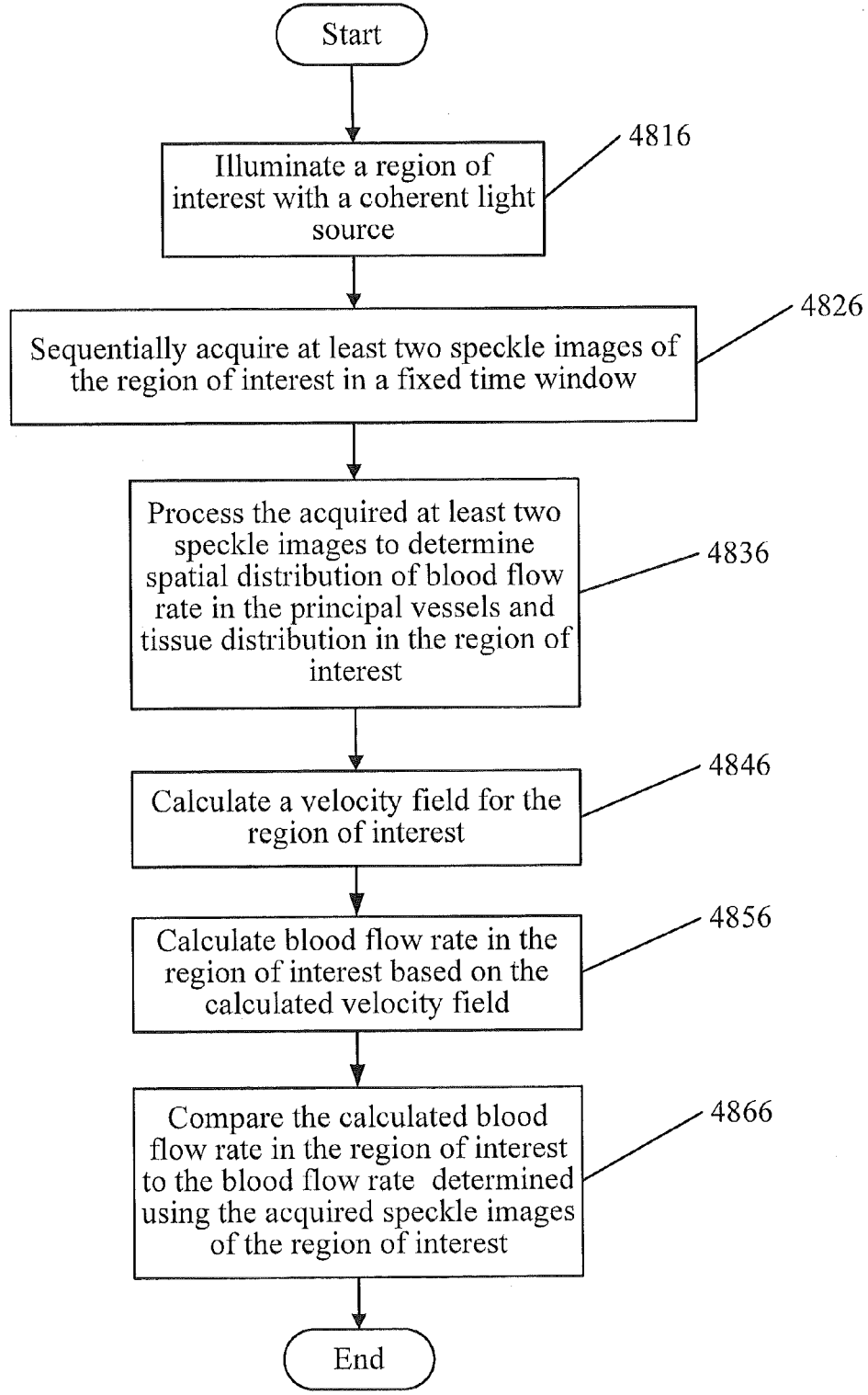
FIG. 48 is a flowchart illustrating operations for measuring blood flow in principal vessels in accordance with various embodiments of the present inventive concept(s).

Operations for a non-invasive method for measuring blood flow in principal vessels of a subject in accordance with some embodiments will be discussed with respect to FIG. 48. Operations begin at block 4816 by illuminating a region of interest with a coherent light source, wherein the coherent light source has a wavelength of from about 600 nm to about 1100 nm. At least two speckle images of the region of interest are sequentially acquired during a fixed time period (block 4826). Temporal and spatial variation of pixel intensities of the at least two acquired speckle images are electrically evaluated to determine spatial distribution of blood flow speed in the principal vessels and perfusion distribution in tissue in the region of interest (block 4836).

A velocity field for the region of interest is calculated (block 4846). In some embodiments, the velocity field is calculated using equations (9) and (10) set out below. Blood flow speed in the region of interest based on the calculated velocity field is calculated (block 4856). The calculated blood flow speed in the region of interest is compared to the blood flow speed determined using the acquired at least two speckle images of the region of interest to verify results obtained using the at least two speckle images (block 4866). Thus, embodiments of the present inventive concept may be used to verify experimental results as will be discussed further below.

It will be understood that the operations of blocks 4816, 4826, 4836, 4846, 4856 and 4866 may be performed before and after a procedure performed on the subject. The results before and after the procedure may be compared to verify the success of the procedure in the subject.

In the cardiac space things happen so quickly that timing can be normalized, i.e. the velocity of flow is so fast, time may not be a factor. However, in other portions of the body, for example, the extremities things happen much slower (velocity of flow is much slower) and, therefore, timing is much more important. Thus, according to embodiments of the present inventive concept discussed herein, an EKG may be used to synchronize data acquisition, which may allow relative comparison of a same area over time. This synchronization may allow use of LSI methods discussed herein in many areas of the body beyond the heart. Use of the EKG as a synchronization tool may also enable generation of instantaneous and average measurements of flow and/or perfusion as will be discussed further herein with respect to FIGS. 49 through 67.

As will be discussed, in accordance with some embodiments of the present inventive concept experiments were performed on a human heart, both stopped and beating. As will be discussed, speckle imaging techniques discussed herein can not only be used for non-invasive determination of blood flow speed in the principal vessels and to quantify perfusion distribution in tissue in the region of interest from the LSCI image, but also to generate instantaneous and average flow and perfusion maps. Furthermore, as discussed above, EKG gating is used as a temporal standard for analysis for acquisition of data both in the heart region as well as other areas of the body where this information may be useful. Because the LSI data in accordance with embodiments discussed herein are synchronized using EKG gating, LSI technology in accordance with embodiments of the present inventive concept will be discussed herein as "triggered LSI." In other words, the data collection is synchronized using a metric, in embodiments discussed herein, the metric may be a patient's EKG and, thus, the acquisition of the LSI image is "triggered."

Figure 49:
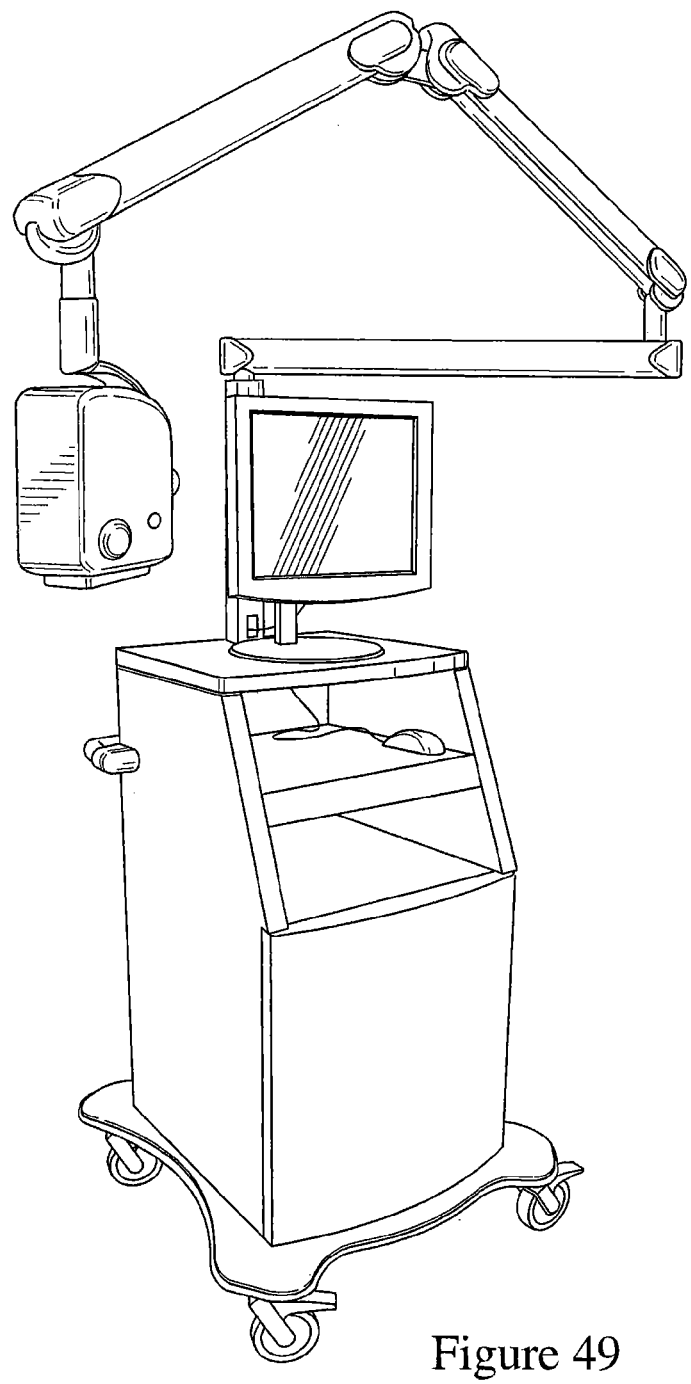
FIG. 49 is a diagram of a SPY device system used in accordance with some embodiments of the present inventive concept.

Referring first to FIG. 49, experiments discussed herein were performed using a SPY® Imaging System illustrated in FIG. 49. The SPY imaging system is offered by Novadaq Technologies Inc. The SPY system is easily mobile from room to room. Set up can be managed by the operating room staff. The articulating arm and camera head are controlled by the surgeon. Image capture may accomplish in less than two minutes and images can be replayed immediately for review.

Experiments in accordance with embodiments of the present inventive concept were performed using the SPY system as the SPY system was a readily available fluorescence imaging system. However, modifications were made to the system for embodiments discussed herein. For example, no ICG dye was injected into the subject as the triggered LSI procedure discussed herein does not use dye injection. Using the SPY system presented various disadvantages, for example, the frame rate of the SPY device is slow, about 30 frames per second (fps), which the limits the amount of data that can be acquired. Furthermore, the wavelength of the laser in the SPY device is about 810 nm, but fluorescence is about 830 nm. There is a long pass filter in front of the camera that removes most of the 810 nm light. Triggered LSI only uses 810 nm and the reflected light is decreased to $1/10,000$ because of the filter. Thus, results may be greatly improved with equipment optimized for triggered LSI. As discussed, in the later examples and figures, the SPY system primarily functioned in these experiments simply as the laser illumination source. As will be illustrated below, however, results obtained using the SPY device are capable of illustrating various aspects of the present inventive concept as will be discussed below.

Although many the following figures are discussed with respect to a stopped and/or beating heart, embodiments of the present inventive concept are not limited to this configuration. For example, embodiments of the present inventive concept may be used in coronary artery bypass, cardiovascular, plastic, reconstructive, micro, organ transplant and gastrointestinal surgery as well as many other procedures that could benefit from the information provided by the inventive concept without departing from the scope of the present inventive concept.

Referring now to FIGS. 50A and 50B, the images illustrated therein were obtained using LSI imaging using the modified SPY device on a motionless, non-beating heart using a heart-lung machine and no dye was injected into the subject. In particular, FIG. 50A illustrates a single frame of LSI data and FIG. 50B illustrates an inverse laser speckle temporal contrast imaging (LSTCI) image in accordance with embodiments of the present inventive concept. As illustrated in FIG. 50B, the left anterior descending coronary artery (LAD) is clearly visible in the LSTCI image. The stopped heart (AKA antegrade cardioplegia) imaged in FIGS. 50A and 50B was with the patient on the cardiopulmonary bypass pump. The LAD in FIG. 50B has a high velocity flow. As discussed above, these images were obtained using the SPY device where reflective light is decreased to $1/10,000$ due to the filter. However, the LAD is still very visible in the LSTCI image of FIG. 50B. Although FIG. 50B illustrates a temporal contrast image, it will be understood that both spatial and temporal contrast analyses are used in accordance with embodiments discussed herein.

Figures 51A, 51B:
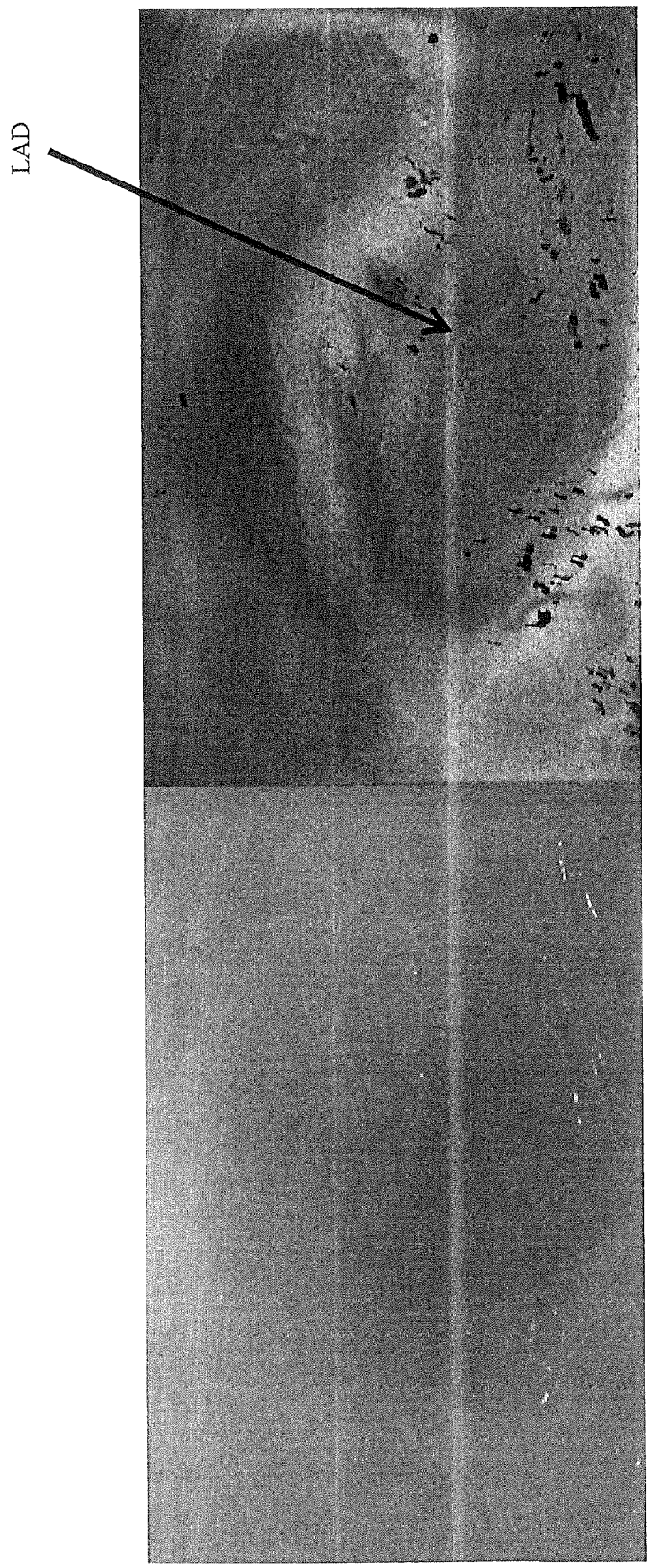
FIGS. 51A and 51B are images illustrating a single LSI image and a inverse LSCTI image, respectively, in accordance with some embodiments of the present inventive concept.

Referring now to FIGS. 51A and 51B, the images illustrated therein were obtained using LSI imaging using the modified SPY device on the same motionless, non-beating heart as illustrated in FIGS. 50A and 50B, but fluid was injected retrograde (AKA retrograde cardioplegia) for these images. In particular, FIG. 51A illustrates a single frame of LSI data and FIG. 51B illustrates an LSTCI image in accordance with embodiments of the present inventive concept. As illustrated in FIG. 51B, the left anterior descending coronary artery (LAD) is clearly visible in the LSTCI image and has lower velocity of flow than the LAD illustrated in FIG. 50B. The stopped heart (AKA retrograde cardioplegia) imaged in FIGS. 51A and 51B was with the patient on the cardiopulmonary bypass pump. Thus, embodiments of the present inventive concept can be used to detect differences in velocity at different points in time in the same vessels, for example, the LAD illustrated in FIGS. 50B (antegrade flow, higher velocity) and 51B (retrograde flow, lower velocity).

Figures 52A, 52B:
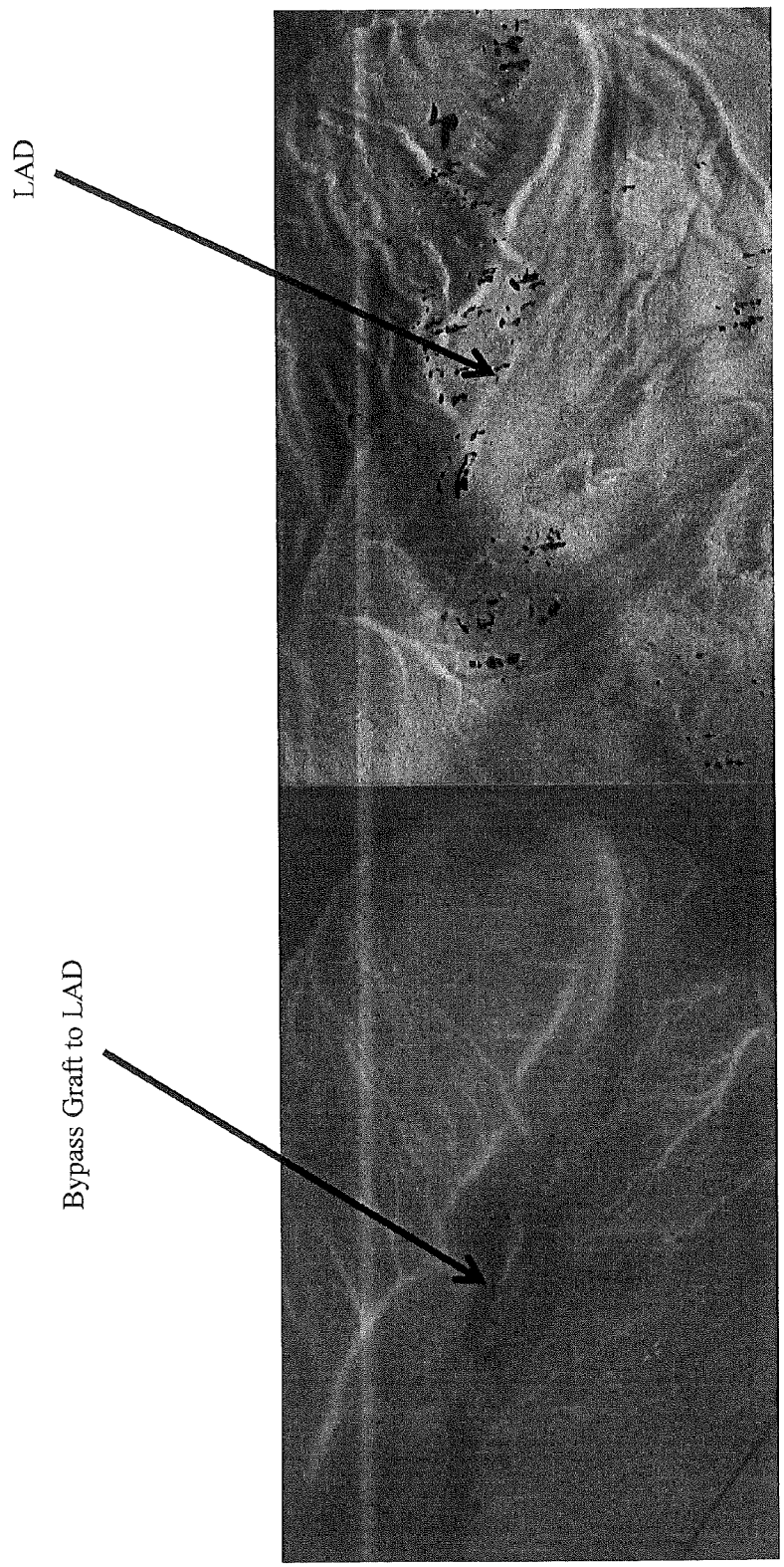
FIGS. 52A and 52B are images illustrating a conventional SPY image and a LSCTI image, respectively, in accordance with some embodiments of the present inventive concept.

Referring now to FIGS. 52A and 52B, a conventional near-infrared fluorescence SPY image is compared to a LSTCI image in accordance with embodiments discussed herein. In particular, FIG. 52A illustrates one frame of a conventional SPY image system in venous phase. As illustrated in FIG. 52A, the bypass graft to the LAD is identified in the SPY image. FIG. 52B is an image generated using inverse LSTCI in accordance with embodiments discussed herein. The LAD is pointed out in FIG. 52B. When these images are compared, it is clear that the image generated using embodiments of the present inventive concept of FIG. 52B is very similar to the SPY image of FIG. 52A. In other words, embodiments of the present inventive concept are illustrating the imaged anatomy accurately. Furthermore, as discussed above, using triggered LSI technology in accordance with embodiments discussed herein, different velocities in the arteries and veins can be illustrated. SPY systems only provide images of flow (1) or no flow (0), but cannot depict different velocities of flow as discussed herein.

Information related to the velocity of flow may be very useful to, for example, a surgeon placing a graft on the heart. In real time, embodiments of the present inventive concept may allow the surgeon to access the velocity of flow in the arteries and veins around the graft before the placement of the graft and after placement of the graft, thus, allowing an assessment of the surgeries success in real time. This information may be very valuable as will be discussed further below.

Figure 53A:
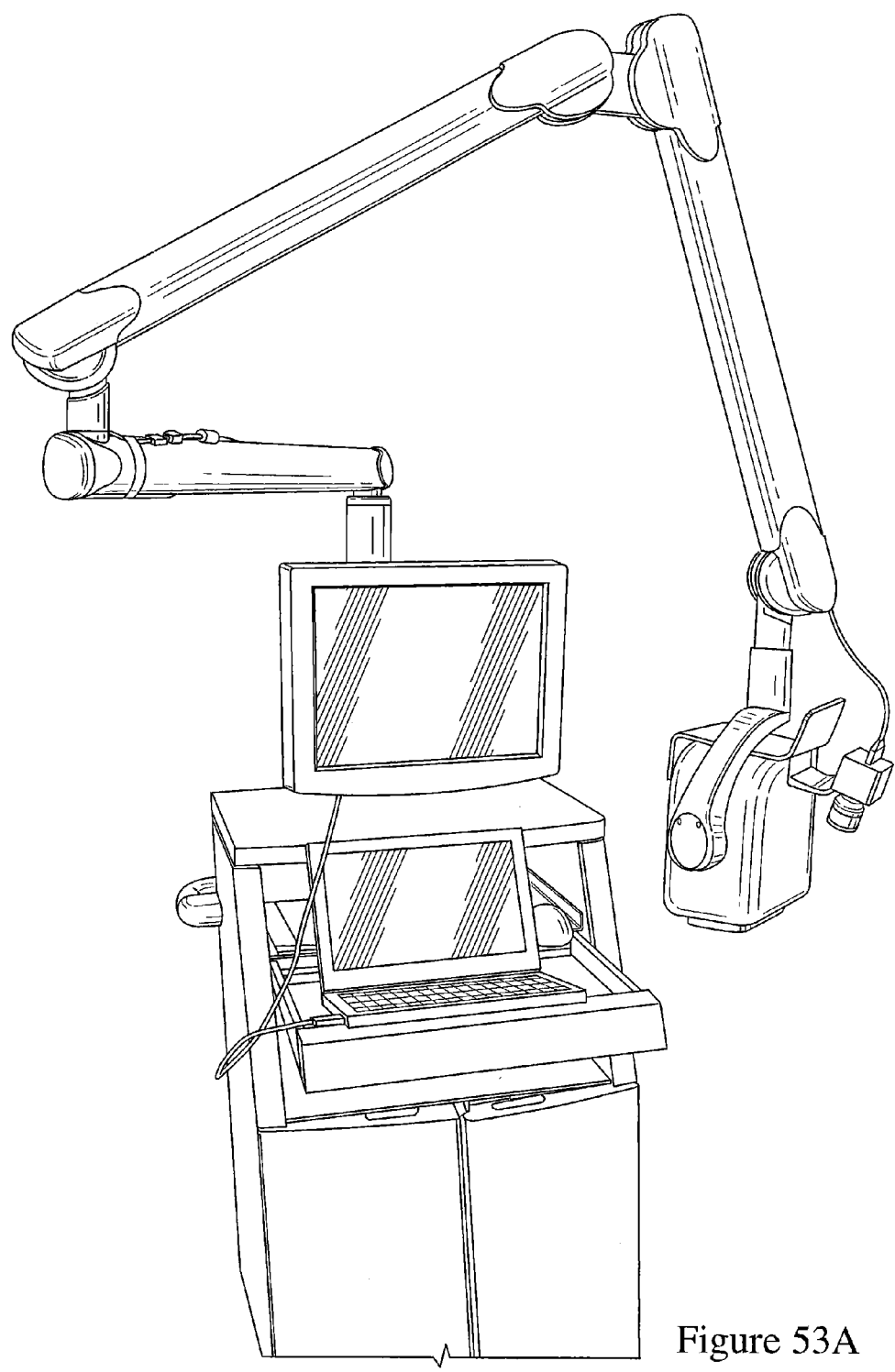
FIGS. 53A through 53D are images illustrating various aspects of the SPY system in accordance with some embodiments of the present inventive concept.
Figure 53B:
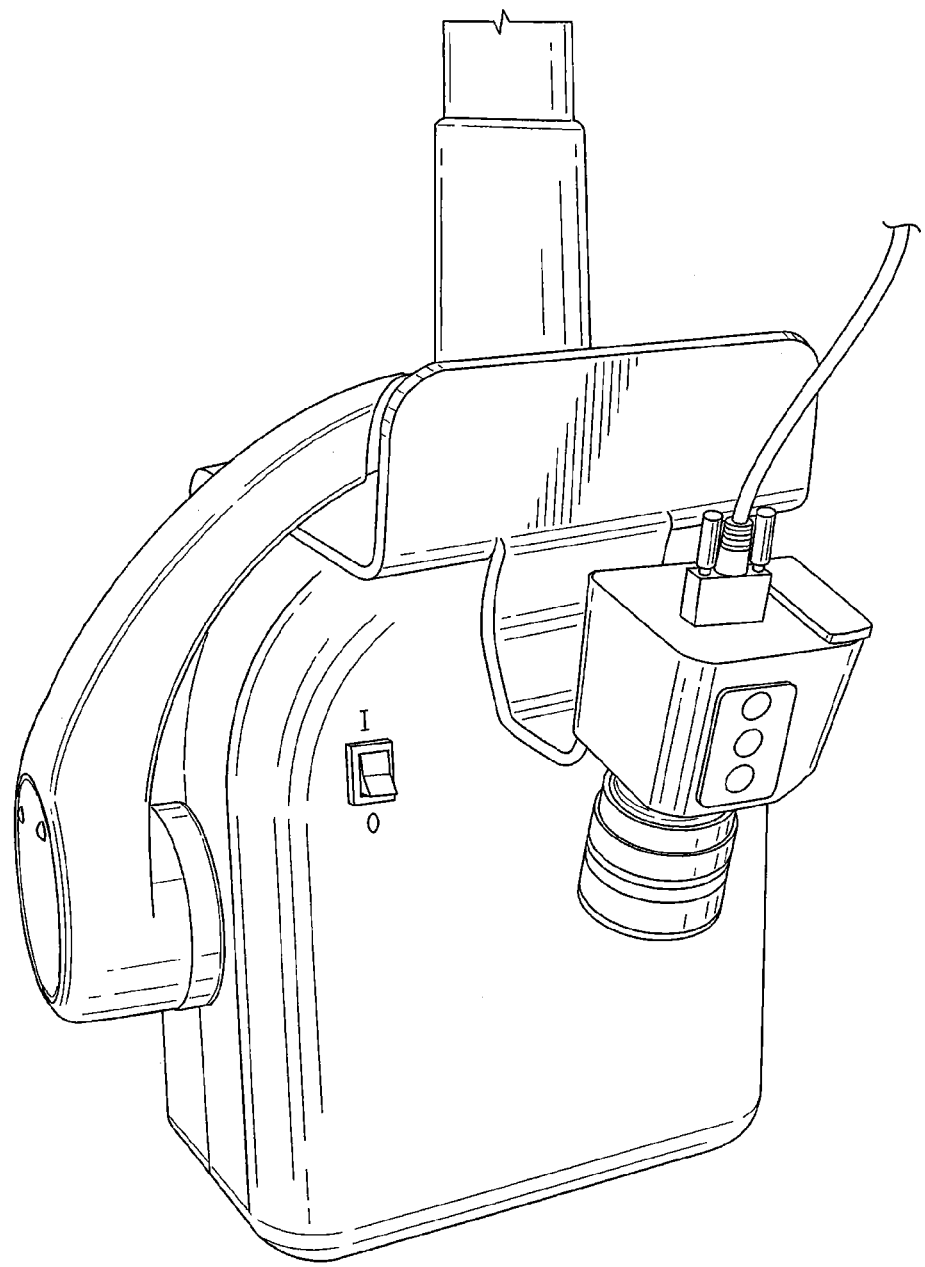
Figure 53C:
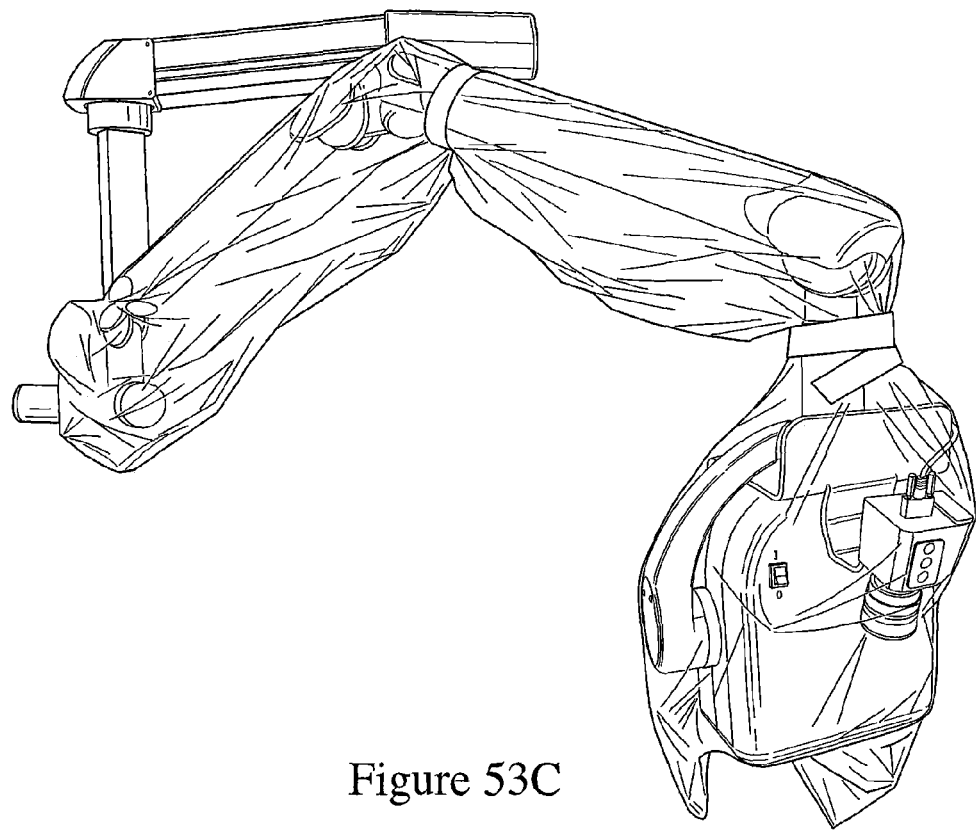
Figure 53D:
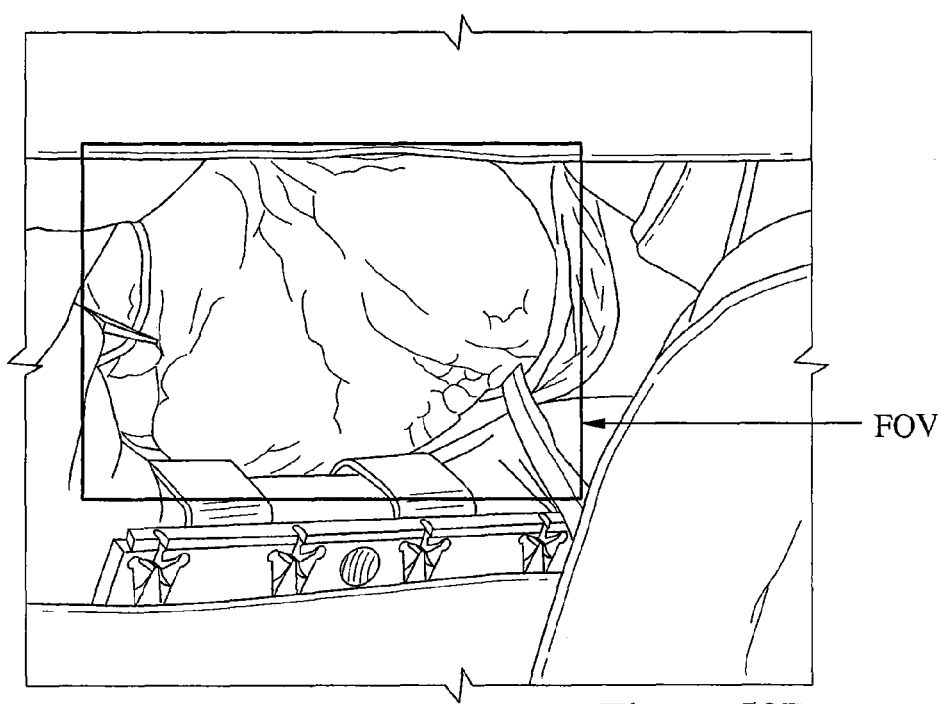

As discussed above, results in accordance with various embodiments discussed herein are affected by the quality of the equipment used to obtain the various measurements and images. Referring now to FIGS. 53A through 53D, in some embodiments images were obtained using a camera operating at 60 fps, twice that of the original camera used (30 fps). FIG. 53A is an illustration of the SPY device including the new camera configured to capture images at 60 fps. FIG. 53B is a larger view of the camera 5330 attached to the arm of the SPY device. FIG. 53C illustrates the system covered in plastic to provide a sanitary environment in the operating room. FIG. 53D illustrates the field of view (FOV) captured by the camera, which in this particular example is the heart of the patient.

Figures 54A, 54B, 54C:
FIGS. 54A through 54C are images illustrating a single LSI image, a laser speckle spatial contrast imaging (LSSCI) image and an LSCTI image, respectively, of a non-beating human heart in accordance with various embodiments of the present inventive concept.

Referring now to FIGS. 54A through 54C, images obtained from a non-beating heart using the system with the 60 fps camera discussed above will be discussed. In particular, FIG. 54A is a single image frame, FIG. 54B is an inverse LSSCI image obtained from images captured using the 60 fps camera and FIG. 54C is an inverse LSTCI image obtained from images captured using the 60 fps camera. Comparing images illustrated in FIG. 54A-54C and the images of FIGS. 50A-52B, it is clear that the structures of the heart are more clearly shown in the images obtained using the camera with higher fps. It is also clear that the LSTCI image is typically a better image than the LSSCI image.

Figure 55A:
FIGS. 55A through 55C are images illustrating a single LSI image, a laser speckle spatial contrast imaging (LSSCI) image and an LSCTI image, respectively, of a beating human heart in accordance with some embodiments of the present inventive concept.
Figure 55B:
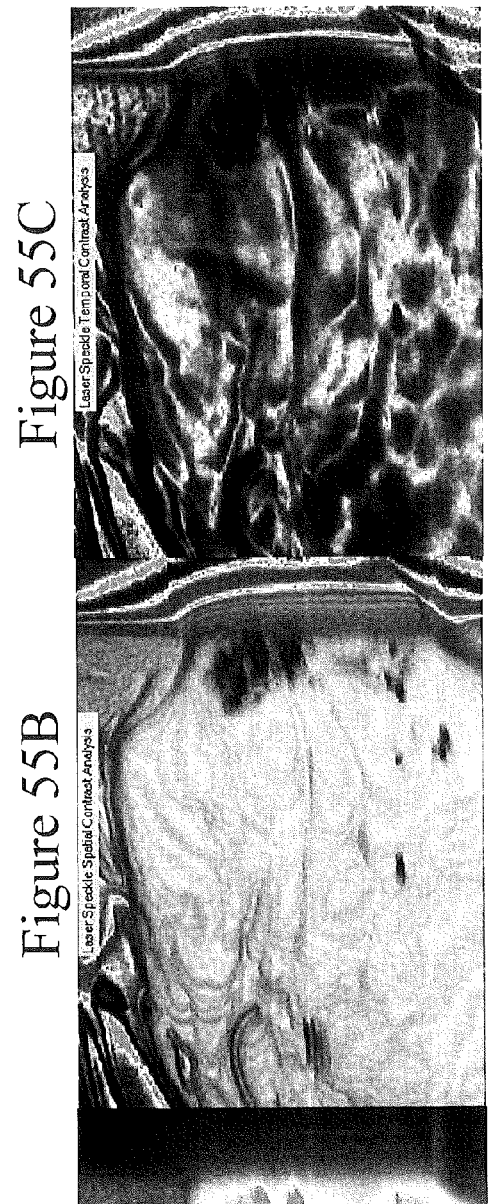
Figure 55C:

Referring now to FIGS. 55A through 55D, images obtained in a beating heart using the camera that obtains images at 60 fps camera will be discussed. FIG. 55A is a single image frame, FIG. 55B is an inverse LSSCI image obtained from images captured using a 60 fps camera and FIG. 55C is an inverse LSTCI image obtained using images generated with the 60 fps camera. Thus, embodiments of the present inventive concept may be used to capture images in a moving heart, thus, enabling instantaneous flow and perfusion measurements of the various arteries, veins, and tissues. However, as is clear from the images of FIGS. 55B and 55C, a camera that captures images at a higher fps rate would be desirable. For example, a camera speed of 600 fps would result in far more detailed images. Furthermore, many of the black areas of the images may be caused by inadvertent reflection off the sterile plastic cover illustrated in FIG. 53C that is provided for a sterile operating environment.

Figure 55D:
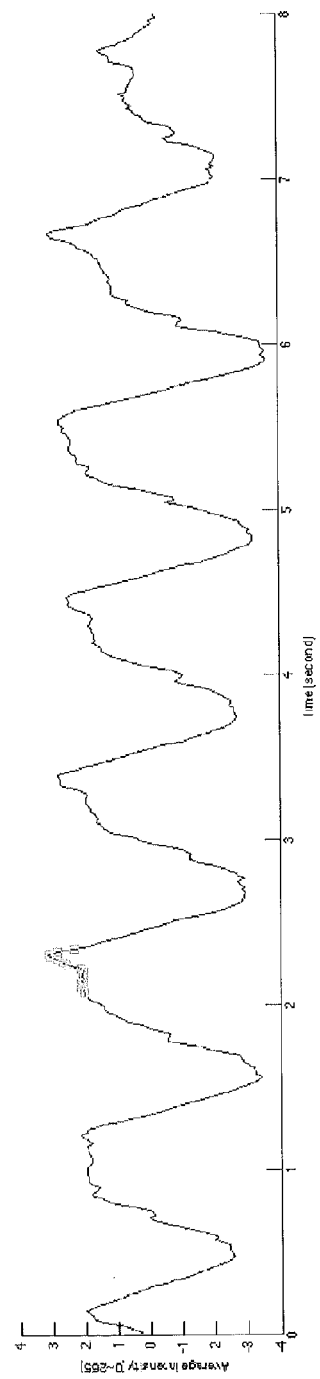
FIG. 55D is a graph of average intensity vs. time illustrating a pattern of movement of the beating heart in FIGS. 55A through 55C in accordance with some embodiments of the present inventive concept.

Referring now to FIG. 55D, a graph of average intensity vs. time in seconds will be discussed. This graph tracks the movement of the surface of the heart during the individual heartbeats, and acts as a surrogate for the EKG. The object distance between the camera lens and the heart surface changes with the heart cardiac cycle, moving closer and farther away within each cycle, causing the average intensity of an individual frame to fluctuate in this cyclical pattern shown in FIG. 55D. In addition, the average intensity vs. time curve can be filtered to be a surrogate EKG signal in accordance with embodiments discussed herein. In particular, the graph illustrates instantaneous LSI velocity measurements at any point in time in the cardiac cycle, for example, as indicated by the sequential squares on the peak at 2 secs. However, it is unclear which portions of the graph correspond to systole, i.e., indicating the maximum arterial pressure occurring during contraction of the left ventricle of the heart, and diastole, i.e. indicating the lowest arterial pressure during the interval between heartbeats. To determine which portions of the graph correspond to which cycles of the heart a constant is needed, for example, an EKG gating can be used as a temporal standard for analysis.

Figure 56A:
FIG. 56A is a still image of a beating heart in accordance with some embodiments of the present inventive concept.
Figure 56B:
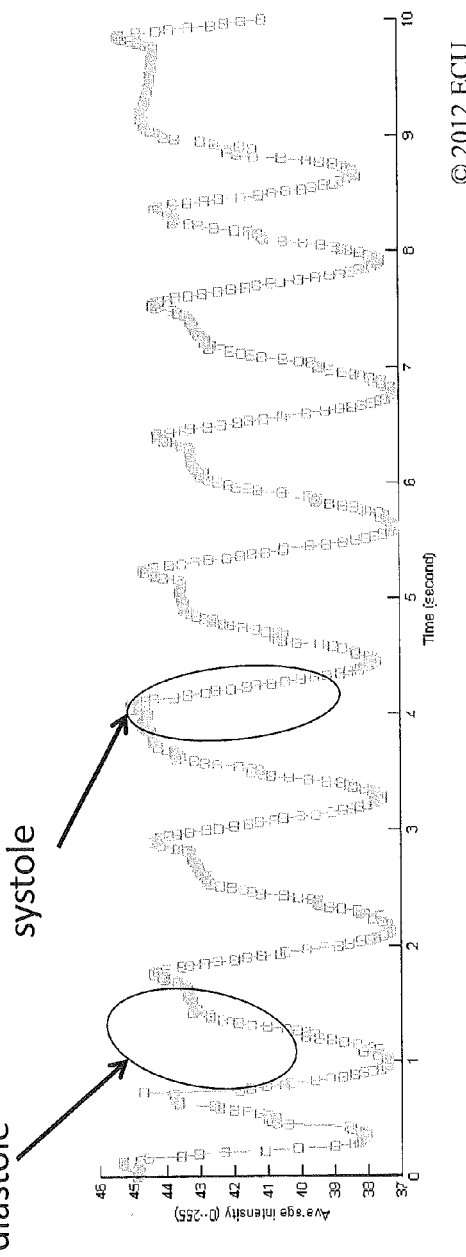
FIG. 56B is a graph of average intensity vs. time illustrating a pattern of movement of the beating heart and using EKG gating in accordance with some embodiments of the present inventive concept.

By observing the actual beating of the heart over a period of time, and incorporating the EKG gating concepts, it was determined which portions of the graph correspond to the relevant time-points in the cardiac cycles of the heart as illustrated in FIGS. 56A and 56B. FIG. 56A is a still shot from a movie of a moving heart used to obtain the graph of average intensity vs. time in seconds illustrating instantaneous LSI velocity measurements of FIG. 56B. As illustrated in FIG. 56B, by watching the moving heart and using EKG gating as discussed herein, the portions of the graph corresponding to diastole and systole were identified. The EKG gating concepts were used to separate the diastolic and systolic phases.

In embodiments discussed above, the EKG may be used to find, for example, a specific phase in the cardiac cycle where heart movement is minimized (diastole) and an instantaneous flow-perfusion map can be generated during this very short time period. In accordance with embodiments discussed herein, instantaneous flow and perfusion maps can be generated at any time in the cardiac cycle using EKG gating as discussed herein. In particular, embodiments of the present inventive concept take advantage of the fact that every patient in an operating room is connected to an EKG machine, and EKG machines are readily available in Clinics and other outpatient settings. Thus, the EKG can be used to synchronize the data collection and the analysis of the imaging data.

Average flow and perfusion maps can also be generated over several cardiac cycles used on the EKG gating embodiments discussed herein. Although embodiments discussed above use EKG synchronization in cardiac applications, embodiments of the present inventive concept are not limited to this configuration. EKG synchronization can be used as a methodology for non-cardiac triggered LSI applications to compare flow and perfusion using instantaneous/average flow and perfusion maps in other parts and organs of the body, i.e., non-cardiac portions.

In particular, when dealing with the heart (cardiac conditions and procedures) things happen pretty quickly, and an event can occur and be over in milliseconds. Also, blood flow varies dramatically (from zero to maximal). Thus, in cardiac applications, both instantaneous flow and average flow determinations typically require a method for locating and referencing time vs. what is happening physiologically. In other parts of the body outside the heart, blood flow is more constant, but instantaneous flow and average flow determinations still need a method for locating and referencing time vs. what is happening physiologically, i.e., some physiologic timer. Thus, in accordance with embodiments of the present inventive concept, the EKG can be used as a trigger for data collection, acquisition and analysis. Because things happen much slower outside of the heart, this EKG synchronization is also necessary as this physiologic timer for accurate results and can be used as a third rail for data collection.

Real time data collection and creation of instantaneous flow and perfusion maps may save a lot of time in a research environment. For example, if the researcher is studying the effect of vasoconstrictive/vasodialative drugs on the human body, i.e. how fast does the drug take effect, how long does it last and the like. Triggered LSI technology can be used on the area of interest in the body and flow and perfusion maps may be generated before, during and after administration of the drugs to access the necessary aspects. This same type of analysis may take days in the lab with multiple blood draws and scans being necessary.

Figure 57:
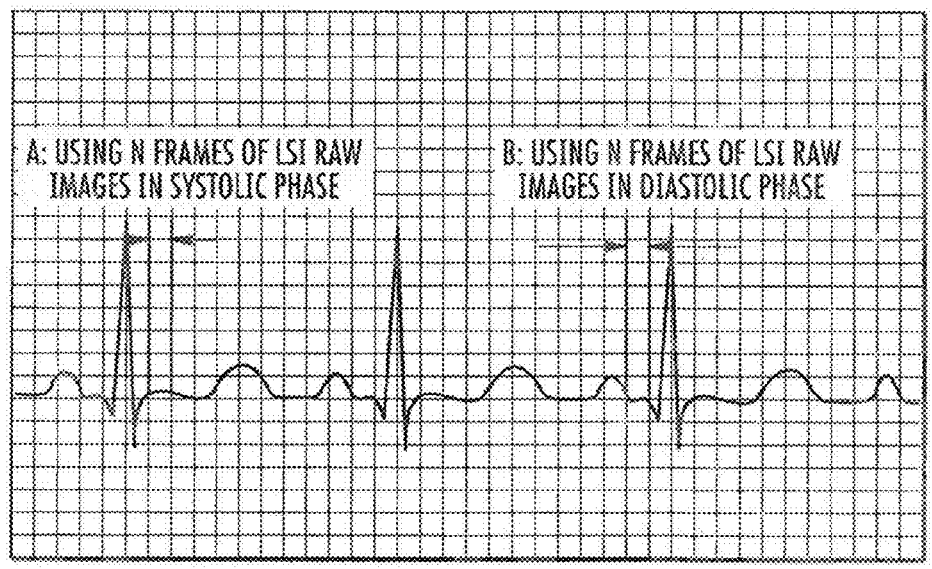
FIG. 57 is an example instantaneous flow and perfusion map that can be generated at any time in a cardiac cycle using EKG synchronization methods in accordance with some embodiments of the present inventive concept.

Referring now to FIG. 57, an example of how EKG gating could generate an instantaneous flow and perfusion map is illustrated. The EKG tracing shown is used to identify any selected component of the cardiac cycle, for example systole (Panel A) or diastole (Panel B). Because of this, the EKG can be used to trigger data acquisition, check for timing within the cycle, and used as an external temporal reference in non-cardiac applications of the embodiments discussed herein. As discussed above, an instantaneous flow and perfusion map may be generated at any time in a cardiac cycle using EKG synchronization techniques in accordance with embodiments discussed herein.

Figure 59A:
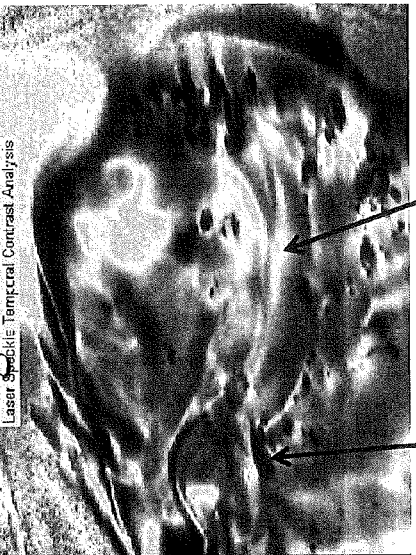
FIGS. 59A through 59C are images illustrating a single LSI image, an LSSCI image and an LSCTI image, respectively, of a beating human heart at end systole in accordance with some embodiments of the present inventive concept.
Figure 59B:
Figure 59C:
Figure 59D:
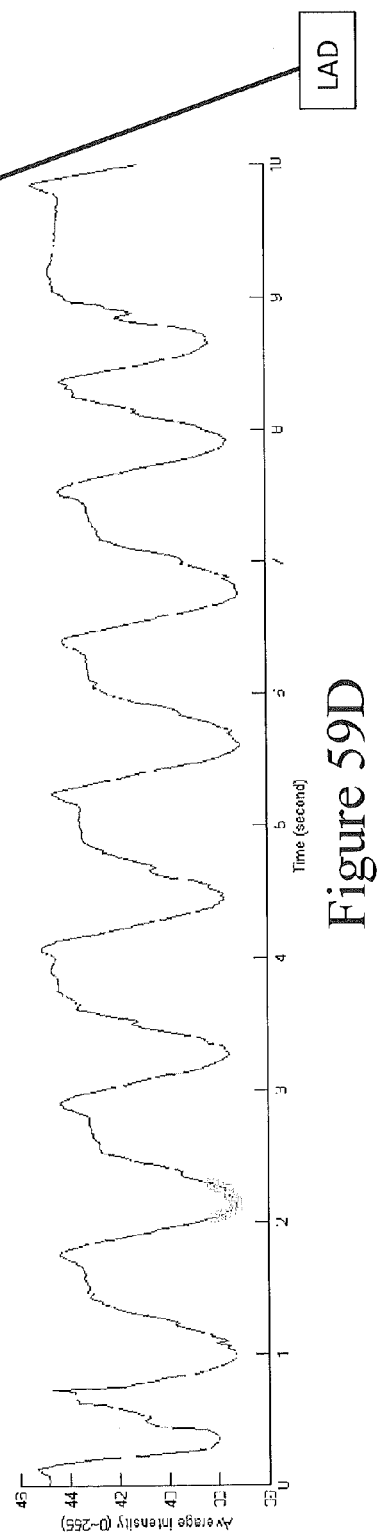
FIG. 59D is a graph of average intensity vs. time illustrating an instantaneous flow measurement of the beating heart in FIGS. 59A through 59C in accordance with some embodiments of the present inventive concept.

Referring now to FIGS. 58A through 59D, instantaneous flow measurements at times approximating end-diastole and end-systole will be discussed. The images in FIGS. 58A-C and 59A-C were obtained in a beating heart using the camera that obtains images at 60 fps camera. FIGS. 58A and 59A are single image frames, FIGS. 58B and 59B are inverse LSSCI images obtained from images generated using the 60 fps camera and FIGS. 58C and 59C are inverse LSTCI images obtained using images generated with the 60 fps camera. Thus, as discussed above, embodiments of the present inventive concept may be used to capture images in a moving heart, allowing instantaneous flow measurements from the various arteries, veins and tissues. FIGS. 58A-58C are images representing an anterior wall of the heart at a time approximating end-diastole (max blood flow). FIG. 58C specifically illustrates the graft inserted by the surgeon into the LAD. FIG. 58D is a graph of average intensity vs. time in seconds and illustrates instantaneous LSI velocity measurements at any point in time in the cardiac cycle. The highlighted portions of the graph correspond to velocities at a time approximating end-diastole. This graph is generated in a similar fashion to that described in FIG. 55D. FIGS. 59A through 59C are images representing an anterior wall of the heart at a time approximating end-systole (min blood flow). FIG. 59C specifically illustrates the graft inserted by the surgeon and the LAD. FIG. 59D is a graph of average intensity vs. time in seconds and illustrates instantaneous LSI velocity measurements at any point in time in the cardiac cycle. The highlighted portions (squares) of the graph correspond to velocities at a time approximating end-systole. This graph is generated in a similar fashion to that described in FIG. 55D. As is clear from comparing these graphs, differences in velocities can be measured in a beating heart using the LSI method discussed herein. The differences in blood flow can even be seen by comparing the LAD of FIG. 58C and the LAD of FIG. 59C.

Figure 60:
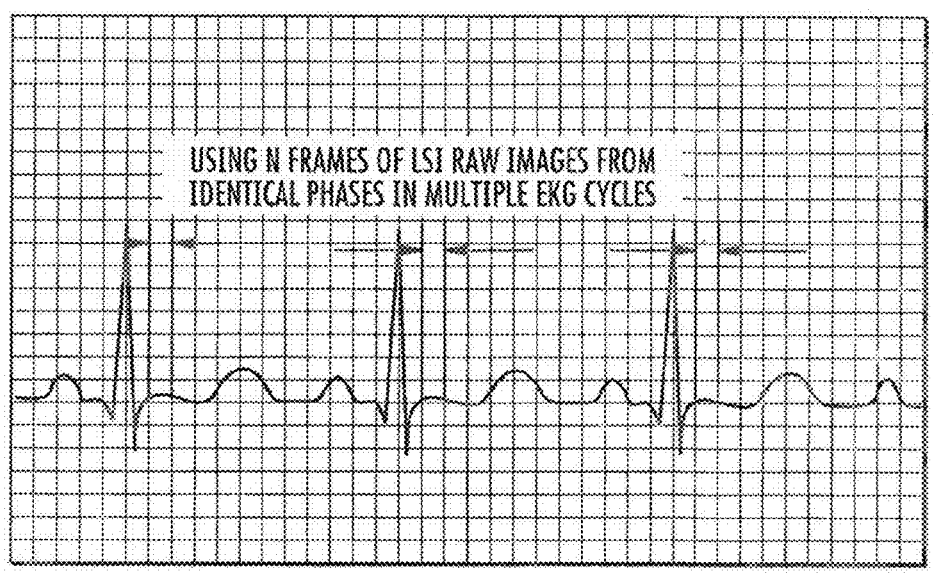
FIG. 60 is an example average flow and perfusion map that can be generated in two or more cardiac cycles using EKG synchronization methods in accordance with some embodiments of the present inventive concept.

Referring now to FIG. 60, this is an example of how average flow and perfusion can be generated from the EKG triggering and analysis. As discussed above, an average flow and perfusion map may be generated by combining image data from two or more several cardiac cycles using EKG synchronization techniques in accordance with embodiments discussed herein. This EKG trace illustrates capture of data during systole sequentially from three cardiac cycles.

Referring now to FIGS. 61A through 62D, average flow measurements in diastole and systole during multiple cardiac cycles will be discussed. The images in FIGS. 61A-C and 62A-C were obtained in a beating heart using the camera that obtains images at 60 fps camera. FIGS. 61A and 62A are single image frames, FIGS. 61B and 62B are inverse LSSCI images obtained using the 60 fps camera and FIGS. 61C and 62C are inverse LSTCI images obtained using images generated with the 60 fps camera. Thus, as discussed above, embodiments of the present inventive concept may be used to capture images in a moving heart, allowing average flow measurements of the various arteries, veins and tissues during multiple cardiac cycles to be generated. FIGS. 61A-61C are images representing an anterior wall of the heart at a time approximating end-diastole (max blood flow) during multiple cardiac cycles. FIG. 61D is a graph of average intensity vs. time in seconds and illustrates average LSI velocity measurements during multiple cardiac cycles. This graph is generated in identical fashion to FIG. 55D, but in this case illustrates image acquisition data at a time approximating end-diastole from 9 sequential cardiac cycles for analysis. The highlighted portions of the graph correspond to velocities at a times approximating end-diastole from the multiple cycles. FIGS. 62A-62C are images representing an anterior wall of the heart at a time approximating end-systole (min blood flow). FIG. 62D is a graph of average intensity vs. time in seconds and illustrates average LSI velocity measurements at any point in time in the cardiac cycle. This graph was generated in a similar fashion to FIG. 55D, but in this case illustrates image acquisition data at a time approximating end-systole from 8 sequential cardiac cycles for analysis. The highlighted portions of the graph correspond to velocities at a time approaching end-systole. As is clear from comparing these graphs, differences in velocities can be measured in a beating heart using the LSI method discussed herein. To compare flow and perfusion maps, for example, before and after an intervention, EKG synchronization is an ideal technique. As discussed above, every patient in an operating room has an EKG. In addition, EKG machines are readily available in all clinic and outpatient environments. An EKG is a standardized, physiologic timing template that can be used as a baseline for comparison. This is a positive because in physiology, time phase is not standard across LSI clinical applications. EKG also creates the analytical basis for comparison of instantaneous flow and perfusion maps, because the flow and perfusion patterns will vary based on the physiology/pathophysiology of blood flow and perfusion. EKG synchronization is an ideal way to link the flow and perfusion to an independent, objective benchmark, i.e, a specific cardiac phase.

EKG also creates an analytical basis for comparison of average flow and perfusion maps because the objective precision of the EKG is ideal for defining the starting and ending points of the averaging process versus simply finding a random starting point and averaging a few seconds of imaging data.

Referring now to FIGS. 63A through 63D, embodiments of the present inventive concept using EKG gating concepts to provide information related to graft procedures will be discussed. The images in FIGS. 63A through 63C were obtained in a beating heart using the camera that obtains images at 60 fps camera. FIG. 63A is a single image frame, FIG. 63B is an inverse LSSCI image obtained using images generated by the 60 fps camera and FIG. 63C is an inverse LSTCI image obtained using images generated with the 60 fps camera. In embodiments illustrated in FIGS. 63A-C, a clamp has been placed on the bypass graft to simulate native blood flow through the arteries, veins and tissues before the bypass graft was inserted into the patient. FIG. 63D is a graph of average intensity vs. time in seconds and illustrates evolution of perfusion change induced by bypass grafting. This graph was generated in a similar fashion to FIG. 55D, with three cycles analyzed at a time approximating end-diastole (maximal coronary blood flow). As illustrated in FIG. 63C, there is no flow through the graft when the clamp on the graft and thus, the flow through the LAD would be equivalent to the flow before the graft was inserted into the patient.

Figure 64C:
FIGS. 64A through 64C are images illustrating a single LSI image, an LSSCI image and an LSCTI image, respectively, of a beating human heart including a bypass graft where the clamp has been removed in accordance with some embodiments of the present inventive concept.
Figure 64B:
Figure 64A:
Figure 64D:
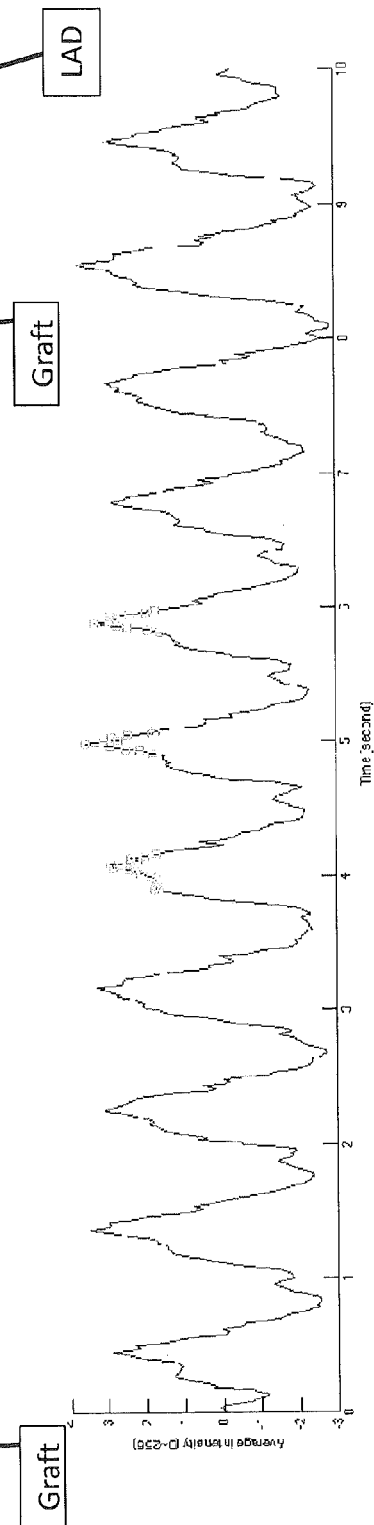
FIG. 64D is a graph of average intensity vs. time of the beating heart in FIGS. 64A through 64C in accordance with some embodiments of the present inventive concept.

In stark contrast, FIGS. 64A through 64D, illustrate embodiments where the clamp has been removed from the graft and blood was allowed to flow through the graft. The images in FIGS. 64A through 64C were obtained in a beating heart using the camera that obtains images at 60 fps camera. FIG. 64A is a single image frame, FIG. 64B is an inverse LSSCI image obtained using imaged generated by the 60 fps camera and FIG. 64C is an inverse LSTCI image obtained using images generated with the 60 fps camera. As illustrated in FIG. 64C, there is blood flow through the graft and blood flow through the LAD has increased. FIG. 64D is a graph of average intensity vs. time in seconds and illustrates evolution of perfusion change induced by bypass grafting. This graph was generated in a similar fashion to FIG. 55D, with three cycles again analyzed at a time approximating end-diastole. Thus, with this EKG-concept timing, FIG. 64C can be directly compared to FIG. 63C, with the imaging difference being the flow and velocity resulting from the bypass graft to the heart vessel.

This comparison between FIGS. 63C and 64C illustrates the concept of EKG triggering for data acquisition, and EKG timing for average velocities and comparative analysis of those average velocities. Comparison of instantaneous velocities could be accomplished in the same manner, in any physiologic circumstance where study of blood flow and tissue perfusion was indicated.

However, as discussed above, embodiments of the present inventive concept do not have to be used in cardiac applications. In other words, LSI technology can be extended to other applications. Physiologically, the cardiac application is the most complicated for flow and perfusion analysis. Other applications such as wound healing, tissue reconstruction, vascular surgery and transplantation have fewer challenges for triggered LSI imaging.

Figure 65C:
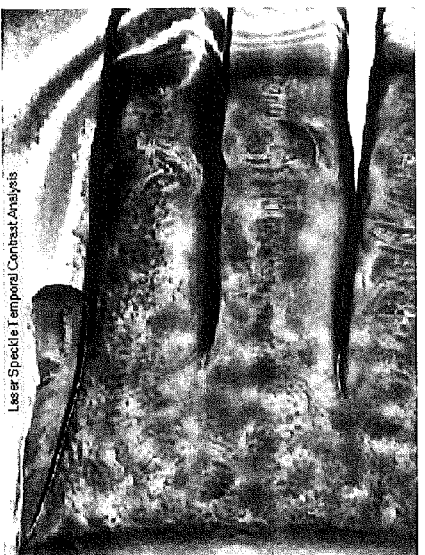
FIGS. 65A through 65C are images illustrating a single LSI image, an LSSCI image and an LSCTI image, respectively, of a human hand in accordance with some embodiments of the present inventive concept.
Figure 65B:
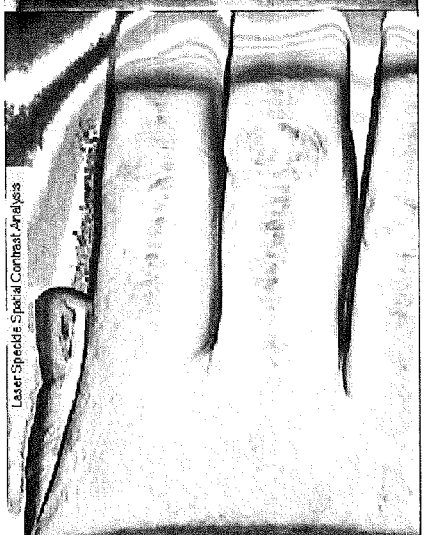
Figure 65A:
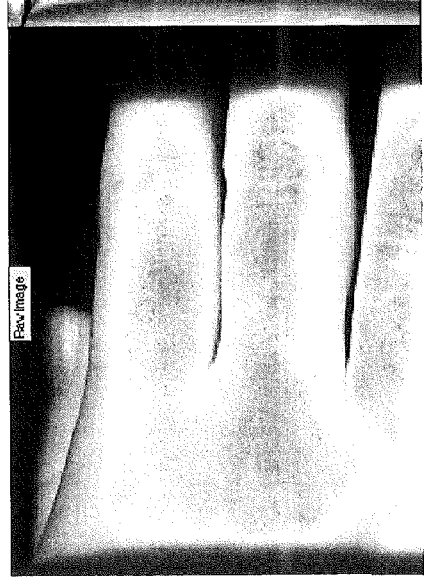

Referring now to FIGS. 65A through 65C, images of a hand of a person generated using embodiments discussed herein will be discussed. FIG. 65A is a single image frame, FIG. 65B is an inverse LSSCI image obtained using images generated by the 60 fps camera and FIG. 65C is an inverted LSTCI obtained using images generated with the 60 fps camera. These images clearly illustrate microvascular blood flow in the human hand using LSI technology in accordance with embodiments discussed herein.

Using triggered LSI in accordance with embodiments of the present inventive concept, real time flow and perfusion maps may be generated during procedures. Thus, a success of a procedure may be immediately assessed and remedied, if necessary. Flow is measured as ccs/minute. Since the frame rate of a camera is slower than a processor, for example, data processing system 200 of FIG. 2A, in a communications device, the algorithm for generating the flow and perfusion diagrams can be hard coded into the system to provide real time information to the person performing the procedure. As discussed above, this real time information can be invaluable.

Figure 66:
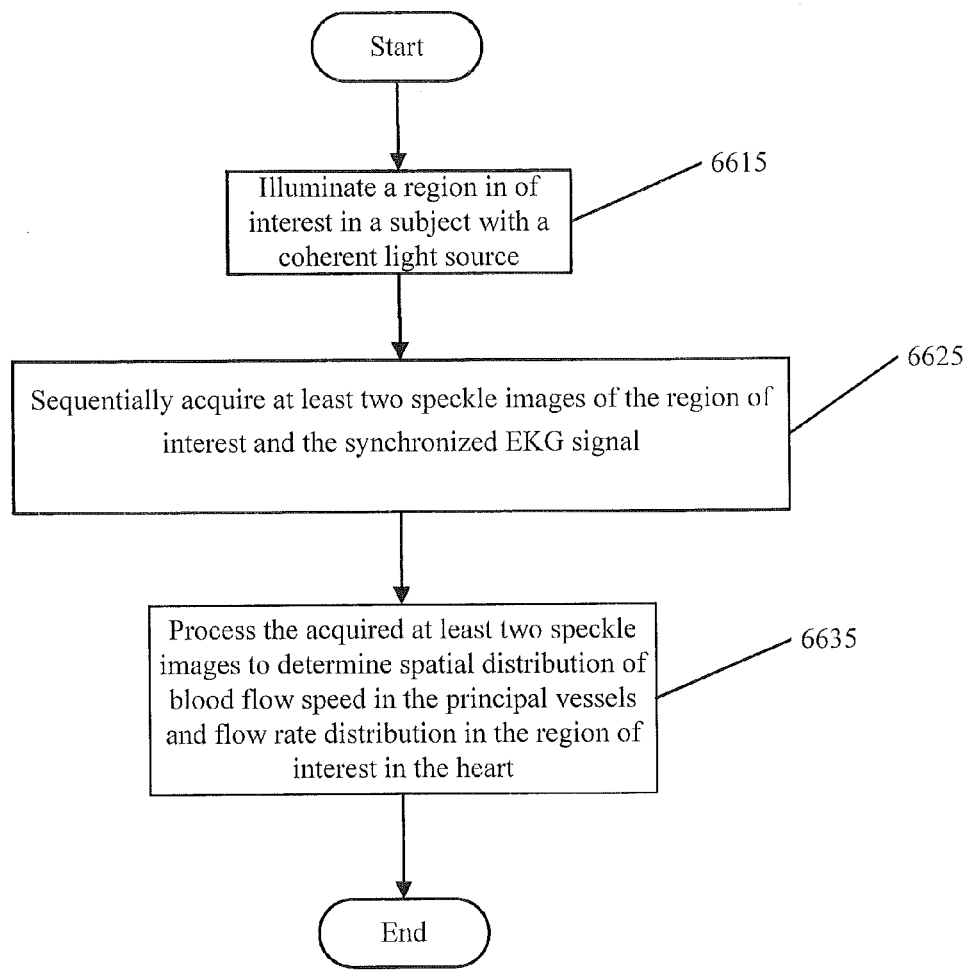
FIGS. 66 and 67 are flowcharts illustrating operations in accordance with various embodiments discussed herein.
Figure 67:
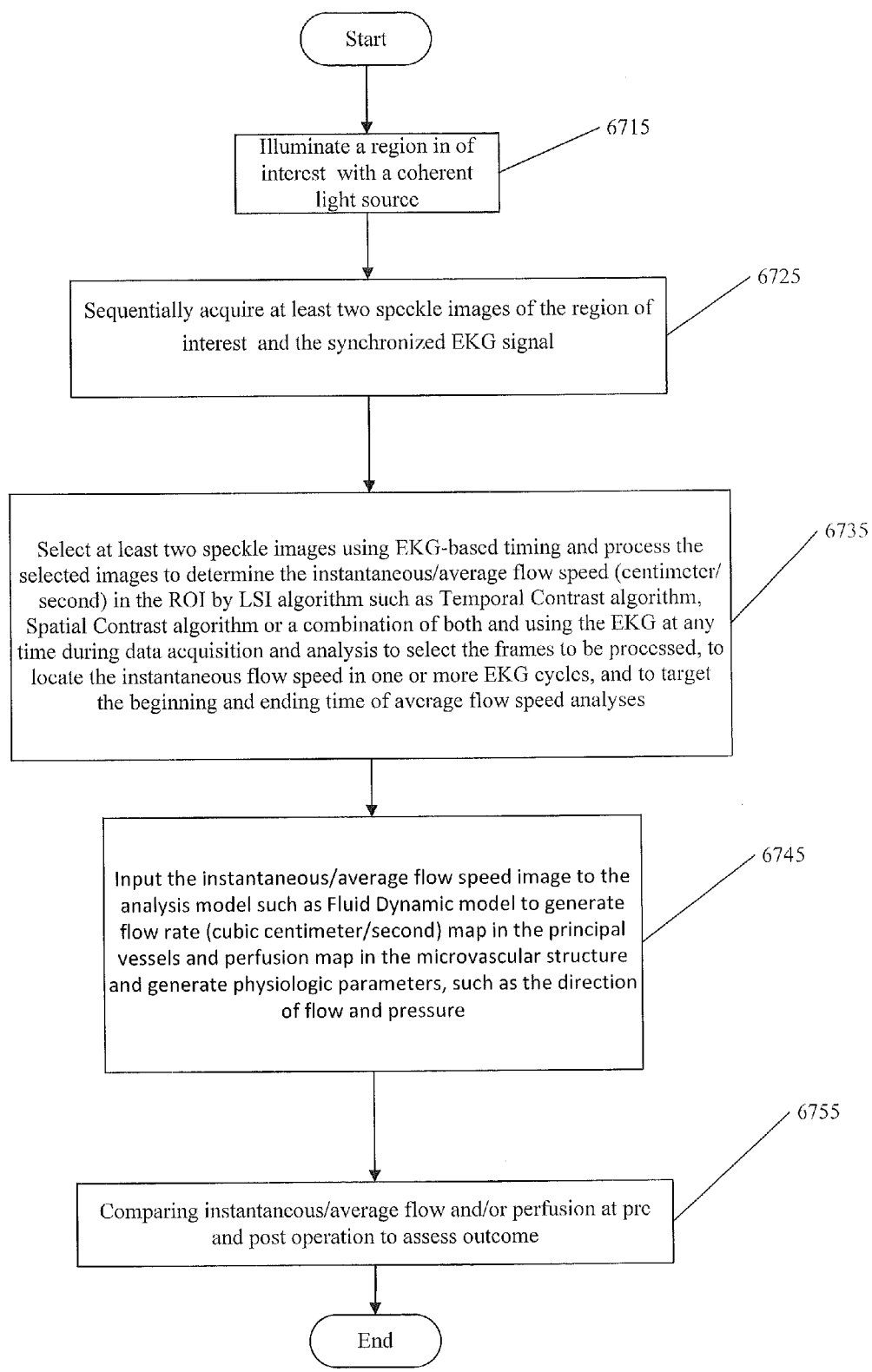

Referring now to FIGS. 66 and 67, flowcharts illustrating operations in accordance with various embodiments of the present inventive concept will be discussed. Referring first to FIG. 66, operations begin at block 6615 illuminating a region of interest of a subject with a coherent light source. At least two speckle images are acquired of the region of interest (block 6625). The at least two speckle images are acquired in synchronization along with a simultaneously acquired EKG tracing as the timing signal. The at least two acquired speckle images are electronically processed based on the temporal variation of the pixel intensities in the at least two acquired speckle images to generate a laser speckle contrast imaging (LSCI) image, determine distribution of blood flow speed in principal vessels and quantify perfusion distribution in tissue in the region of interest from the LSCI image (block 6635). As discussed above, in accordance with embodiments discussed herein, the LSCI image enables detection of different blood flow speeds, which is not possible in conventional methods.

Referring now to FIG. 67, operations begin at block 6715 by illuminating a region of interest of a subject with a coherent light source. At least two speckle images are acquired of the region of interest (block 6725). The at least two speckle images are acquired in synchronization, along with a simultaneously acquired EKG trace as the timing signal (block 6725). Using EKG-based timing to select frames for instantaneous or average flow analysis, the at least two acquired speckle images are electronically processed based on the temporal, spatial, or combination of both contrast variation of the pixel intensities to generate a laser speckle contrast imaging (LSCI) image (block 6735). This LSCI image is proportional to the flow speed of the region of interest. Using EKG as the corresponding physiologic timing locater LSCI is used to determine the instantaneous flow speed in the principal vessels and/or perfusion in the tissue at any time in one EKG cycle and average flow speed in the principal vessels and/or perfusion in the tissue in two or more EKG cycles (block 6735). The flow speed image is further input into an analytical model such as fluid dynamic model to generate many measurements such as volume flow rate in the principal vessels and quantified perfusion map in the tissue, flow direction and pressure distribution etc. (block 6745). The instantaneous flow rate and/or perfusion maps or the average flow rate and/or perfusion maps generated at pre and post operation are compared to determine efficacy of a treatment (6755).

It will be understood that the region of interest may be a cardiac region of interest or a non-cardiac region of interest without departing from the scope of the present inventive concept.

As discussed above, embodiments of the present inventive concept may be used to not only determine blood flow velocity, but blood flow rates and velocity integrated across cross section areas of the blood vessels. The measurements are obtained according to heart beat timing signals of an electrocardiogram (EKG). The results of the measurement of blood flow distribution are validated using triggered LSI and enhanced by hydrodynamic modeling of blood flows.

The foregoing is illustrative of the present inventive concept and is not to be construed as limiting thereof. Although a few exemplary embodiments of the present inventive concept have been described, those skilled in the art will readily appreciate that many modifications are possible in the exemplary embodiments without materially departing from the novel teachings and advantages of this inventive concept. Accordingly, all such modifications are intended to be included within the scope of the inventive concept as defined in the claims. In the claims, means-plus-function clauses, where used, are intended to cover the structures described herein as performing the recited function and not only structural equivalents but also equivalent structures. Therefore, it is to be understood that the foregoing is illustrative of the present inventive concept and is not to be construed as limited to the specific embodiments disclosed, and that modifications to the disclosed embodiments, as well as other embodiments, are intended to be included within the scope of the appended claims. The inventive concept is defined by the following claims, with equivalents of the claims to be included therein.

That which is claimed is:

1. A non-invasive method for determining blood flow distribution in a region of interest, the method comprising:
    illuminating a region of interest of a subject with a coherent light source;
    sequentially acquiring at least two speckle images of the region of interest, wherein sequentially acquiring the at least two speckle images comprises acquiring the at least two speckle images in synchronization with motion of the heart of the subject; and
    electronically processing the at least two acquired speckle images based on the temporal variation of the pixel intensities in the at least two acquired speckle images to generate a laser speckle contrast imaging (LSCI) image, determine distribution of blood flow speed in principal vessels and quantify perfusion distribution in tissue in the region of interest from the LSCI image,
    wherein the LSCI image enables detection of different blood flow speeds.

2. The method of claim 1, wherein sequentially acquiring the at least two speckle images comprises acquiring the at least two speckle images in synchronization with motion of the heart of the subject further comprises:
    electronically monitoring an EKG cardiac cycle of the subject; and
    electronically synchronizing acquisition of speckle images with the EKG signals.

3. The method of claim 2, wherein the region of interest is a beating heart, the method further comprising generating instantaneous flow and/or perfusion maps for the region of interest at any time during a cardiac cycle using the EKG signals to synchronize data acquisition.

4. The method of claim 3, further comprising comparing instantaneous flow and/or perfusion maps generated at first and second times to determine efficacy of a treatment.

5. The method of claim 4, wherein the first time is a time before a treatment is administered and wherein the second time is a time after the treatment is administered.

6. The method of claim 2, wherein the region of interest is a beating heart, the method further comprising generating average flow and/or perfusion maps for the region of interest over two or more cardiac cycles using EKG signals to synchronize data acquisition.

7. The method of claim 6, further comprising comparing average flow and/or perfusion maps generated at first and second times to determine efficacy of a treatment.

8. The method of claim 7, wherein the first time is a time before a treatment is administered and wherein the second time is a time after the treatment is administered.

9. The method of claim 2, wherein the region of interest is a non-cardiac region of the subject, the method further comprising generating instantaneous flow and/or perfusion maps at any time during data acquisition using the EKG signals to synchronize data acquisition.

10. The method of claim 9, further comprising comparing instantaneous flow and/or perfusion maps generated at first and second times to determine efficacy of a treatment.

11. The method of claim 10, wherein the first time is a time before a treatment is administered and wherein the second time is a time after the treatment is administered.

12. The method of claim 2, wherein the region of interest is a non-cardiac region of the subject, the method further comprising generating average flow and/or perfusion maps over two or more periods of data acquisition using EKG signals to synchronize data acquisition.

13. The method of claim 12, further comprising comparing average flow and/or perfusion maps generated at first and second times to determine efficacy of a treatment.

14. The method of claim 13, wherein the first time is a time before a treatment is administered and wherein the second time is a time after the treatment is administered.

15. The method of claim 1, wherein the coherent light source has a wavelength of from about 600 nm to about 1100 nm.

16. A non-invasive method for determining blood flow distribution in a region of interest, the method comprising:
    illuminating a region of interest of a subject with a coherent light source;
    sequentially acquiring at least two speckle images of the region of interest, wherein sequentially acquiring the at least two speckle images comprises acquiring the at least two speckle images in synchronization with motion of the heart of the subject;
    electronically processing the at least two acquired speckle images based on the temporal variation of the pixel intensities in the at least two acquired speckle images to generate a laser speckle contrast imaging (LSCI) image, determine distribution of blood flow speed in principal vessels and quantify perfusion distribution in tissue in the region of interest from the LSCI image;
    generating one of instantaneous flow and/or perfusion maps for the region of interest at any time during data acquisition using EKG signals to synchronize data acquisition and average flow and/or perfusion maps over two or more periods of data acquisition using the EKG signals to synchronize data acquisition; and
    comparing one of the instantaneous flow and/or perfusion maps and the average flow and/or perfusion maps generated at first and second times to determine efficacy of a treatment.

17. The method of claim 16, wherein the region of interest is a beating heart.

18. A non-invasive system for determining blood flow distribution in a region of interest, the system comprising:
   a coherent light source configured to illuminate a region of interest of a subject;
   a camera in communication with the coherent light source that is configured to sequentially acquire at least two speckle images of the region of interest, wherein acquisition of the at least two speckle images is synchronized with motion of the heart of the subject; and
   a data processing circuit configured to evaluate the temporal variation of the pixel intensities in the at least two acquired speckle images to generate a laser speckle contrast imaging (LSCI) image, determine distribution of blood flow speed in the principal vessels and quantify perfusion distribution in tissue in the region of interest in the heart from the LSCI image, wherein the LSCI image enables detection of different blood flow speeds.

19. The system of claim 18, wherein the data processing circuit is further configured to:
   electronically monitor an EKG cardiac cycle of the subject; and
   electronically synchronize acquisition of speckle images with the EKG signals.

20. The system of claim 19, wherein the region of interest is a beating heart, the system further comprising a modeling module configured to generate instantaneous flow and/or perfusion maps for the region of interest at any time during a cardiac cycle using the EKG signals to synchronize data acquisition.

21. The system of claim 20, wherein the data processing circuit is further is configured to compare instantaneous flow and/or perfusion maps generated at first and second times to determine efficacy of a treatment.

22. The system of claim 19, wherein the region of interest is a beating heart, the system further comprising a modeling module configured to generate average flow and/or perfusion maps for the region of interest over two or more cardiac cycles using EKG signals to synchronize data acquisition.

23. The system of claim 22, wherein the data processing circuit is further configured to compare average flow and/or perfusion maps generated at first and second times to determine efficacy of a treatment.

24. The system of claim 19, wherein the region of interest is a non-cardiac region of the subject, the system further comprising a modeling module configured to generate instantaneous flow and/or perfusion maps at any time during data acquisition using the EKG signals to synchronize data acquisition.

25. The system of claim 24, wherein the data processing circuit is further configured to compare instantaneous flow and/or perfusion maps generated at first and second times to determine efficacy of a treatment.

26. The system of claim 19, wherein the region of interest is a non-cardiac region of the subject, the system further comprising a modeling module configured to generate average flow and/or perfusion maps over two or more periods of data acquisition using EKG signals to synchronize data acquisition.

27. The method of claim 26, wherein the data processing circuit is further configured to compare average flow and/or perfusion maps generated at first and second times to determine efficacy of a treatment.

28. A computer program for determining blood flow distribution in a region of interest, the computer program being stored in a non-transitory computer-readable storage medium, the computer-readable program code comprising:
   computer readable program code configured to illuminate a region of interest of a subject with a coherent light source;
   computer readable program code configured to sequentially acquire at least two speckle images of the region of interest, wherein sequentially acquiring the at least two speckle images comprises acquiring the at least two speckle images in synchronization with motion of the heart of the subject;
   computer readable program code configured to electronically process the at least two acquired speckle images based on the temporal variation of the pixel intensities in the at least two acquired speckle images to generate a laser speckle contrast imaging (LSCI) image, determine distribution of blood flow speed in principal vessels and quantify perfusion distribution in tissue in the region of interest from the LSCI image;
   computer readable program code configured to generate one of instantaneous flow and/or perfusion maps for the region of interest at any time during data acquisition using EKG signals to synchronize data acquisition and average flow and/or perfusion maps over two or more periods of data acquisition using the EKG signals to synchronize data acquisition; and
   computer readable program code configured to compare one of the instantaneous flow and/or perfusion maps and the average flow and/or perfusion maps generated at first and second times to determine efficacy of a treatment.

* * * * *